(12) United States Patent
Neogi et al.

(10) Patent No.: US 7,718,682 B2
(45) Date of Patent: May 18, 2010

(54) HETEROCYCLIC ANALOGS OF DIPHENYLETHYLENE COMPOUNDS

(75) Inventors: Partha Neogi, Fremont, CA (US); Debendranath Dey, Fremont, CA (US); Satyanarayana Medicherla, Cupertino, CA (US); Bishwagit Nag, Union City, CA (US); Arthur Lee, San Francisco, CA (US)

(73) Assignee: Theracos, Inc., Sunnyvale, CA (US)

( * ) Notice: Subject to any disclaimer, the term of this patent is extended or adjusted under 35 U.S.C. 154(b) by 0 days.

(21) Appl. No.: 12/078,662

(22) Filed: Apr. 2, 2008

(65) Prior Publication Data

US 2008/0293949 A1 Nov. 27, 2008

Related U.S. Application Data

(63) Continuation of application No. 10/265,902, filed on Oct. 8, 2002, now Pat. No. 7,407,978, which is a continuation-in-part of application No. 09/843,167, filed on Apr. 27, 2001, now Pat. No. 7,105,552, which is a continuation-in-part of application No. 09/785,554, filed on Feb. 20, 2001, now abandoned, which is a continuation-in-part of application No. 09/591,105, filed on Jun. 9, 2000, now abandoned, which is a continuation-in-part of application No. 09/287,237, filed on Apr. 6, 1999, now Pat. No. 6,331,633.

(51) Int. Cl.
*A61K 31/426* (2006.01)
(52) U.S. Cl. ..................... 514/369
(58) Field of Classification Search ................. 514/369; 548/183
See application file for complete search history.

(56) References Cited

U.S. PATENT DOCUMENTS

| | | | |
|---|---|---|---|
| 3,609,183 A | 9/1971 | DeWald et al. |
| 3,683,009 A | 8/1972 | Middleton |
| 3,846,398 A | 11/1974 | Hirschmann et al. |
| 4,092,335 A | 5/1978 | Gruszecki et al. |
| 4,217,366 A | 8/1980 | Kikumoto et al. |
| 4,271,186 A | 6/1981 | Forster et al. |
| 4,284,637 A | 8/1981 | Kikumoto et al. |
| 4,297,429 A | 10/1981 | Kanada et al. |
| 4,310,534 A | 1/1982 | Kikumoto et al. |
| 4,312,855 A | 1/1982 | Grand |
| 4,326,055 A | 4/1982 | Loeliger |
| 4,464,382 A | 8/1984 | Tanouchi et al. |
| 4,716,905 A | 1/1988 | Schmued |
| 4,866,086 A | 9/1989 | Boyle et al. |
| 4,929,635 A | 5/1990 | Coquelet et al. |
| 4,940,707 A | 7/1990 | Klaus et al. |
| 5,087,637 A | 2/1992 | Janssen et al. |
| 5,158,966 A | 10/1992 | Lafferty et al. |
| 5,162,337 A | 11/1992 | Elbrecht et al. |
| 5,171,753 A | 12/1992 | Munson, Jr. et al. |
| 5,189,056 A | 2/1993 | Orlando et al. |
| 5,225,426 A | 7/1993 | Miyaoka et al. |
| 5,246,936 A | 9/1993 | Treacy et al. |
| 5,250,562 A | 10/1993 | Klaus et al. |
| 5,314,693 A | 5/1994 | Suga |
| 5,378,705 A | 1/1995 | Klaus et al. |
| 5,409,953 A | 4/1995 | Pettit et al. |
| 5,430,062 A | 7/1995 | Cushman et al. |
| 5,436,257 A | 7/1995 | Fujita et al. |
| 5,478,852 A | 12/1995 | Olefsky et al. |
| 5,494,932 A | 2/1996 | Cardin et al. |
| 5,521,160 A | 5/1996 | Chucholowski et al. |
| 5,525,632 A | 6/1996 | Obsumi et al. |
| 5,532,129 A | 7/1996 | Heller |
| 5,559,151 A | 9/1996 | Adorante et al. |
| 5,565,191 A | 10/1996 | Raspanti |
| 5,565,322 A | 10/1996 | Heller |
| 5,569,786 A | 10/1996 | Pettit et al. |
| 5,583,128 A | 12/1996 | Bhatnagar |
| 5,589,506 A | 12/1996 | Hashimoto et al. |
| 5,672,625 A | 9/1997 | Cardin et al. |
| 5,674,906 A | 10/1997 | Hatanaka et al. |
| 5,705,530 A | 1/1998 | Adorante et al. |
| 5,716,928 A | 2/1998 | Benet et al. |

(Continued)

FOREIGN PATENT DOCUMENTS

EP 32128 6/1981

(Continued)

OTHER PUBLICATIONS

Lala et al., Role of nitric oxide in tumor progression: Lessons from experimental tumors, Cancer and Metastasis Reviews (1998), 17, 91-106.*

(Continued)

*Primary Examiner*—Kamal A Saeed
*Assistant Examiner*—Kristin Bianchi
(74) *Attorney, Agent, or Firm*—Jones Day

(57) ABSTRACT

Novel diphenylethylene compounds and derivatives thereof containing thiazolidinedione or oxazolidinedione moieties are provided which are effective in lowering blood glucose level, serum insulin, triglyceride and free fatty acid levels in animal models of Type II diabetes. The compounds are disclosed as useful for a variety of treatments including the treatment of inflammation, inflammatory and immunological diseases, insulin resistance, hyperlipidemia, coronary artery disease, cancer and multiple sclerosis.

32 Claims, 26 Drawing Sheets

U.S. PATENT DOCUMENTS

| | | | |
|---|---|---|---|
| 5,731,353 | A | 3/1998 | Ohsumi et al. |
| 5,733,909 | A | 3/1998 | Black et al. |
| 5,767,268 | A | 6/1998 | Chucholowski et al. |
| 5,770,620 | A | 6/1998 | Mjalli et al. |
| 5,804,590 | A | 9/1998 | Fujiwara et al. |
| 5,827,898 | A | 10/1998 | Khandwala et al. |
| 5,972,973 | A | 10/1999 | Whitcomb |
| 5,985,884 | A | 11/1999 | Lohray et al. |
| 5,990,139 | A | 11/1999 | Yano et al. |
| 6,008,237 | A | 12/1999 | Sahoo et al. |
| 6,011,031 | A | 1/2000 | Lohray et al. |
| 6,011,036 | A | 1/2000 | Lohray et al. |
| 6,030,973 | A | 2/2000 | Lohray et al. |
| 6,034,110 | A | 3/2000 | Nagpal et al. |
| 6,046,202 | A | 4/2000 | Antonucci et al. |
| 6,046,222 | A | 4/2000 | Antonucci et al. |
| 6,080,765 | A | 6/2000 | Ikeda et al. |
| 6,103,742 | A | 8/2000 | Ikeda et al. |
| 6,107,323 | A | 8/2000 | Tamura et al. |
| 6,110,948 | A | 8/2000 | Momose et al. |
| 6,110,951 | A | 8/2000 | Pershadsingh et al. |
| 6,114,526 | A | 9/2000 | Lohray et al. |
| 6,117,893 | A | 9/2000 | Fujita et al. |
| 6,121,294 | A | 9/2000 | Ikeda et al. |
| 6,121,295 | A | 9/2000 | Ikeda et al. |
| 6,130,216 | A | 10/2000 | Antonucci et al. |
| 6,133,293 | A | 10/2000 | Ikeda et al. |
| 6,133,295 | A | 10/2000 | Ikeda et al. |
| 6,245,814 | B1 | 6/2001 | Nag et al. |
| 6,331,633 | B1 | 12/2001 | Neogi et al. |
| 6,624,197 | B1 | 9/2003 | Nag et al. |
| 6,730,687 | B1 | 5/2004 | Miyachi et al. |

FOREIGN PATENT DOCUMENTS

| | | |
|---|---|---|
| EP | 1048659 A1 | 11/2000 |

OTHER PUBLICATIONS

Golub et al., Molecular Classification of Cancer: Class Discovery and Class Prediction by Gene Expression Monitoring, Science (1999), vol. 286, 531-537.*

Hulin et al.; Novel Thiazolidine-2,4-diones as Potent Egulycemic Agents, J. Med. Chem.; 1992; 35; 1853-1864.

Sohda et al., "Antiulcer Activity of 5-Benzylthiazolidine-2-4-Dione Derivatives"; Chem. Pharm. Bull.; 31(2) (1983) 560-569.

Giles et al.; "Regiospecific Reduction of 5-Benzylidene-2,4-Thiazolidinediones and 4-Oxo-2-thiazolidinethiones Using Lithium Borohydride in Pyridine and Tetrahydrofuran"; Tetrahedron 56 (26) (2000) 4531-4537.

Myaoka et al.; "Preparation of 2,4-Dioxo-1,2,3,4-Tetrahydroquinazoline Derivatives Having Blood Sugar-Lowering and Aldose Reductase-Inhibiting Activity"; Japan Kokai Tokkyo Koho (1996).

Hulin et al.; "Novel Thiazolidone-2,4-Diones as Patent Euglycemic Agents"; J. Med. Chem.; 35:10 (1992) 1853-1864.

Green, Richard H.; "Syntheses of Differanisole A"; Tetrahedron Letters; 38:26; (1997); 4697-4700.

Reddy et al.; "From Styrenes to Enanitopure α-Arylglycines in Two Steps"; J. Am. Chem. Soc.; 120 (1998) 1207-1217.

Momose et al.; "Studies on Antidiabetic Agents. X.[1)] Synthesis and Biological Activities of Pioglitazone and Related Compounds"; Chem. Pharm. Bull.; 39/(6) (1991) 1440-1445.

Cantello et al.; "[[ω-(Heterocyclylamino)alkoxy]benzyl]-2,4-thiazolidinediones as Potent Antihyperglycemic Agents"; J. Med. Chem.; 37 (1994) 3977-3985.

Sohda et al.; "Studies on Antidiabetic Agents. XII. [1)] Synthesis and Activity of the Metabolites of (±)-5-[p-[2-(5-Ethyl-2-pyridyl)ethoxy]benzyl]-2,4-thiazolidinedione (Pioglitazone)"; Chem. Pharm. Bull.; 43(12) (1995) 2168-2172.

Willson et al.; "The Structure-Activity Relationship between Peroxisome Proliferator-Activated Receptor $y$ Agonism and the Antihyperglycemic Activity of Thiazolidinediones"; J. Med. Chem.; 39 (1996); 665-668.

Tanis et al.; "Synthesis and Biological Activity of Metabolites of the Antidiabetic; Antihyperglycemic Agent Pioglitazone"; J. Med. Chem.; 39 (1996) 5053-5063.

Shinkai et al.; "Isoxazolidine-3,5-dione and Noncyclic 1,3-Dicarbonyl Compounds as Hypoglycemic Agents"; J. Med. Chem.; 41 (1998) 1927-1933.

Lohray et al.; "Novel Euglycemic and Hypolipidemic Agents"; J. Med. Chem.; 41 (1998) 1619-1630.

Reddy et al.; "Novel Antidiabetic and Hypolipidemic Agents. 5. Hydroxyl versus Benzyloxy Containing Chroman Derivatives"; J. Med. Chem.; 42(1999) 3265-3278.

Pettit et al.; "Isolation, Structure, Synthesis and Antimitotic Properties of Combretastatins B-3 and B-4 from Combretum caffrum"; Journal of Natural Products; 51:3 (1988) 517-527.

Turnbow MA, Smith LK, Garner CQ; "The Oxazolidinedione CP-92,768-2 Partially Protects Insulin Receptor Substrate-1 From Dexamethasone Down-Regulationin 3T3-L1 Adipocytes"; Endocrinology; Apr. 1995; 136(4):1450-8.

Yoshioka et al.; Studies on Hindered Phenols and Analogues. 1. Hypolipidemic and Hypoglycemic Agents With Ability to Inhibit Lipid Peroxidation; J. Med. Chem.; Feb. 1989; 32(2):421-8.

Zask et al.; "Synthesis and Antihyperglycemic Activity of Novel 5-(naphthalenylsulfony)-2,4-thiazolidinediones"; J. Med. Chem.; 33:5 (May 1990 ; 1418-23.

Sohda et al.; "Studies on Antidiabetic Agents. 11. Novel thiazolidinedione derivatives as potent hypoglycemic and hypolipidemic agents"; J. Med. Chem.; Jul. 1992; 10:35(14):2617-26.

Hulin et al.; Hypoglycemic activity of a series of alpha-alkyithio and alpha-alkoxy carboxylic acids related to ciglitazone; J. Med.Chem.; Sep. 27, 1996; 39(20):3897-907.

Arakawa et al.; "Novel benzoxazole 2,4-thiazolidinediones as potent hypoglycemic agents. Synthesis and structure-activity relationships"; Chem. Pharm. Bull (Tokyo); Dec. 1997; 45(12):1984-93.

Dow et al.; "Benzyloxazolidine-2,4-diones as Potent Hypoglycemic Agents"; J. Med. Chem.; 1991 vol. 34 1538-1544.

Sohda et al.; "Studies on Antidiabetic Agents. II. Synthesis of 5-[4-(1-Methylcyclohexylmethoxy)-benzyl]thiazolidine-2,4-dione (Add-3878) and Its Derivatives"; Chemical & Pharmaceutical Bulletin 30:10 (Oct. 1982) pp. 3580-3600.

Abstract—Gibbs et al.; "The Benzyloxazolidinedione, CP-92768, is a Potent Antidiabetic Agent In Vivo and In Vitro" Diabetes 42 (Suppl. I) 1993; p. 207A.

* cited by examiner

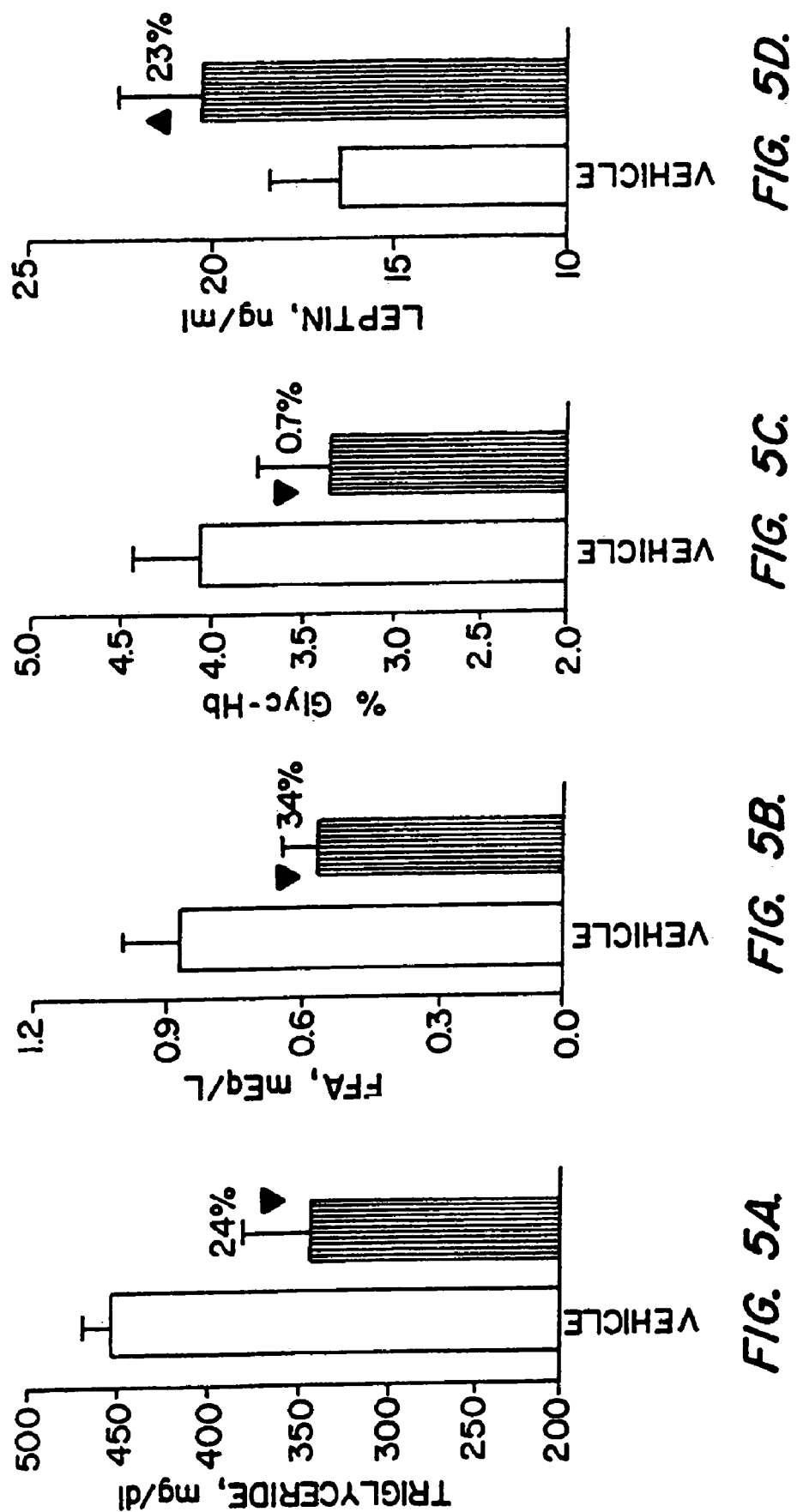

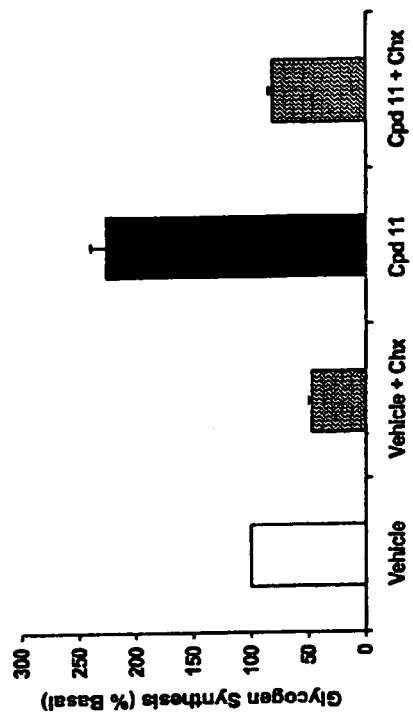
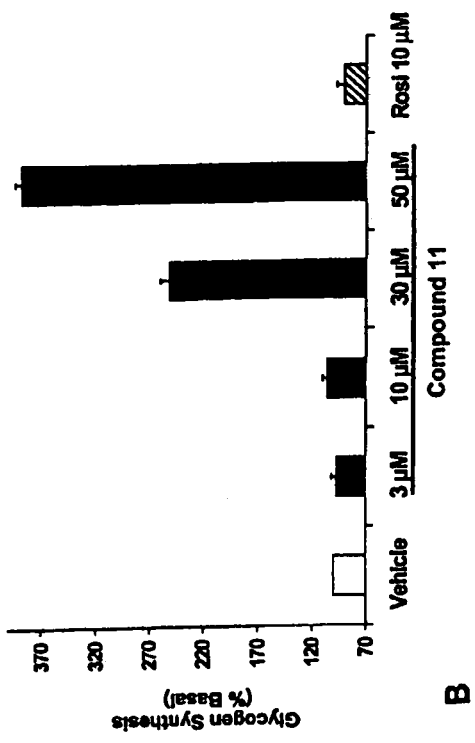
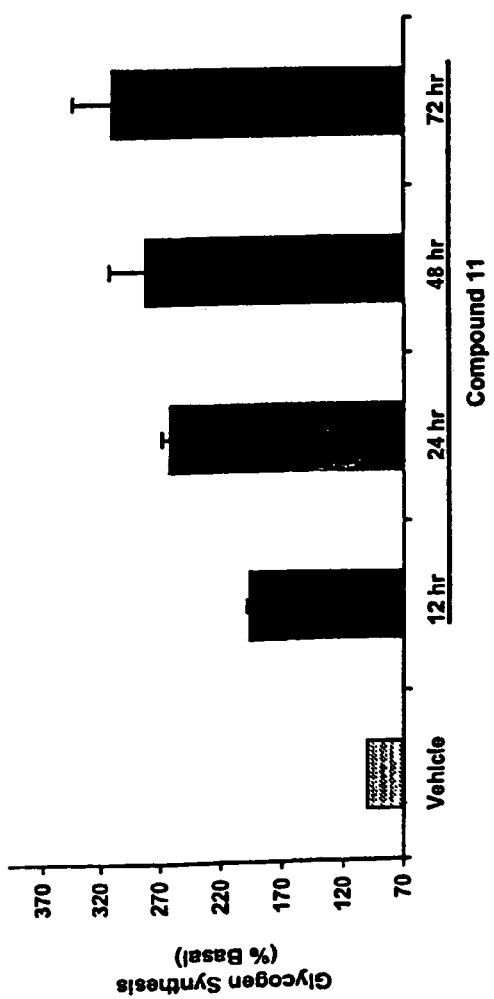
Fig. 25

HETEROCYCLIC ANALOGS OF DIPHENYLETHYLENE COMPOUNDS

CROSS REFERENCE TO RELATED APPLICATIONS

This application is a continuation of application Ser. No. 10/265,902, filed Oct. 8, 2002, which is a continuation-in-part of application Ser. No. 09/843,167, filed Apr. 27, 2001, now U.S. Pat. No. 7,105,552 granted on Sep. 12, 2006, which is a continuation-in-part of application Ser. No. 09/785,554, filed Feb. 20, 2001, now abandoned, which is a continuation-in-part of U.S. patent application Ser. No. 09/591,105, filed on Jun. 9, 2000, now abandoned, which is a continuation-in-part of Ser. No. 09/287,237, filed on Apr. 6, 1999, now U.S. Pat. No. 6,331,633, granted on Dec. 18, 2001. The entire contents of each of these applications is hereby incorporated by reference in their entirety.

BACKGROUND OF THE INVENTION

The present application is directed to novel compounds formed by chemically coupling diphenylethylene compounds and derivatives thereof with thiazolidine or oxazolidine intermediates. These compounds are effective for providing a variety of useful pharmacological effects. For example, the compounds are useful in lowering blood glucose, serum insulin and triglyceride levels in animal models of type II diabetes.

Furthermore, these compounds are useful for treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines and cyclooxygenase such as TNF-alpha, IL-1, IL-6 and/or COX-2.

The causes of type I and type II diabetes are yet unknown, although both genetics and environment seem to be major factors. Insulin dependent type I and non-insulin dependent type II are the types which are known. Type I is an autoimmune disease in which the responsible autoantigen is still unknown. Patients of type I need to take insulin parenterally or subcutaneously to survive. However, type II diabetes, the more common form, is a metabolic disorder resulting from the body's inability to make a sufficient amount of insulin or to properly use the insulin that is produced. Insulin secretion and insulin resistance are considered the major defects, however, the precise genetic factors involved in the mechanism remain unknown.

Patients with diabetes usually have one or more of the following defects:
  Less production of insulin by the pancreas;
  Over secretion of glucose by the liver;
  Decreased glucose uptake by the skeletal muscles;
  Defects in glucose transporters; and
  Desensitization of insulin receptors.

Other than the parenteral or subcutaneous application of insulin, there are about 4 classes of oral hypoglycemic agents used.

TABLE 1

| Class | Approved Drugs | Mode of Action | Limitations |
|---|---|---|---|
| Sulfonylurea | 4 (1$^{st}$ generation) and 2 (2$^{nd}$ generation) | Acts on pancreas to release more insulin | development of resistance |

TABLE 1-continued

| Class | Approved Drugs | Mode of Action | Limitations |
|---|---|---|---|
| Biguanides | Metformin | Reduces glucose production by liver; improves insulin sensitivity | liver problems, lactic acidosis |
| Alpha'-glucosidase inhibitor | Acarbose | Interferes with digestive process; reduces glucose absorption | only useful at postprandial level |
| Thiazolidinedione | Troglitazone (withdrawn) Rosiglitazone Pioglitazone | Reduce insulin resistancy | "add-on" with insulin; not useful for people with heart and liver disease |

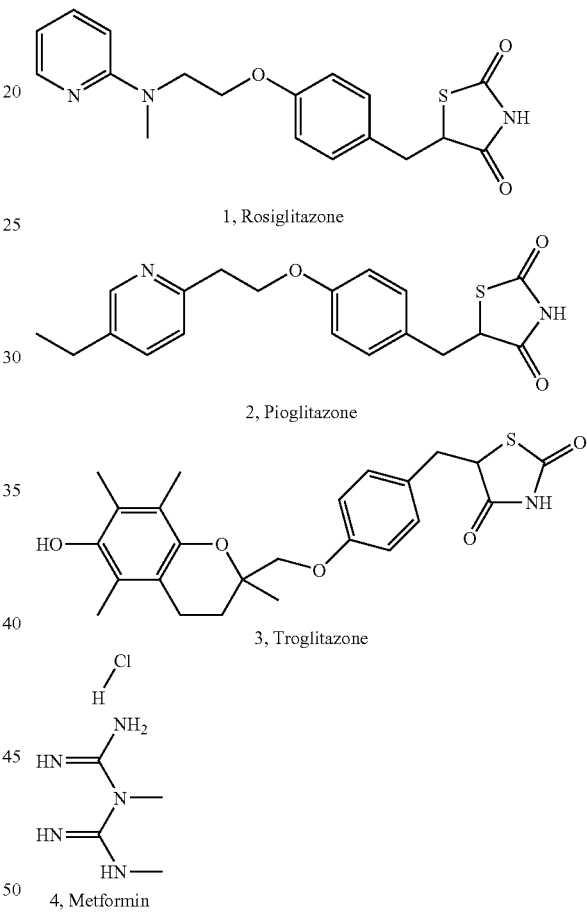

1, Rosiglitazone

2, Pioglitazone

3, Troglitazone

4, Metformin

As is apparent from the above table, each of the current agents available for use in treatment of diabetes has certain disadvantages. Accordingly, there is a continuing interest in the identification and development of new agents, particularly, water soluble agents which can be orally administered, for use in the treatment of diabetes.

The thiazolidinedione class listed in the above table has gained more widespread use in recent years for treatment of type II diabetes, exhibiting particular usefulness as insulin sensitizers to combat "insulin resistance", a condition in which the patient becomes less responsive to the effects of insulin. However, the known thiazolidinediones are not effective for a significant portion of the patient population. In addition, the first drug in this class to be approved by the FDA, troglitazone, was withdrawn from the market due to problems of liver toxicity. Thus, there is a continuing need for nontoxic, more widely effective insulin sensitizers. Pharmaceutical compositions and methods utilizing thiazolidinediones are described in U.S. Pat. Nos. 6,133,295; 6,133,293; 6,130,216; 6,121,295; 6,121,294; 6,117,893; 6,114,526; 6,110,951; 6,110,948; 6,107,323; 6,103,742; 6,080,765; 6,046,222; 6,046,202; 6,034,110; 6,030,973; RE36,575; 6,011,036; 6,011,031; 6,008,237; 5,990,139; 5,985,884; 5,972,973 and others.

As indicated above, the present invention is also concerned with treatment of immunological diseases or inflammation, notably such diseases as are mediated by cytokines or cyclooxygenase. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and providing the necessary "help" for T cell stimulation and proliferation. Most importantly macrophages make IL 1, IL 12 and TNF-alpha, all of which are potent pro-inflammatory molecules and also provide help for T cells. In addition, activation of macrophages results in the induction of enzymes, such as cyclooxygenase II (COX-2), inducible nitric oxide synthase (NOS) and production of free radicals capable of damaging normal cells. Many factors activate macrophages, including bacterial products, superantigens and interferon gamma (IFNγ). It is believed that phosphotyrosine kinases (PTKs) and other undefined cellular kinases are involved in the activation process.

Macrophages take up and break down antigens into small fragments. These fragments then associate with the major histocompatibility complex II (MHC II). This complex of antigen fragments and MHC II is recognized by the T cell receptor. In association with appropriate co-stimulatory signals this receptor-ligand interaction leads to the activation and proliferation of T cells. Depending on the route of administration of antigen, their dose and the conditions under which macrophages are activated, the immune response can result in either B cell help and antibody production or on the development of cell mediated response. Since macrophages are sentinel to the development of an immune response, agents that modify their function, specifically their cytokine secretion profile, are likely to determine the direction and potency of the immune response.

Cytokines are molecules secreted by immune cells that are important in mediating immune responses. Cytokine production may lead to the secretion of other cytokines, altered cellular function, cell division or differentiation. Inflammation is the body's normal response to injury or infection. However, in inflammatory diseases such as rheumatoid arthritis, pathologic inflammatory processes can lead to morbidity and mortality. The cytokine tumor necrosis factor-alpha (TNF-alpha) plays a central role in the inflammatory response and has been targeted as a point of intervention in inflammatory disease. TNF-alpha is a polypeptide hormone released by activated macrophages and other cells. At low concentrations, TNF-alpha participates in the protective inflammatory response by activating leukocytes and promoting their migration to extravascular sites of inflammation (Moser et al., J Clin Invest, 83:444-55, 1989). At higher concentrations, TNF-alpha can act as a potent pyrogen and induce the production of other pro-inflammatory cytokines (Haworth et al., Eur J Immunol, 21:2575-79, 1991; Brennan et al., Lancet, 2:244-7, 1989). TNF-alpha also stimulates the synthesis of acute-phase proteins. In rheumatoid arthritis, a chronic and progressive inflammatory disease affecting about 1% of the adult U.S. population, TNF-alpha mediates the cytokine cascade that leads to joint damage and destruction (Arend et al., Arthritis Rheum, 38:151-60, 1995). Inhibitors of TNF-alpha, including soluble TNF receptors (etanercept) (Goldenberg, Clin Ther, 21:75-87, 1999) and anti-TNF-alpha antibody (infliximab) (Luong et al., Ann Pharmacotherapy, 34:743-60, 2000), have recently been approved by the U.S. Food and Drug Administration (FDA) as agents for the treatment of rheumatoid arthritis.

Elevated levels of TNF-alpha have also been implicated in many other disorders and disease conditions, including cachexia (Fong et al., Am J Physiol, 256:8659-65, 1989), septic shock syndrome (Tracey et al., Proc Soc Exp Biol Med, 200:233-9, 1992), osteoarthritis (Venn et al., Arthritis Rheum, 36:819-26, 1993), inflammatory bowel disease such as Crohn's disease and ulcerative colitis (Murch et al., Gut, 32:913-7, 1991), Behcet's disease (Akoglu et al., J Rheumatol, 17:1107-8, 1990), Kawasaki disease (Matsubara et al., Clin Immunol Immunopathol, 56:29-36, 1990), cerebral malaria (Grau et al., N Engl J Med, 320:1586-91, 1989), adult respiratory distress syndrome (Millar et al., Lancet 2:712-4, 1989), asbestosis and silicosis (Bissonnette et al., Inflammation, 13:329-39, 1989), pulmonary sarcoidosis (Baughman et al., J Lab Clin Med, 115:36-42, 1990), asthma (Shah et al., Clin Exp Allergy, 25:1038-44, 1995), AIDS (Dezube et al., J Acquir Immune Defic Syndr, 5:1099-104, 1992), meningitis (Waage et al., Lancet, 1:355-7, 1987), psoriasis (Oh et al., J Am Acad Dermatol, 42:829-30, 2000), graft versus host reaction (Nestel et al., J Exp Med, 175:405-13, 1992), multiple sclerosis (Sharief et al., N Engl J Med, 325:467-72, 1991), systemic lupus erythematosus (Maury et al., Int Tissue React, 11:189-93, 1989), diabetes (Hotamisligil et al., Science, 259: 87-91, 1993) and atherosclerosis (Bruunsgaard et al., Clin Exp Immunol, 121:255-60, 2000).

It can be seen from the references cited above that inhibitors of TNF-alpha are potentially useful in the treatment of a wide variety of diseases. Compounds that inhibit TNF-alpha have been described in U.S. Pat. Nos. 6,090,817; 6,080,763; 6,080,580; 6,075,041; 6,057,369; 6,048,841; 6,046,319; 6,046,221; 6,040,329; 6,034,100; 6,028,086; 6,022,884; 6,015,558; 6,004,974; 5,990,119; 5,981,701; 5,977,122; 5,972,936; 5,968,945; 5,962,478; 5,958,953; 5,958,409; 5,955,480; 5,948,786; 5,935,978; 5,935,977; 5,929,117; 5,925,636; 5,900,430; 5,900,417; 5,891,883; 5,869,677 and others.

Interleukin-6 (IL-6) is another pro-inflammatory cytokine that exhibits pleiotropy and redundancy of action. IL-6 participates in the immune response, inflammation and hematopoiesis. It is a potent inducer of the hepatic acute phase response and is a powerful stimulator of the hypothalamic-pituitary-adrenal axis that is under negative control by glucocorticoids. IL-6 promotes the secretion of growth hormone but inhibits release of thyroid stimulating hormone. Elevated levels of IL-6 are seen in several inflammatory diseases, and inhibition of the IL-6 cytokine subfamily has been suggested as a strategy to improve therapy for rheumatoid arthritis (Carroll et al., Inflamm Res, 47:1-7, 1998). In addition, IL-6 has been implicated in the progression of atherosclerosis and the pathogenesis of coronary heart disease (Yudkin et al., Atherosclerosis, 148:209-14, 1999). Overproduction of IL-6 is also seen in steroid withdrawal syndrome, conditions related to deregulated vasopressin secretion, and osteoporosis associated with increased bone resorption, such as in cases of hyperparathyroidism and sex-steroid deficiency (Papanicolaou et al., Ann Intern Med, 128:127-37, 1998).

Since excessive production of IL-6 is implicated in several disease states, it is highly desirable to develop compounds that inhibit IL-6 secretion. Compounds that inhibit IL-6 have been described in U.S. Pat. Nos. 6,004,813; 5,527,546 and 5,166,137.

Cyclooxygenase is an enzyme that catalyzes a rate-determining step in the biosynthesis of prostaglandins, which are important mediators of inflammation- and pain. The enzyme occurs as at least two distinct isomers, cyclooxygenase-1 (COX-1) and cyclooxygenase-2 (COX-2). The COX-1 isomer is constitutively expressed in the gastric mucosa, platelets and other cells and is involved in the maintenance of homeostasis in mammals, including protecting the integrity of the digestive tract. The COX-2 isomer, on the other hand, is not constitutively expressed but rather is induced by various agents, such as cytokines, mitogens, hormones and growth factors. In particular, COX-2 is induced during the inflammatory response (DeWitt D L, Biochim Biophys Acta, 1083: 121-34, 1991; Seibert et al., Receptor, 4:17-23, 1994.). Aspirin and other conventional non-steroid anti-inflammatory drugs (NSAIDs) are non-selective inhibitors of both COX-1 and COX-2. They can be effective in reducing inflammatory pain and swelling, but since they hamper the protective action of COX-1, they produce undesirable side effects of gastrointestinal pathology. Therefore, agents that selectively inhibit COX-2 but not COX-1 are preferable for treatment of inflammatory diseases. Recently, a diarylpyrazole sulfonamide (celecoxib) that selectively inhibits COX-2 has been approved by the FDA for use in the treatment of rheumatoid arthritis (Luong et al., Ann Pharmacother, 34:743-60, 2000; Penning et al., J Med Chem, 40:1347-65, 1997). COX-2 is also expressed in many cancers and precancerous lesions, and there is mounting evidence that selective COX-2 inhibitors may be useful for treating and preventing colorectal, breast and other cancers (Taketo M M, J Natl Cancer Inst, 90:1609-20, 1998; Fournier et al., J Cell Biochem Suppl, 34:97-102, 2000; Masferrer et al., Cancer Res, 60:1306-11, 2000). In 1999 celecoxib was approved by the FDA as an adjunct to usual care for patients with familial adenomatous polyposis, a condition which, left untreated, generally leads to colorectal cancer.

Compounds that selectively inhibit COX-2 have been described in U.S. Pat. Nos. 5,344,991; 5,380,738; 5,434,178; 5,466,823; 5,474,995; 5,510,368; 5,521,207; 5,521,213; 5,536,752; 5,550,142; 5,552,422; 5,604,260; 5,639,780; 5,643,933; 5,677,318; 5,691,374; 5,698,584; 5,710,140; 5,733,909; 5,789,413; 5,811,425; 5,817,700; 5,849,943; 5,859,257; 5,861,419; 5,905,089; 5,922,742; 5,925,631; 5,932,598; 5,945,539; 5,968,958; 5,981,576; 5,994,379; 5,994,381; 6,001,843; 6,002,014; 6,004,950; 6,004,960; 6,005,000; 6,020,343; 6,034,256; 6,046,191; 6,046,217; 6,057,319; 6,071,936; 6,071,954; 6,077,850; 6,077,868; 6,077,869 and 6,083,969.

The cytokine IL-1 beta also participates in the inflammatory response. It stimulates thymocyte proliferation, fibroblast growth factor activity, and the release of prostaglandin from synovial cells.

Elevated or unregulated levels of the cytokine IL-1 beta have been associated with a number of inflammatory diseases and other disease states, including but not limited to adult respiratory distress syndrome (Meduri et al, Chest 107:1062-73, 1995), allergy (Hastie et al, Cytokine 8:730-8, 1996), Alzheimer's disease (O'Barr et al, J Neuroimmunol 109:87-94, 2000), anorexia (Laye et al, Am J Physiol Regul Integr Comp Physiol 279:893-8, 2000), asthma (Sousa et al, Thorax 52:407-10, 1997), atherosclerosis (Dewberry et al, Arterioscler Thromb Vasc Biol 20:2394-400, 2000), brain tumors (Ilyin et al, Mol Chem Neuropathol 33:125-37, 1998), cachexia (Nakatani et al, Res Commun Mol Pathol Pharmacol 102:241-9, 1998), carcinoma (Ikemoto et al, Anticancer Res 20:317-21, 2000), chronic arthritis (van den Berg et al, Clin Exp Rheumatol 17:S105-14, 1999), chronic fatigue syndrome (Cannon et al, J Clin Immunol 17:253-61, 1997), CNS trauma (Herx et al, J Immunol 165:2232-9, 2000), epilepsy (De Simoni et al, Eur J Neurosci 12:2623-33, 2000), fibrotic lung diseases (Pan et al, Pathol Int 46:91-9, 1996), fulminant hepatic failure (Sekiyama et al, Clin Exp Immunol 98:71-7, 1994), gingivitis (Biesbrock et al, Monogr Oral Sci 17:20-31, 2000), glomerulonephritis (Kluth et al, J Nephrol 12:66-75, 1999), Guillain-Barre syndrome (Zhu et al, Clin Immunol Immunopathol 84:85-94, 1997), heat hyperalgesia (Opree et al, J Neurosci 20:6289-93, 2000), hemorrhage and endotoxemia (Parsey et al, J Immunol 160:1007-13, 1998), inflammatory bowel disease (Olson et al, J Pediatr Gastroenterol Nutr 16:241-6, 1993), leukemia (Estrov et al, Leuk Lymphoma 24:379-91, 1997), leukemic arthritis (Rudwaleit et al, Arthritis Rheum 41:1695-700, 1998), systemic lupus erythematosus (Mao et al, Autoimmunity 24:71-9, 1996), multiple sclerosis (Martin et al, J Neuroimmunol 61:241-5, 1995), osteoarthritis (Hernvann et al, Osteoarthritis Cartilage 4:13942, 1996), osteoporosis (Zheng et al, Maturitas 26:63-71, 1997), Parkinson's disease (Bessler et al, Biomed Pharmacother 53:141-5, 1999), POEMS syndrome (Gherardi et al, Blood 83:2587-93, 1994), pre-term labor (Dudley, J Reprod Immunol 36:93-109, 1997), psoriasis (Bonifati et al, J Biol Regul Homeost Agents 11:133-6, 1997), reperfusion injury (Clark et al, J Surg Res 58:675-81, 1995), rheumatoid arthritis (Seitz et al, J Rheumatol 23:1512-6, 1996), septic shock (van Deuren et al, Blood 90:1101-8, 1997), systemic vasculitis (Brooks et al, Clin Exp Immunol 106:273-9, 1996), temporal mandibular joint disease (Nordahl et al, Eur J Oral Sci 106:559-63, 1998), tuberculosis (Tsao et al, Tuber Lung Dis 79:279-85, 1999), viral rhinitis (Roseler et al, Eur Arch Otorhinolaryngol Suppl 1:S61-3, 1995), and pain and/or inflammation resulting from strain, sprain, trauma, surgery, infection or other disease processes.

Since overproduction of IL-1 beta is associated with numerous disease conditions, it is desirable to develop compounds that inhibit the production or activity of IL-1 beta. Methods and compositions for inhibiting IL-1 beta are described in U.S. Pat. Nos. 6,096,728; 6,090,775; 6,083,521; 6,036,978; 6,034,107; 6,034,100; 6,027,712; 6,024,940; 5,955,480; 5,922,573; 5,919,444; 5,905,089; 5,874,592; 5,874,561; 5,874,424; 5,840,277; 5,837,719; 5,817,670; 5,817,306; 5,792,778; 5,780,513; 5,776,979; 5,776,954; 5,767,064; 5,747,444; 5,739,282; 5,731,343; 5,726,148; 5,684,017; 5,683,992; 5,668,143; 5,624,931; 5,618,804; 5,527,940; 5,521,185; 5,492,888; 5,488,032 and others.

It will be appreciated from the foregoing that, while there have been extensive prior efforts to provide compounds for inhibiting, for example, TNF-alpha, IL-1, IL-6, COX-2 or other agents considered responsible for immune response, inflammation or inflammatory diseases, e.g. arthritis, there still remains a need for new and improved compounds for effectively treating or inhibiting such diseases. A principal object of the invention is to provide compounds which are effective for such treatments as well as for the treatment of, for example, insulin resistance, hyperlipidemia, coronary heart disease, multiple sclerosis and cancer.

SUMMARY OF THE INVENTION

In one aspect of the invention, compounds of the following formula 1 are provided:

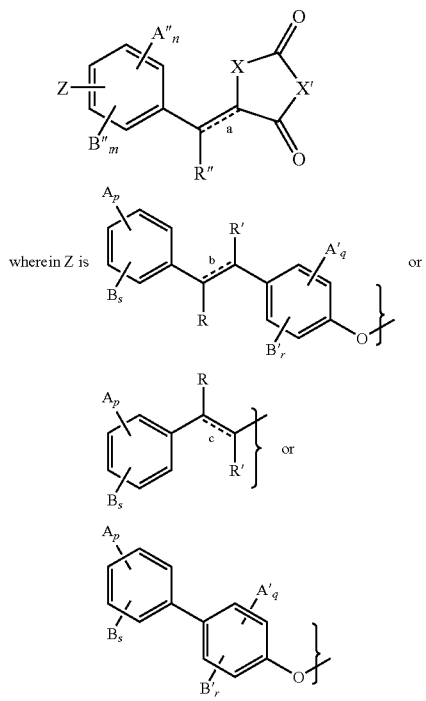

Formula 1 wherein n, m, q and r are independently integers from zero to 4 provided that $n+m \leq 4$, and $q+r \leq 4$; p and s are independently integers from zero to 5 provided that $p+s \leq 5$; a, b and c are double bonds which may be present or absent; when present, the double bonds may be in the E or Z configuration and, when absent, the resulting stereocenters can have the R- or S-configuration;

R and R' are independently H, $C_1$-$C_{20}$ linear or branched alkyl, $C_2$-$C_{20}$ linear or branched alkenyl, —$CO_2Z'$, wherein Z' is H, sodium, potassium, or other pharmaceutically acceptable counter-ion such as calcium, magnesium, ammonium, tromethamine, tetramethylammonium, and the like; —$CO_2R'''$, —$NH_2$, —$NHR'''$, —$NR_2'''$, —OH, —$OR'''$, halo, substituted $C_1$-$C_{20}$ linear or branched alkyl or substituted $C_2$-$C_{20}$ linear or branched alkenyl, wherein R''' is independently $C_1$-$C_{20}$ linear or branched alkyl, linear or branched alkenyl or aralkyl —$(CH_2)_x$—Ar, where x is 1-6; $CONR_2''''$, where R'''' is independently H, optionally substituted $C_1$-$C_{20}$ alkyl, optionally substituted $C_2$-$C_{20}$ alkenyl or optionally substituted $C_6$-$C_{10}$ aryl or where $NR_2$ " " represents a cyclic moiety such as morpholine, piperidine, piperazine and the like;

R" is independently H, $C_1$-$C_{20}$ linear or branched alkyl, $C_2$-$C_{20}$ linear or branched alkenyl, —$CO_2Z'$, wherein Z' is H, sodium, potassium, or other pharmaceutically acceptable counter-ion such as calcium, magnesium, ammonium, tromethamine, tetramethylammonium, and the like; —$CO_2R'''$, —$NH_2$, —$NHR'''$, —$NR_2'''$, —OH, —$OR'''$, halo, substituted $C_1$-$C_{20}$ linear or branched alkyl or substituted $C_2$-$C_{20}$ linear or branched alkenyl wherein R''' is independently $C_1$-$C_{20}$ linear or branched alkyl, linear or branched alkenyl or aralkyl —$(CH_2)_x$—Ar, where x is 1-6;

A, A' and A" are independently H, $C_1$-$C_{20}$ acylamino; $C_1$-$C_{20}$ acyloxy; $C_1$-$C_{20}$ alkanoyl; $C_1$-$C_{20}$ alkoxycarbonyl; $C_1$-$C_{20}$ alkoxy; $C_1$-$C_{20}$ alkylamino; $C_1$-$C_{20}$ alkylcarboxylamino; carboxyl; cyano; halo; hydroxy;

B, B' and B" are independently H; $C_1$-$C_{20}$ acylamino; $C_1$-$C_{20}$ acyloxy; $C_1$-$C_{20}$ alkanoyl; $C_1$-$C_{20}$ alkenoyl; $C_1$-$C_{20}$ alkoxycarbonyl; $C_1$-$C_{20}$ alkoxy; $C_1$-$C_{20}$ alkylamino; $C_1$-$C_{20}$ alkylcarboxylamino; aroyl, aralkanoyl; carboxyl; cyano; halo; hydroxy; nitro; optionally substituted, linear or branched $C_1$-$C_{20}$ alkyl or $C_2$-$C_{20}$ alkenyl; or A and B together, or A' and B' together, or A" and B" together, may be joined to form a methylenedioxy or ethylenedioxy group;

X, X' are independently —NH, —NR''', O or S.

These compounds are useful for treating diabetes, hyperlipidemia and other diseases linked to insulin resistance, such as coronary artery disease and peripheral vascular disease, and also for treating or inhibiting inflammation or inflammatory diseases such as inflammatory arthritis and collagen vascular diseases, which are caused by, for example, cytokines or cyclooxygenase such as TNF-alpha, IL-1, IL-6 and/or COX-2. The compounds are also useful for treating or preventing other diseases mediated by cytokines and/or cyclooxygenase, such as cancer.

Accordingly, the invention also provides a method of treating diabetes and related diseases comprising the step of administering to a subject suffering from a diabetic or related condition a therapeutically effective amount of a compound of formula 1. Additionally, the invention provides a method of treating inflammation or inflammatory diseases or diseases mediated by cytokines and/or cyclooxygenase by administering to a subject in need of such treatment an effective amount of a compound according to Formula 1. Other uses will also be evident from this specification.

Pharmaceutical compositions containing a therapeutically effective amount of one or more compounds according to formula 1 together with a pharmaceutically or physiologically acceptable carrier, for use in the treatments contemplated herein, are also provided.

BRIEF DESCRIPTION OF THE DRAWINGS

FIGS. 5A, 5B, 5C and 5D show graphs of the triglyceride levels, free fatty acid levels, glyc-Hb levels and leptin levels in serum of the db/db mice treated with a compound according to the present invention.

FIG. 25. Effect of Compound 11 on In Vitro Glycogen Synthesis in HepG2 Cells. A. Dose-dependent stimulation of glycogen synthesis from glucose by Compound 11 in the absence of insulin. B. Time-dependent increase in Compound 11-stimulated glycogen synthesis. C. Cycloheximide blocks glycogen synthesis induced by Compound 11.

DESCRIPTION OF THE PREFERRED EMBODIMENTS

Figure 1B:
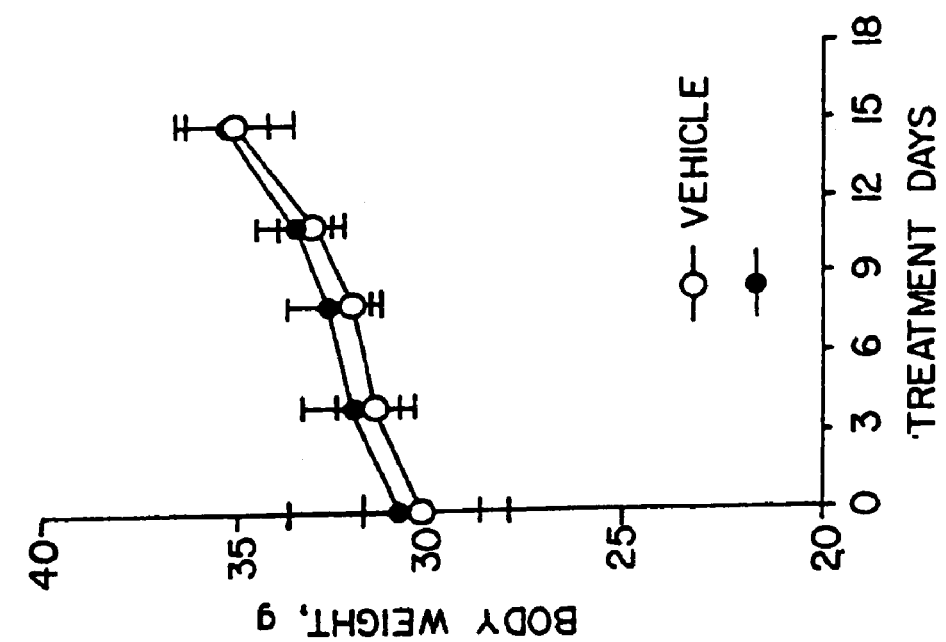
FIGS. 1A and 1B show graphs of the blood glucose levels and body weights, respectively, of db/db (spontaneous diabetic) male mice given a compound according to the invention of a period of 15 days.

A preferred compound according to formula 1 is 5-(4-(4-(1 carbomethoxy-2-(3,5-dimethoxyphenyl)-ethenyl)-phenoxy)-benzyl)-2,4-thiazolidinedione, hereinafter referred to as compound 11. However, it will be appreciated that the invention also contemplates the provision and use of other compounds according to formula 1.

The compounds according to the present invention may be combined with a physiologically acceptable carrier or vehicle to provide a pharmaceutical composition, such as, lyophilized powder in the form of tablet or capsule with various fillers and binders. The effective dosage of a compound in the composition can be widely varied as selected by those of ordinary skill in the art and may be empirically determined.

As earlier indicated, the compounds of the invention are useful for the treatment of diabetes, characterized by the presence of elevated blood glucose levels, that is, hyperglycemic disorders such as diabetes mellitus, including both type I and II diabetes, as well as other hyperglycemic related disorders such as obesity, increased cholesterol, hyperlipidemia such as hypertriglyceridemia, kidney related disorders and the like. The compounds are also useful for the treatment of disorders linked to insulin resistance and/or hyperinsulinemia, which include, in addition to diabetes, hyperandrogenic conditions such as polycystic ovary syndrome (Ibanez et al., J. Clin Endocrinol Metab, 85:3526-30, 2000; Taylor A. E., Obstet Gynecol Clin North Am, 27:583-95, 2000), coronary artery disease such as atherosclerosis and vascular restenosis, and peripheral vascular disease. Additionally, the compounds of the present invention are also useful for the treatment of inflammation and immunological diseases that include those mediated by signaling pathways linked to pro-inflammatory cytokines, such as rheumatoid arthritis and other inflammatory arthritis, multiple sclerosis, inflammatory bowel disease, psoriasis, psoriatic arthritis, ankylosing spondylitis and other spondylarthritides, and contact and atopic dermatitis.

By "treatment", it is meant that the compounds of the invention are administered in an amount which is at least sufficient to, for example, reduce the blood glucose level in a patient suffering from hyperglycemic disorder or to inhibit or prevent the development of pro-inflammatory cytokine or like responses in a patient suffering from inflammatory or immunological disease. In the case of diabetes, the compound is usually administered in the amount sufficient to reduce the blood glucose level, free fatty acid level, cholesterol level, and the like to an acceptable range, where an acceptable range means + or −10%, and usually + or −5% of the normal average blood glucose level and like level of the subject, or sufficient to alleviate the symptoms and/or reduce the risk of complications associated with elevated levels of these parameters. A variety of subjects may be treated with the present compounds to reduce blood glucose levels such as livestock, wild or rare animals, pets, as well as humans. The compounds may be administered to a subject suffering from hyperglycemic disorder using any convenient administration technique, including intravenous, intradermal, intramuscular, subcutaneous, oral and the like. However, oral daily dosage is preferred. The dosage delivered to the host will necessarily depend upon the route by which the compound is delivered, but generally ranges from about 0.1-500 mg/kg human body weight or typically from about 1 to 50 mg/kg human body weight. Generally similar types of administration and dosages are also contemplated when the compounds of the invention are used to treat inflammatory or immunological disease.

The compounds of this invention may be used in formulations using acceptable pharmaceutical vehicles for enteral, or parenteral, administration, such as, for example, water, alcohol, gelatin, gum arabic, lactose, amylase, magnesium stearate, talc, vegetable oils, polyalkylene glycol, and the like. The compounds can be formulated in solid form, e.g., as tablets, capsules, drages and suppositories, or in the liquid form, e.g., solutions, suspensions and emulsions. The preparations may also be delivered transdermally or by topical application.

Representative compounds according to the present invention may be synthesized by the methods disclosed below in Schemes 1 through 11, wherein Scheme 1 illustrates the preparation of exemplary compounds 10, 11 and 14; Scheme 2 illustrates the preparation of exemplary compounds 17 and 18; Scheme 3 illustrates the preparation of exemplary compounds 22 and 23; Scheme 6 illustrates the synthesis of exemplary compounds 40, 41 and 42; Scheme 7 illustrates the preparation of exemplary compounds 46, 47, 49 and 50; Scheme 8 illustrates the synthesis of compound 54; Scheme 9 illustrates the preparation of compounds 58 and 59; and Schemes 4, 5, 10 and 11 describe the synthesis methods more generally.

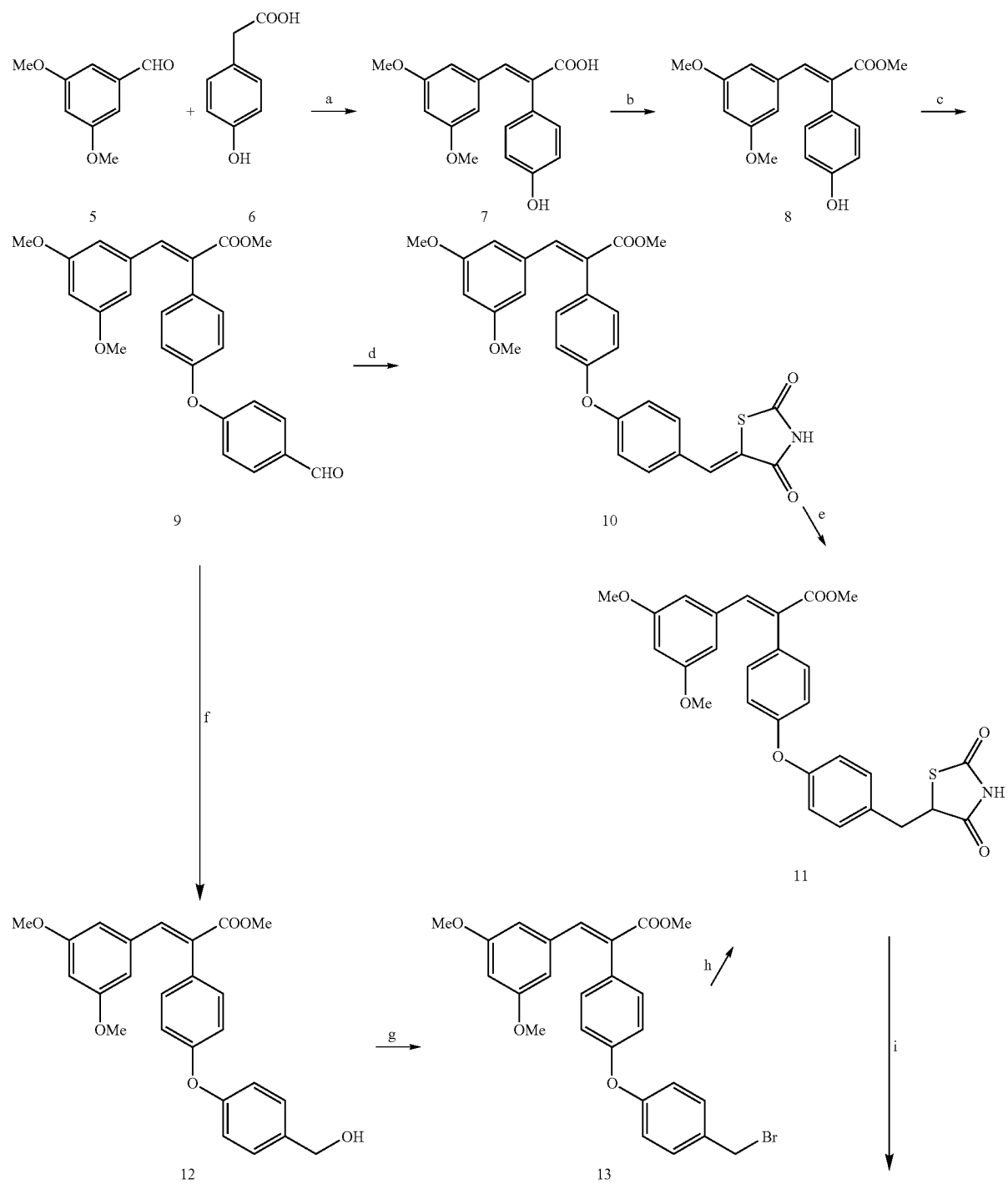

SCHEME 1

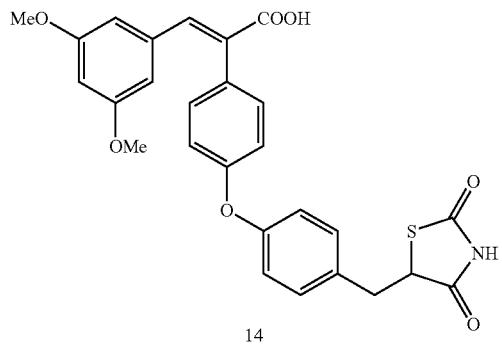

14

*Reagents and conditions: (a) acetic anhydride, Et₃N, 6 h, 130° C., 47%; (b) MeOH, H₂SO₄, 20 h, reflux, 97%; (c) 4-fluorobenzaldehyde, NaH, DMF, 18 h, 80° C., 77%; (d) 2,4-thiazolidinedione, piperidine, benzoic acid, toluene, 5 h, reflux, 86%; (e) Pd/C (10%), HCOONH₄/AcOH, 48 h, reflux, 49%; (f) NaBH₄, EtOH, 1 h, 25° C., quantitative; (g) PBr₃, CH₂Cl₂, 25° C., 1 h, 99%; (h) BuLi, 2,4-thiazolidinedione, THF, 0° C., 45 min, 15%; (i) aqueous NaOH, MeOH, 15 h, 25° C., 73%.

SCHEME 2

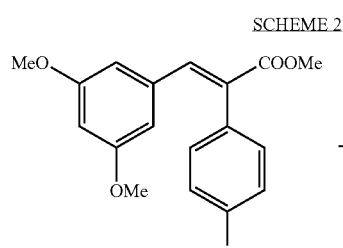

8

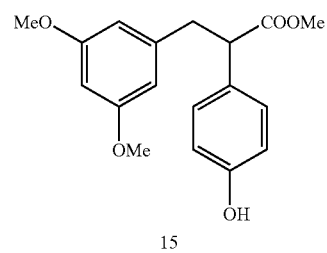

15

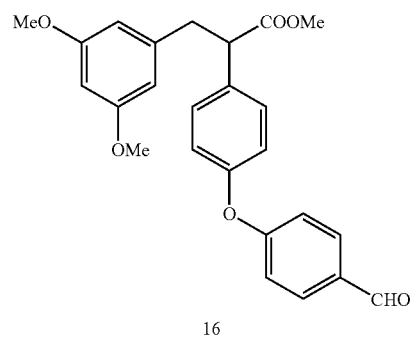

16

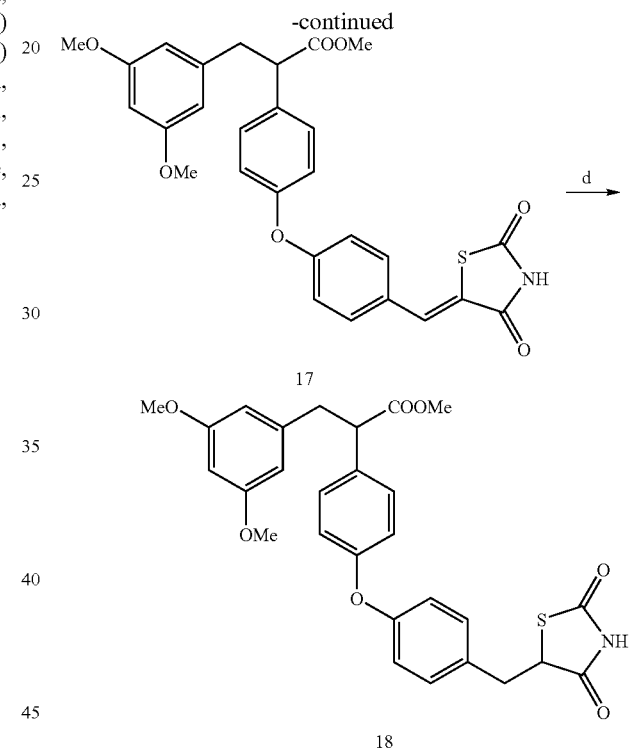

*Reagents and conditions: (a) Pd/C (10%), H₂, 18 h, 25° C., quantitative; (b) 4-fluorobenzaldehyde, NaH, DMF, 18 h, 80° C., 69%; (c) 2,4-thiazolidinedione, piperidine, benzoic acid, toluene, 2 h, reflux, 81%; (d) Pd/C (10%), H₂ (60 psi), 34 h, 25° C., 38%.

SCHEME 3

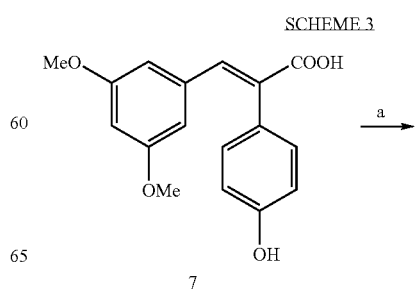

7

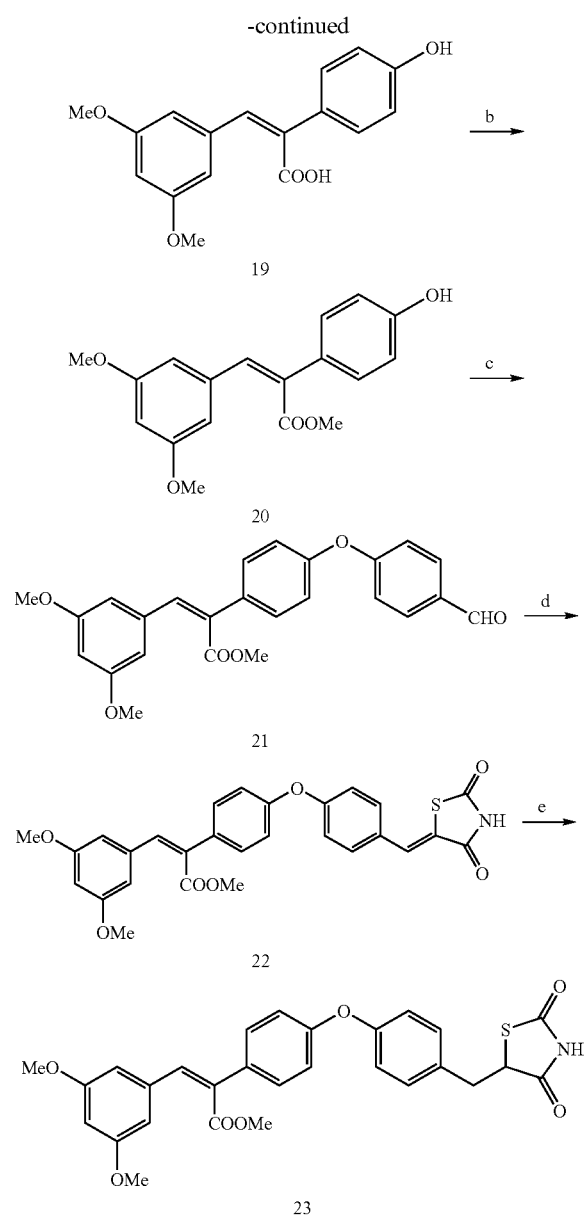
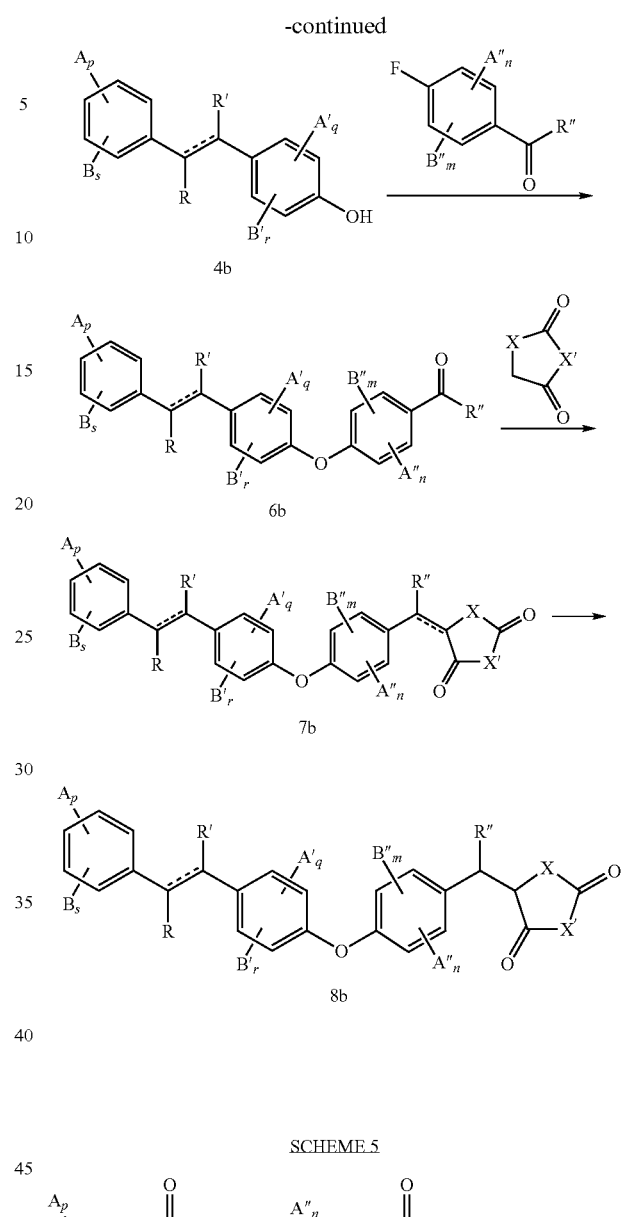
*a*Reagents and conditions: (a) acetic anhydride, Et₃N, 24 h, 125° C., 13%,; (b) MeOH, H₂SO₄, 18 h, reflux, 35%; (c) 4-fluorobenzaldehyde, NaH, DMF, 18 h, 80° C., 74%; (d) 2,4-thiazolidinedione, piperidine, benzoic acid, toluene, 5 h, reflux, 91%; (e) Pd/C (10%), ammonium formate, acetic acid, 20 h, reflux.
SCHEME 4
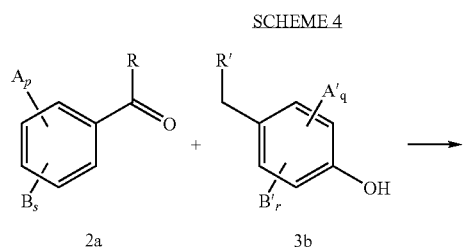
SCHEME 5
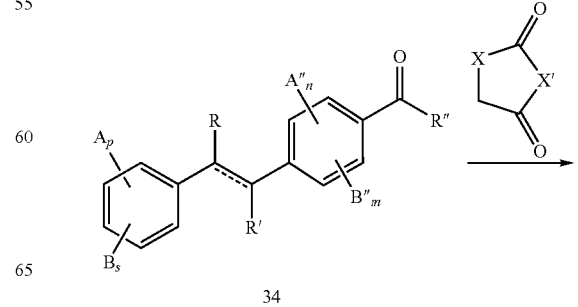

-continued
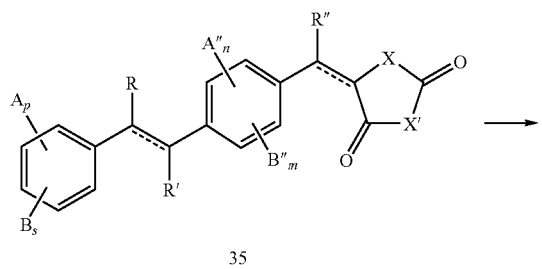
35
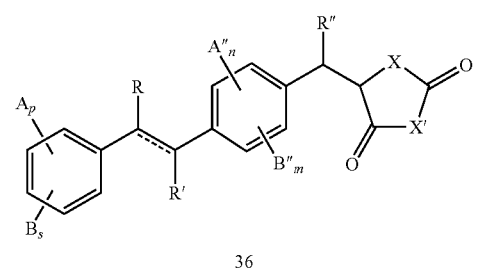
36
SCHEME 6
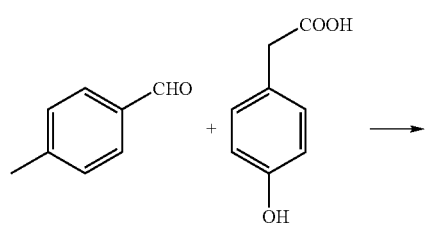
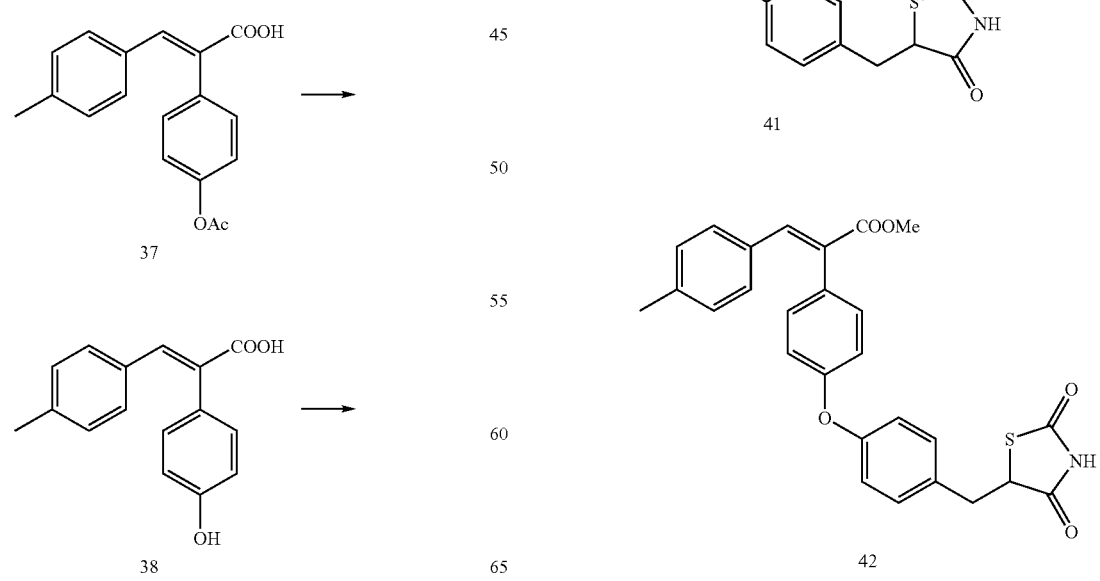
-continued
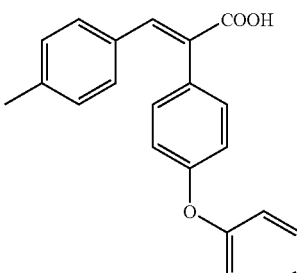
39
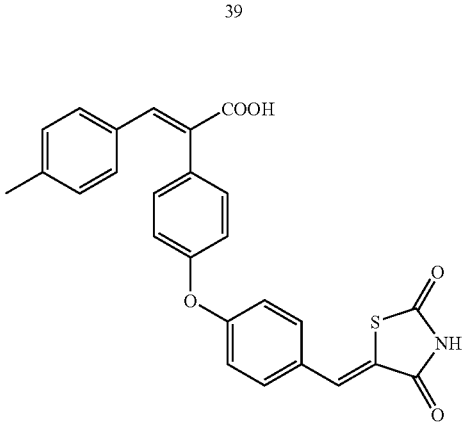

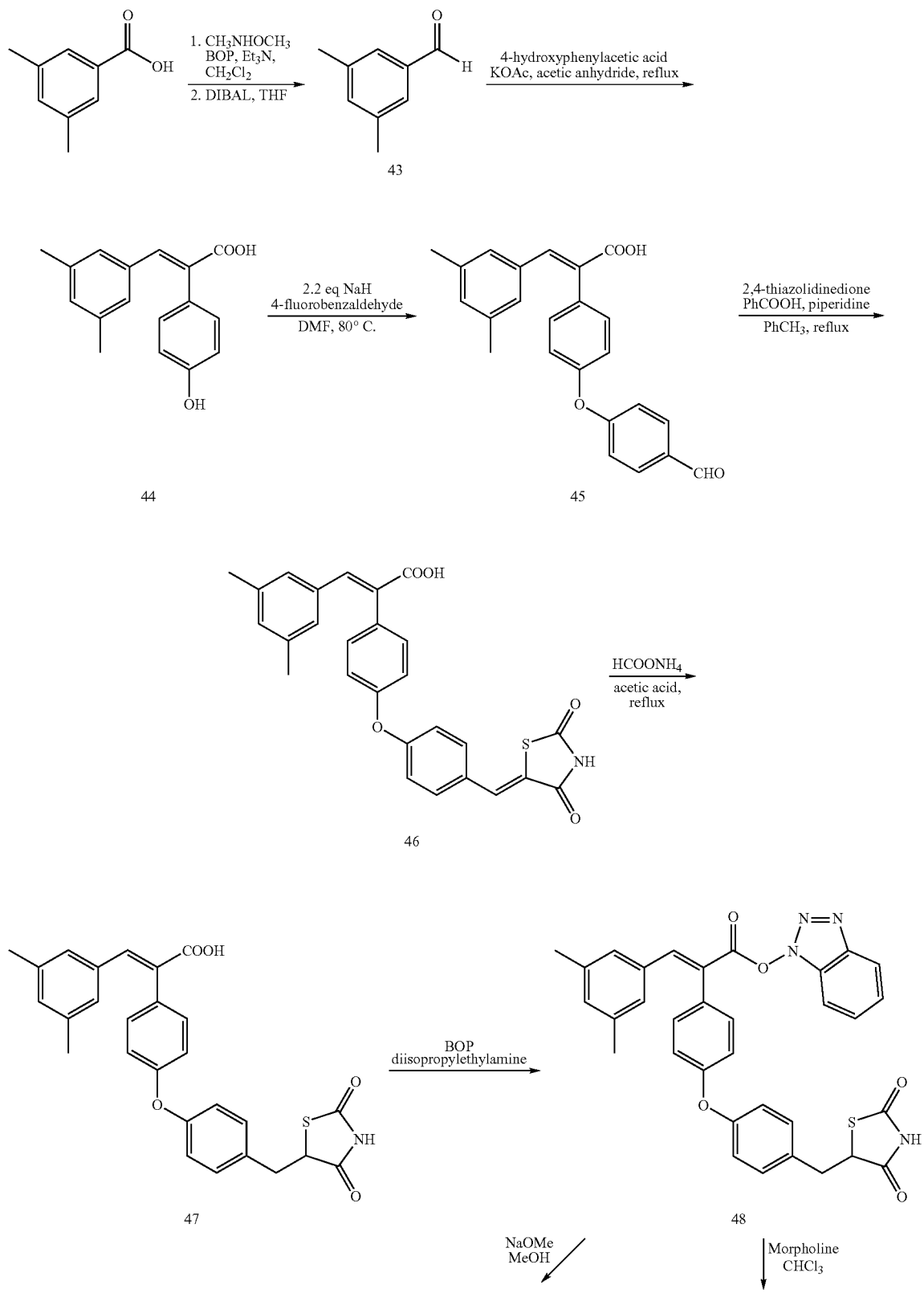

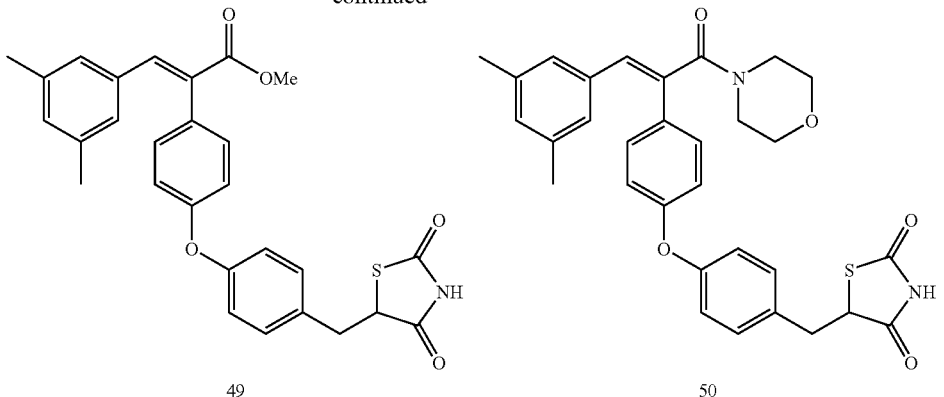
49
50
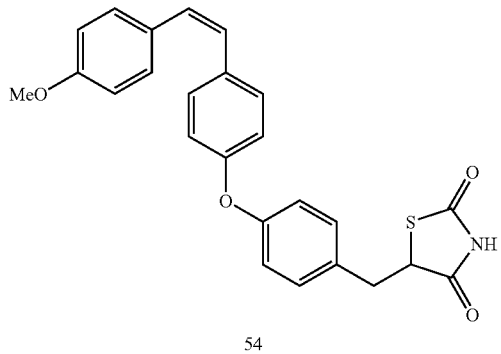
54
SCHEME 8
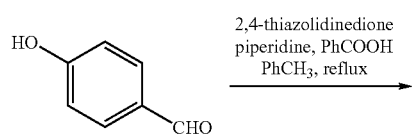
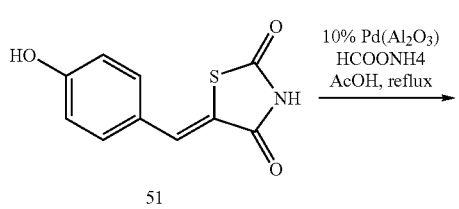
51
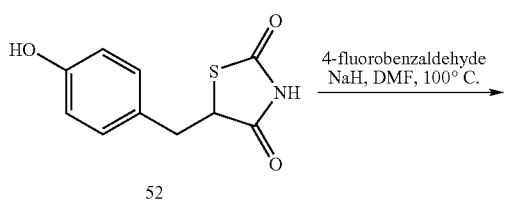
52
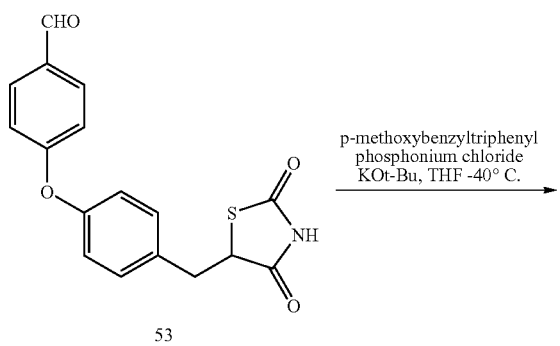
53
SCHEME 9
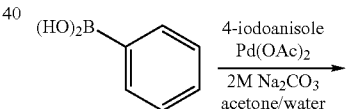
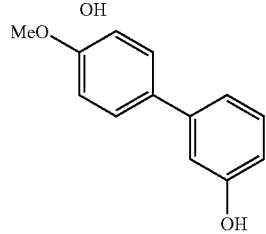
56
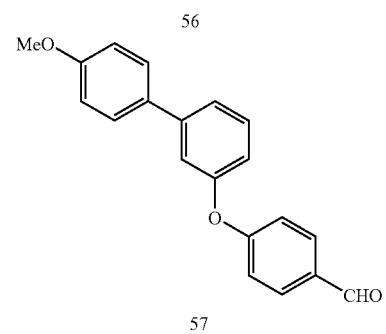
57

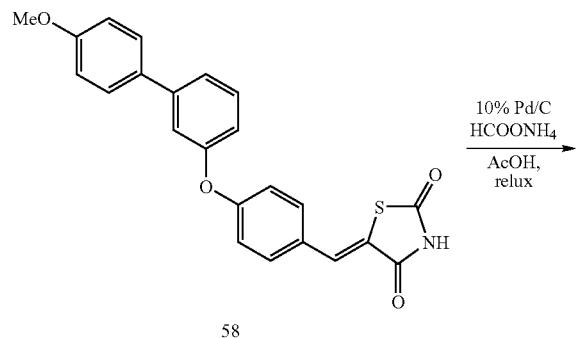
58
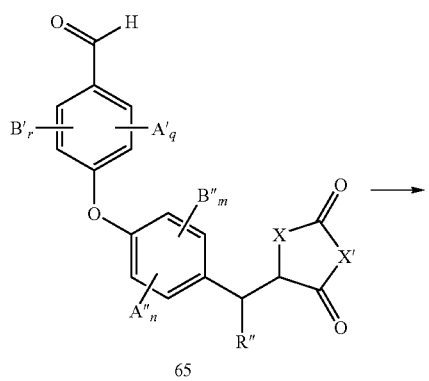
65
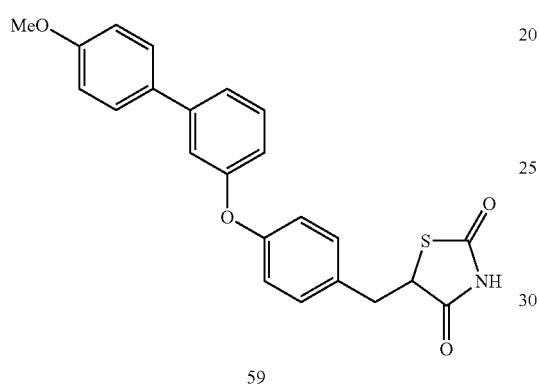
59
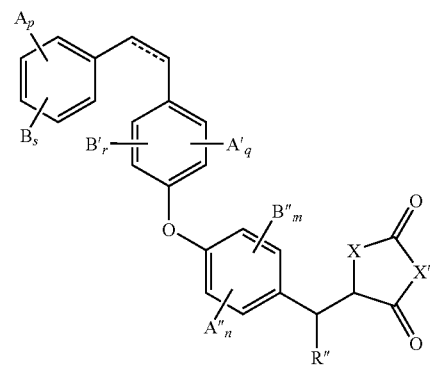
66
SCHEME 10
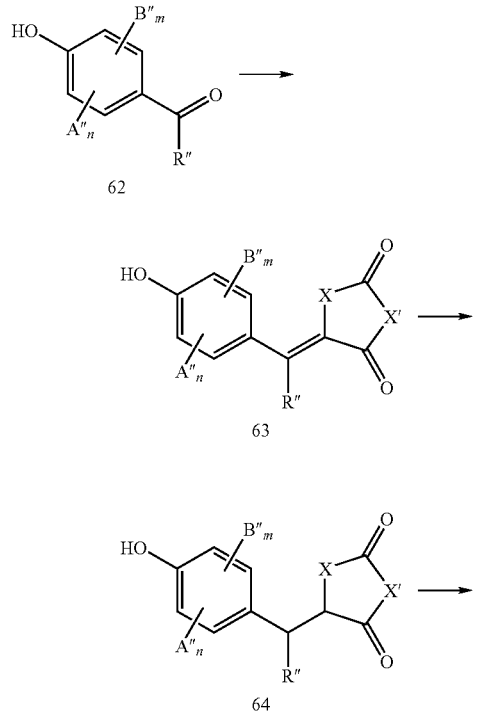
SCHEME 11
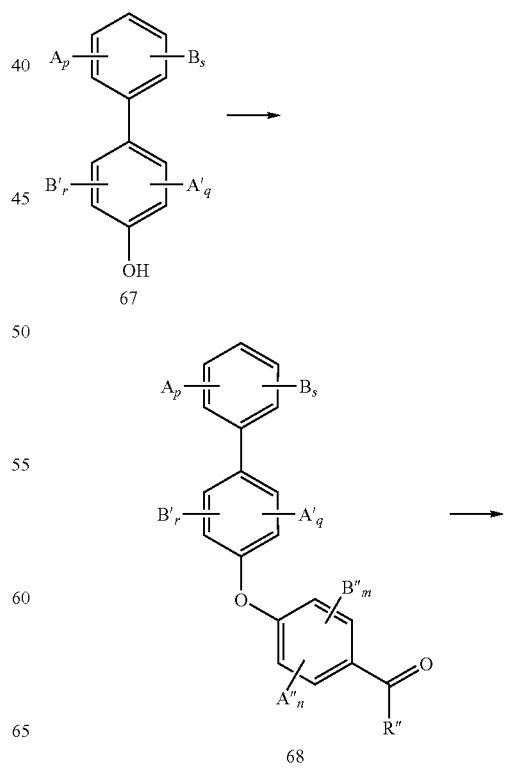

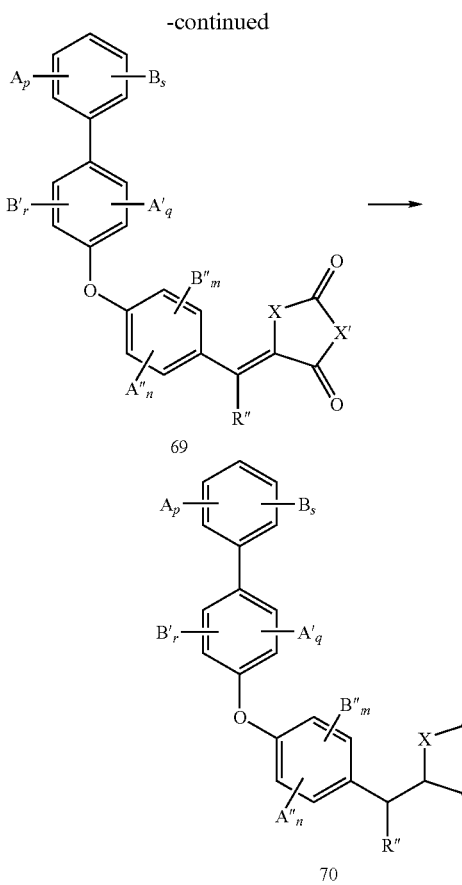

Referring to Scheme 1, the aldehyde 5 and acid 6 may be condensed in acetic anhydride and triethylamine to form the unsaturated acid 7. After esterification of the acid to provide compound 8, the phenolic hydroxy group is formed into an ether 9 with p-fluorobenzaldehyde. The aldehyde 9 is then condensed with the thiazolidinedione to provide compound 10 and the bond exo to the heterocycle in compound 10 is reduced with hydrogen to form the object compound 11.

The steps in Scheme 1 are generalized in Scheme 4. The general formulas 2b, 3b, 4b, 6b, 7b and 8b correspond respectively to formulas 5, 6, 7, 9, 10 and 11 in Scheme 1.

In Scheme 5, the general synthesis of the tricyclic products 35 and 36 is shown. The aldehyde or ketone 32 is condensed with 33 to form the bicyclic compound 34. The compound 34 is condensed with the heterocyclic dione to form the tricyclic product 35, which can be optionally hydrogenated to 36.

In Scheme 10, the general synthesis of compounds where R=R'=H is shown. The aldehyde or ketone 62 is condensed with the heterocyclic dione to form the bicyclic compound 63, which can be optionally hydrogenated to form the product 64. Coupling of 64 with optionally substituted aldehyde yields the tricyclic compound 65. Wittig reaction of 65 results in the formation of stilbene derivative 66.

In Scheme 11, the general synthesis of biphenyl products 69 and 70 is shown. Coupling of optionally substituted hydroxyl biphenyl 67 with optionally substituted aldehyde or ketone yields 68. The aldehyde or ketone 68 is condensed with the heterocyclic dione to form the compound 69, which can be optionally hydrogenated to form the product 70.

In Formula 1, $C_1$-$C_{20}$ linear or branched alkyl means groups such as methyl, ethyl, propyl, isopropyl, n-butyl, isobutyl, t-butyl, sec-butyl, isopentyl, neopentyl, etc. The $C_2$-$C_{20}$ linear or branched alkenyl means unsaturated groups such as ethenyl, propenyl, n-butenyl, isobutenyl, including groups containing multiple sites of unsaturation such as 1,3-butadiene, and the like. The halo groups include chloro, fluoro, bromo, iodo. Substituted $C_1$-$C_{20}$ linear or branched alkyl or substituted $C_2$-$C_{20}$ linear or branched alkenyl means that the alkyl or alkenyl groups may be substituted with groups such as halo, hydroxy, carboxyl, cyano, amino, alkoxy, and the like. The $C_1$-$C_{20}$ acylamino or acyloxy group means an oxygen or amino group bonded to an acyl group (RCO) where R can be hydrogen, $C_1$-$C_{20}$ linear or branched alkyl or $C_2$-$C_{20}$ linear or branched alkenyl. Alkenyl groups are —C≡C—, where R can be hydrogen, $C_1$-$C_{20}$ linear or branched alkyl or $C_2$-$C_{20}$ linear or branched alkyl. Alkoxycarbonyl means a group ROCO— where R can be hydrogen, $C_1$-$C_{20}$ linear or branched alkyl or $C_2$-$C_{20}$ linear or branched alkenyl. The $C_1$-$C_{20}$ alkyl carboxyl amino group means a group RCON(R)— where R can be independently hydrogen, $C_1$-$C_{20}$ linear or branched alkyl or $C_2$-$C_{20}$ linear or branched alkenyl. Carboxyl is the group $HO_2C$—, and alkanoyl is the group RCO— wherein R is a linear or branched carbon chain. The group aroyl is Ar—CO— wherein Ar is an aromatic group such as phenyl, naphthyl, substituted phenyl, and the like. Aralkanoyl is the group Ar—R—CO— wherein Ar is a aromatic group such as phenyl, naphthyl, substituted phenyl, etc. and R is a linear branched alkyl chain.

As indicated earlier, the compounds of the invention where a, b or c represents a double bond may have either the E or Z configuration. On the other hand, when a, b or c is absent, i.e. a single bond is present, the resulting compounds may be R- and/or S-stereoisomers. The invention contemplates racemic mixtures of such stereoisomers as well as the individual, separated stereoisomers. The individual stereoisomers may be obtained by the use of an optically active resolving agent. Alternatively, a desired enantiomer may be obtained by stereospecific synthesis using an optically pure starting material of known configuration.

The preparation of compound 11, i.e. 5-(4-(4-(1-carbomethoxy)-2-(3,5-dimethoxy phenyl)-ethenyl)-phenoxy)-benzyl)-2,4-thiazolidinedione (also known as 3-(3,5-dimethoxy-phenyl)-2-{4-[4-(2,4-dioxo-thiazolidin-5-ylmethyl)-phenoxy]-phenyl}-acrylic acid methyl ester), is described below with reference to Scheme 1.

Perkin condensation of 3,5-dimethoxybenzaldehyde 5 with 4-hydroxyphenylacetic acid 6 yielded the alpha-phenyl substituted cinnamic acid 7 exclusively as E-isomer. The geometry of the double bond was confirmed by $^1$HNMR comparison with the reported compound (Pettit et al, J Nat Prod 51:517-27, 1998). Esterification of 7 followed by condensation with 4-fluorobenzaldehyde yielded 9. Knovenagel condensation of aldehyde 9 with 2,4-thiazolidinedione in the presence of piperidinium benzoate with azeotropic removal of water gave a good yield of 10.

A major challenge was selective hydrogenation of the double bonds in order to produce compounds 11, 17 and 18. Reduction of 10 with magnesium/methanol was non-selective and yielded a mixture of products. Zinc-acetic acid reduction gave a mixture of polar product. Hydrogenation with 10% palladium on carbon as catalyst in 1,4-dioxane yielded a mixture of 11 and 18 in a ratio of 6:4. Separation of the compounds from this mixture was only possible by reverse phase chromatography on C-18 silica. These problems were overcome in several ways. Hydrogenation of 10 using ammonium formate as hydrogen donor in the presence of palladium catalyst (Hudlicky, ACS Monograph 188:46-7, 1996; Ram and Ehrenkaufer, Synthesis 91-5, 1988) produced minimal amounts of the over-reduced product 18, and isolation of 11 in high purity was possible by repeated crystallization from methanol. In a preferred variation of this approach, platinum catalyst was substituted for palladium, and the crude product was recrystallized from dichloromethane; with these modifications both the amount of catalyst required and the reaction time were significantly reduced, while the overall yield was considerably improved. In an another attempt to make 11, the aldehyde 9 was reduced to alcohol 12 which upon treatment with $PBr_3$ yielded the bromo compound 13 in high yield. The bromo compound was condensed with 2,4-thiazolidinedione anion generated by BuLi to yield 11 in low yield.

It was difficult to synthesize 18 in good yield from either 10 or 11 by palladium-catalyzed hydrogenation due to poisoning of the catalyst by the 2,4-thiazolidinedione moiety in the molecule; the resulting mixtures contained 18 as a minor product. To solve this problem (as shown in Scheme 2), 8 was first reduced, by using 10% palladium on carbon as catalyst, to 15 quantitatively followed by coupling with 4-fluorobenzaldehyde and 2,4-thiazolidinedione to furnish 17 in good yield. Reduction of 17 with palladium on carbon catalyst for a longer period of time and catalyst renewal half-way through the reaction, followed by chromatographic purification over C-18 reverse phase silica gel, produced 18 in moderate yield.

The synthetic strategy adopted to prepare 23, the corresponding Z-isomer of 11, is outlined in Scheme 3. Prolonged heating of 7 with acetic anhydride and triethylamine (Kessar et al, Indian J Chem 20B: 1-3, 1981) yielded the corresponding Z-isomer 19 in 13% yield. Interestingly, the reaction of 2,4-thiazolidinedione with 21, in order to produce 22, showed minimal isomerization of the cinnamic acid double bond and resulted in a mixture of E- and Z-isomers in a ratio of 1:7 respectively. Reduction was carried out without further purification and the final product was purified by preparative HPLC to yield 23.

EXAMPLE 1

General Methods. Melting points were measured on a Mel-Temp melting point apparatus and are uncorrected. The $^1$H NMR and $^{13}$C NMR spectra were recorded on a JEOL Eclipse (400 MHz) or Nicolet NT 36 (360 MHz) spectrometer and are reported as parts per million (ppm) downfield from TMS. The infrared spectra were recorded on a Nicolet Impact 410 FT-IR spectrophotometer. The mass spectra were recorded on Fison VG Platform II of HP 1100 MDS 1964A mass spectrophotometer. UV spectra were recorded on a Beckman DU650 spectrophotometer. TLC was done on Merck silica gel $F_{254}$ precoated plates. The silica gel used for column chromatography was 'Baker' silica gel (40 μm) for flash chromatography.

3-(3,5-Dimethoxyphenyl)-2-(4-hydroxyphenyl)-acrylic acid (7). To a mixture of 3,5-dimethoxybenzaldehyde, 5, (500 g, 3.0 mol) and 4-hydroxyphenyl acetic acid, 6, (457 g, 3.0 mol) was added acetic anhydride (1.0 L, 10.60 mole) and triethylamine (420 mL, 3.0 mol). After stirring at 130-140° C. for 6 h, the mixture was cooled to room temperature. Concentrated HCl (1 L) was added to the reaction mixture slowly over 50 min while keeping the temperature between 20-30° C. The light yellow precipitate obtained was filtered and washed with water. The solid was dissolved in 3N NaOH (5 L) and stirred for 1 h and filtered. The filtrate was acidified to pH 1 with concentrated HCl while maintaining a temperature at 25-30° C. The precipitated product was filtered and washed with water to give crude product that was recrystallized from MeOH—$H_2O$ and dried at 40° C. for 6 h to yield 7 (428 g, 47%): mp 225-227° C. (lit. 226-228° C.)[17]; $^1$HNMR (360 MHz, DMSO-$d_6$) δ 12.48 (br s, 1H), 9.42 (s, 1H), 7.59 (s, 1H), 6.95 (d, J=8.0 Hz, 2H), 6.76 (d, J=8.0 Hz, 2H), 6.35 (t, J=2.2 Hz, 1H), 6.27 (d, J=2.2 Hz, 2H), 3.56 (s, 6H); MS (EI) m/z 299[M]$^-$.

3-(3,5-Dimethoxyphenyl)-2-(4-hydroxyphenyl)-acrylic acid methyl ester (8). Methanol (3.0 L) was added to a thoroughly dried 7 (427.5 g, 1.42 mol) under argon. To this stirred suspension concentrated sulfuric acid (100 mL) was added and heated at reflux for 20 h under nitrogen. Methanol was evaporated under reduced pressure at 30° C. The residue was taken up in ethyl acetate (3.0 L) and washed with water (2×1.0 L), saturated aqueous Na $HCO_3$ (2×1.0 L), brine (2×1.0 L). The organic layer was dried on anhydrous magnesium sulfate, filtered and the solvent was evaporated. The residue obtained was dried thoroughly under high vacuum as white solid, (433.6 g 97%): mp 106-108° C.; $^1$HNMR (360 MHz, $CDCl_3$): δ 7.72 (s, 1H), 7.06 (d, J=7.9 Hz, 2H), 6.77 (d, J=7.9 Hz, 2H), 6.33 (t, J=2.2 Hz, 1H), 6.26 (d, J=2.2 Hz, 2H), 5.74 (s, 1H), 3.81 (s, 3H), 3.60 (s, 6H); MS (EI) m/z 315[M]$^+$; Anal. ($C_{18}H_{18}O_5$) C, H.

3-(3,5-Dimethoxyphenyl)-2-[4-(4-formylphenoxy)-phenyl]-acrylic acid methyl ester (9). Under argon, 8 (433.0 g, 1.37 mol) was dissolved in dry DMF (1.6 L) and to this sodium hydride (60.4 g, 1.51 mol) was added. To the resulting orange solution 4-fluorobenzaldehyde (185.0 mL, 1.71 mol) was added and heated at 80° C. for 18 h. The reaction mixture was cooled to room temperature, diluted with ethyl acetate (3.0 L) and extracted with water (3×1.0 L), then brine (1×1.0 L). The organic layer was dried over anhydrous sodium sulfate, filtered and solvent was evaporated. The residue was suspended in methanol (3.0 L) and stirred overnight. Solid was filtered and dried under vacuum at 40° C. to yield 9 as pale yellow, solid (445 g, 77%): mp 108-110° C. $^1$HNMR (360 MHz, $CDCl_3$) δ 9.94 (s, 1H), 7.86 (d, J=8.6 Hz, 2H), 7.80 (s, 1H), 7.28 (d, J=8.6 Hz, 2H), 7.11 (overlapped d, J=9.0 Hz, 2H), 7.08 (overlapped d, J=9.0 Hz, 2H), 6.36 (t, J=2.2 Hz, 1H), 6.25 (d, J=2.2 Hz, 2H), 3.83 (s, 3H), 3.63 (s, 6H); Anal. ($C_{25}H_{22}O_6$) C, H.

3-(3,5-Dimethoxyphenyl)-2-{4-[4-(2,4-dioxothiazolidin-5-ylidenemethyl)-phenoxy]-phenyl}-acrylic acid methyl ester (10). To a stirred suspension of 9 (352 g, 0.82 mol) in anhydrous toluene (2.5 L), 2,4-thiazolidinedione (98.6 g, 0.84 mol), benzoic acid (134 g, 1.10 mol) and piperidine (107.4 g, 1.26 mol) was added sequentially and heated at reflux temperature with continuous removal of water with the help of Dean-Stark apparatus for 5 h. Toluene (1.0 L) was removed from the reaction mixture and cooled overnight at 4° C. Solid separated was filtered and mother liquor was evaporated to dryness under reduced pressure. The residue obtained was re-dissolved in a mixture of MeOH-diethylether (1:1, 3.0 L). On standing overnight at 4° C., the solution yielded more solids. Solid from both the lots were combined and dried overnight in vacuum oven at 40° C. to give 10 as yellow solid (362.5 g, 86%): mp 106-108° C.; mp 225-226° C.; $^1$H NMR (360 MHz, DMSO-$d_6$): δ 12.53 (br s, 1H), 7.78 (s, 1H), 7.73 (s, 1H), 7.63 (d, J=9.2 Hz, 2H), 7.25 (d, J=9.2 Hz, 2H), 7.13 (overlapped d, J=8.3 Hz, 2H), 7.11 (overlapped d, J=8.6 Hz, 2H), 6.42 (t, J=2.2 Hz, 1H), 6.27 (d, J=2.2 Hz, 2H), 3.73 (s, 3H), and 3.59 (s, 6H); MS (EI) m/z 518[M]$^+$; Anal. ($C_{28}H_{23}NO_7S$) C, H, N.

5-(4-(4-(1-carbomethoxy-2-(3,5-dimethoxyphenyl)-ethenyl)-phenoxy)-benzyl)-2,4-thiazolidinedione, also called 3-(3,5-dimethoxyphenyl)-2-{4-[4-(2,4-dioxothiazolidin-5-ylmethyl)-phenoxy]-phenyl}-acrylic acid methyl ester (compound 11). Compound 10 (30 g, 58 mmol) was dissolved in warm dioxane (900 mL), transferred to a 2 L hydrogenation bottle and 10% Pd—C (~50% water, 15 g) was added to this and hydrogenated in a Parr hydrogenator at 60 psi for 24 h. Following this period, an additional 15 g Pd—C was added and hydrogenation was allowed to continue for another 24 h. Catalyst was filtered through a bed of Celite and solvent was evaporated. The residue was taken up in acetonitrile (500 mL) and adsorbed on C-18 silica (50 g). The adsorbed material was placed on the top of a column containing C-18 reverse phase silica gel (400). Column was eluted with $CH_3CN$ in $H_2O$ (45%, 2 L), $CH_3CN$ in $H_2O$ (50%, 2 L), $CH_3CN$ in $H_2O$ (55%, 2 L) to elute the undesired fractions. Fractions were collected with the start of 60% $CH_3CN$ in $H_2O$ elution for the desired compound. Fractions were mixed on the basis of their HPLC purity. Acetonitrile was evaporated under reduced pressure. Water was removed by lyophilization. Yield: 12 g (40%). White solid; m.p. 126-128° C. $^1$H NMR (DMSO-$d_6$) δ 12.01 (br, 1H), 7.73 (s, 1H), 7.28 (d, J=8.6 Hz, 2H), 7.19 (d, J=8.6 Hz, 2H), 7.02 (d, J=8.6 Hz, 2H), 6.96 (d, J=8.6 Hz, 2H), 6.40 (t, J=2.2 Hz, 1H), 6.27 (d, J=2.2 Hz, 2H), 4.92 (dd, J=9.2 and 4.4 Hz, 1H), 3.73 (s, 3H), 3.57 (s, 6H), 3.37 (dd, J=14.8 and 4.3 Hz, 1H) and 3.12 (dd, J=14.8 and 9.4 Hz, 1H); IR (KBr) $v_{max}$ 3200, 2950, 2850, 1700, 1600, 1500, 1350, 1150, and 850 cm$^{-1}$; EIMS: m/z, 518, [M-H]$^-$ 265, 249, and 113.

3-(3,5-Dimethoxyphenyl)-2-{4-[4-(2,4-dioxothiazolidin-5-ylmethyl)-phenoxy]-phenyl}-acrylic acid methyl ester (11). To a solution of 10 (599 g, 1.16 mol) in glacial acetic acid (11.5 L), ammonium formate (4.0 kg, 62.9 mol) was added and stirred for 30 min. A slurry of Pd on carbon (10%, dry, 300 g) in glacial acetic acid (500 mL) was added to the flask (caution: in a large scale reaction exothermicity may be a problem; rigorous exclusion of oxygen is desirable) and heated at 120° C. for 24 h followed by stirring at room temperature for 48 h. The resulting mixture was filtered through a bed of Celite®. The filtrate was poured slowly into vigorously stirred water (12 L) and the separated solid was filtered and dried. Resulting solid was purified by slurring twice in hot methanol followed by once from ethanol to yield pure 11 as white solid (296 g, 49.2%): mp 126-128° C.; $^1$H NMR (400 MHz, DMSO-$d_6$) δ 12.01 (br s, 1H), 7.73 (s, 1H), 7.28 (d, J=8.6 Hz, 2H), 7.19 (d, J=8.6 Hz, 2H), 7.02 (d, J=8.6 Hz, 2H), 6.96 (d, J=8.6 Hz, 2H), 6.40 (t, J=2.2 Hz, 1H), 6.27 (d, J=2.2 Hz, 2H), 4.92 (dd, J=9.2 and 4.4 Hz, 1H), 3.73 (s, 3H), 3.57 (s, 6H), 3.37 (dd, J=14.8 and 4.3 Hz, 1H) and 3.12 (dd, J=14.8 and 9.4 Hz, 1H); IR (KBr) $v_{max}$ 3200, 2950, 2850, 1700, 1600, 1500, 1350, 1150, and 850 cm$^{-1}$; MS (EI) m/z 518[M-H]$^-$, 265, 249, and 113; Anal. ($C_{28}H_{25}NO_7S$) C, H, N.

3-(3,5-Dimethoxyphenyl)-2-{4-[4-(2,4-dioxothiazolidin-5-ylmethyl)-phenoxy]-phenyl}-acrylic acid methyl ester (11). Compound 10 (20 g, 38.6 mmol), ammonium formate (150 g, 2.38 mol), 10% Pt/C (dry, 4 g) and acetic acid (660 mL) were combined into a round bottom flask equipped with reflux condenser, thermometer and mechanical stirrer. The reactor was evacuated and purged three times with nitrogen then, heated to a steady reflux (ca. 124° C.). Reaction was completed within 15 h and allowed to cool with stirring to ambient room temperature. After cooling, the mixture was filtered though a pad of Celite® (5 g) and the filter pad washed with fresh acetic acid (2×100 mL). The mother liquor and washes were combined and concentrated. The residue was then diluted with dichloromethane (400 mL), and the combined organics were extracted twice with water (400 mL) and 5% bicarbonate (400 mL). The organic portion was then dried and poured through silica gel (30 g) and washed with dichloromethane (2×100 mL). The washes were combined and concentrated. The residue was diluted with ethanol, allowed to cool to 60° C. and seed crystals were added. This slurry was stirred at 50° C. for about 30 min then allowed to cool to ambient room temperature to yield compound 11 (12.85 g, 64%) with an HPLC assay of 98.1%.

3-(3,5-Dimethoxyphenyl)-2[4-(4-hydroxymethylphenoxy)-phenyl]-acrylic acid methyl ester (12). Compound 9 (5.0 g, 11.9 mmol) was suspended in anhydrous ethanol (60 mL) at room temperature and sodium borohydride (0.23 g, 6.1 mmol) was added with efficient stirring. Reaction was complete in 1 h, solvent was evaporated and the residue was dissolved in ethyl acetate. The organic layer was extracted with water (50 mL), brine (25 mL), dried on anhydrous magnesium sulfate, filtered and solvent was evaporated to yield the title compound 12 as white solid (5.1 g, 100%): mp 93-95° C.; $^1$H NMR (400 MHz, DMSO-$d_6$) δ 7.72 (s, 1H), 7.35 (d, J=8.8 Hz, 2H), 7.19 (d, J=8.8 Hz, 2H), 7.02 (d, J=8.4 Hz, 2H), 7.00 (d, J=8.4 Hz, 2H), 6.41 (t, J=2.4 Hz, 1H), 6.29 (d, J=2.0 Hz, 2H), 5.18 (t, J=6.4 Hz, 1H), 4.49 (d, J=4.8 Hz, 2H), 3.73 (s, 3H), 3.57 (s, 6H); MS (EI) m/z 315[M]$^+$. Anal. ($C_{25}H_{24}O_6$) C, H.

2-[4-(4-Bromomethylphenoxy)-phenyl]-3-(3,5-dimethoxyphenyl)-acrylic acid methyl ester (13). A solution of PBr$_3$ (4.8 mL of 1.0 M in $CH_2Cl_2$) was added dropwise to 12 (5.0 g, 11.9 mmol) dissolved in $CH_2Cl_2$ (20 mL) at temperature with good stirring. After 1 h, the solution was extracted with water (2×60 mL) and brine (20 mL). The organic phase was dried over anhydrous magnesium sulfate, filtered through a small bed of silica gel (20 g) and solvent was evaporated. The resulting tacky syrup was dried under high vacuum for 48 h at room temperature to yield the title compound (5.7 g, 99%): mp 79-81° C.; $^1$H NMR (400 MHz, DMSO-$d_6$) δ 7.73 (s, 1H), 7.49 (d, J=8.4 Hz, 2H), 7.22 (d, J=8.4 Hz, 2H), 7.07 (d, J=8.4 Hz, 2H), 7.00 (d, J=8.4 Hz, 2H), 6.42 (t, J=2.4 Hz, 1H), 6.28 (d, J=2.0 Hz, 2H), 4.73 (d, J=4.8 Hz, 2H), 3.68 (s, 3H), 3.58 (s, 6H); Anal. ($C_{25}H_{23}BrO_5$) C: calculated, 61.12; found, 62.26; H: calculated 4.80; found 4.88.

3-(3,5-Dimethoxyphenyl)-2-{4-[4-(2,4-dioxothiazolidin-5-ylmethyl)-phenoxy]-phenyl}-acrylic acid methyl ester (11). 2,4-Thiazolidinedione (2.83 g, 24.2 mmol) was dissolved in dry THF (170 mL) and cooled to 0° C. under argon. Butyllithium (1.6 M in hexanes, 30 mL, 48.0 mmol) was added dropwise. Stirring continued for 0.5 h at 0° C. Under argon, 13 (5.7 g, 11.8 mmol) was dissolved in dry THF (30 mL) and was added rapidly via syringe to the above suspension with rapid stirring. The temperature was maintained at 0° C. for 45 min before quenching with aqueous HCl (5%, 40 mL). Additional $H_2O$ (40 mL) was added and extracted with ethyl acetate (3×30 mL). Organic layers were combined, washed with brine, dried over anhydrous magnesium sulfate, filtered and the solvent was evaporated. Flash chromatography over silica gel using hexanes-ethyl acetate (3:2) as eluting solvent yielded the title compound, 11, (0.93 g, 15%). The melting point and $^1$H NMR of compound 11 made by this method were identical to those for compound 11 produced by the synthetic route starting from compound 10 described above.

3-(3,5-Dimethoxyphenyl)-2-{4-[4-2,4-dioxothiazolidin-5-ylmethyl)-phenoxy]-phenyl acrylic acid (14). To a stirred, cooled below 10° C., suspension of 11 (10 g, 19.27 mmol) in methanol (50 mL), aqueous sodium hydroxide (2N, 33.7 mL, 67.4 mmol) was added and stirred for 15 h at room temperature. The resulting pale yellow solution was cooled to 10° C. and acidified with aqueous HCl (5%, 115 mL). Solid separated was filtered and washed with water (3×30 mL), recrystallized from ethanol to give 14 as white solid (7.14 g, 73%): mp 138-140° C.; $^1$H NMR (400 MHz, DMSO-$d_6$) δ 7.69 (s, 1H), 7.28 (d, J=8.8 Hz, 2H), 7.19 (d, J=8.8 Hz, 2H), 7.02 (d, J=8.8 Hz, 2H), 6.97 (d, J=8.8 Hz, 2H), 6.41 (t, J=2.4 Hz, 1H), 6.28 (d, J=2.4 Hz, 2H), 4.92 (dd, J=9.2 and 4.4 Hz, 1H), 3.58 (s, 6H), 3.38 (dd, J=14.0 and 4.0 Hz, 1H) and 3.13 (dd, J=14.4 and 9.2 Hz, 1H); MS (EI) m/z 506[M]$^+$; Anal. ($C_{27}H_{23}NO_7S$) C, H.

3-(3,5-Dimethoxyphenyl)-2-(4-hydroxyphenyl)-propionic acid methyl ester (15). To a suspension of 8 (6.28 g, 20.0 mmol) in ethanol (200 mL) palladium on carbon (10%, wet, 0.63 g) was added and stirred under $H_2$ at atmospheric pressure at room temperature for 18 h. Catalyst was filtered through a bed of Celite® and solvent was evaporated under reduced pressure to yield 15 as white solid (6.32 g, 100%): mp 63-65° C.; $^1$HNMR (400 MHz, DMSO-$d_6$): δ 7.15 (d, J=8.7 Hz, 2H), 6.74 (d, J=8.7 Hz, 2H), 6.29 (t, J=2.4 Hz, 1H), 6.25 (d, J=2.4 Hz, 2H), 3.78 (t, J=8.7 Hz, 1H), 3.72 (s, 6H), 3.62 (s, 3H), 3.31 (dd, J=13.5 and 8.4 Hz, 1H), 2.93 (dd, J=13.5 and 6.9 Hz, 1H); MS (EI) m/z 317[M]$^+$; Anal. ($C_{18}H_{20}O_5$) C, H.

3-(3,5-Dimethoxyphenyl)-2-[4-(4-formylphenoxy)-phenyl]-propionic acid methyl ester (16). To a suspension of sodium hydride (60% in oil, 0.25 g, 6.3 mmol) in DMF (2 mL) under argon, 15 (2.0 g, 6.3 mmol) in dry DMF (3 mL) was added. To the resulting yellow solution, 4-fluorobenzaldehyde (0.68 mL, 6.3 mmol) was added and heated at 80° C. for 18 h. The reaction mixture was cooled to room temperature, water (20 mL) was added and extracted with ethyl acetate (3×50 mL). The organic layer was dried over anhydrous sodium sulfate, filtered and solvent was evaporated. An ethyl acetate solution of crude product was filtered through a small bed of silica gel to yield 16 (1.83 g, 69%) as oil: $^1$HNMR (400 MHz, DMSO-$d_6$): δ 9.91 (s, 1H), 7.84 (d, J=8.7 Hz, 2H), 7.33 (d, J=8.7 Hz, 2H), 7.04 (d, J=5.4 Hz, 2H), 7.01 (d, J=5.4 Hz, 2H), 6.30 (t, J=2.1 Hz, 1H), 6.25 (d, J=2.1 Hz, 2H), 3.86 (t, J=7.8 Hz, 1 Hz), 3.76 (s, 6H), 3.66 (s, 3H), 3.36 (dd, J=12.6 and 8.1 Hz, 1H), 2.97 (dd, J=13.5 and 7.5 Hz, 1H); MS (EI) m/z 421 [M]$^+$.

3-(3,5-Dimethoxyphenyl)-2-{4-[4-2,4-dioxothiazolidin-5-ylidenemethyl)-phenoxy]-phenyl}-propionic acid methyl ester (17). To a stirred suspension of 16 (1.81 g, 4.3 mmol) in anhydrous toluene (25 mL), 2,4-thiazolidinedione (0.56 g, 4.74 mmol), benzoic acid (0.68 g, 5.60 mmol) and piperidine (0.60 mL, 6.03 mmol) was added sequentially and heated at reflux temperature with continuous removal of water using a Dean-Stark apparatus for 2 h. Solvent was evaporated to dryness under reduced pressure. The residue obtained was purified by silica gel chromatography, eluted with hexane-ethyl acetate (1:1) to yield 17 (1.82 g, 81%): mp 104-106° C.; $^1$H NMR (400 MHz, DMSO-$d_6$) δ 12.53 (br s, 1H), 7.76 (s, 1H), 7.60 (d, J=8.7 Hz, 2H), 7.35 (d, J=8.7 Hz, 2H), 7.07 (d, J=4.8 Hz, 2H), 7.03 (d, J=4.8 Hz, 2H), 6.33-6.28 (m, 3H), 4.01 (t, J=7.5 Hz, 1 Hz), 3.66 (s, 6H), 3.56 (s, 3H), 3.22 (dd, J=13.8 and 8.4 Hz, 1H), 2.90 (dd, J=13.5 and 7.2 Hz, 1H); MS (EI) m/z 520[M]$^+$; Anal. ($C_{28}H_{25}NO_7S$) C: calculated, 64.73; found, 65.89; H: calculated, 4.85; found, 5.08, N: calculated, 2.70; found, 2.56.

3-(3,5-Dimethoxyphenyl)-2-{4-[4-(2,4-dioxothiazolidin-5-ylmethyl)-phenoxy]-phenyl}-propionic acid methyl ester (18). 17 (1.6 g, 3.08 mmol) was dissolved in dioxane (45 mL), transferred in a hydrogenation bottle and Pd on carbon (10%, 1.0 g) was added. Hydrogenation was done at 65 psi for 34 h. Following this period, additional Pd on carbon (10%, 0.6 g) was added and hydrogenation was allowed to continue for another 18 h. Catalyst was filtered through a bed of Celite® and solvent was evaporated. The residue was purified by column chromatography on reverse phase silica gel (C-18) using acetonitrile-water (1:1) mixture to elute 18 as white solid (0.60 g, 38%): mp 125-128° C.; $^1$H NMR (400 MHz, DMSO-$d_6$) δ 12.04 (br s, 1H), 7.31 (d, J=8.4 Hz, 2H), 7.25 (d, J=8.4 Hz, 2H), 6.92 (d, J=8.6 Hz, 4H), 6.30 (d, J=2.0 Hz, 2H), 6.29 (t, J=2.0 Hz, 1H), 4.90 (dd, J=9.2 and 4.4 Hz, 1H), 3.98 (t, J=8.0 Hz, 1H), 3.67 (s, 6H), 3.56 (s, 3H), 3.37 (dd, J=13.6 and 4.0 Hz, 1H), 3.21 (dd, J=14.0 and 8.8 Hz, 1H); 3.11 (dd, J=14.0 and 9.2 Hz, 1H) and 2.90 (dd, J=13.6 and 7.6 Hz, 1H); MS (EI) m/z 522[M]$^+$; Anal. ($C_{28}H_{27}NO_7S$) C, H, N.

Z-3-(3,5-Dimethoxyphenyl)-2-(4-hydroxyphenyl)-acrylic acid (19). E-3-(3,5-dimethoxyphenyl)-2-(4-hydroxyphenyl)-acrylic acid, 7 (10.0 g, 33.3 mmol) was dissolved in a mixture of acetic anhydride (40 mL, 0.42 mole) and triethylamine (40 mL, 0.29 mole) and heated at 125° C. for 24 h. The mixture was cooled to room temperature. Ethyl acetate (150 mL) was added, further cooled to 5° C., acidified with concentrated HCl (30 mL) and stirred at this temperature for 90 min. The organic layer was separated and the aqueous layer was extracted with ethyl acetate (100 mL). The combined organic layers were washed with water (2×50 mL) and extracted with aqueous NaOH (5M, 3×70 mL). The aqueous alkaline layer was acidified with glacial acetic acid (65 mL) to pH 5.2 and stirred at 0° C. for 30 min. Solid that separated was filtered and mother liquor was acidified with concentrated HCl (90 mL) and stirred at 5° C. for 1 h. Solid that separated was filtered, washed with cold water (2×50 mL) and dried at 45° C. for 6 h to yield, 19, (1.3 g, 13%): mp 135-137° C.; $^1$HNMR (400 MHz, DMSO-$d_6$) δ 13.28 (br, 1H), 9.70 (br, 1H), 7.32. (d, J=10.4 Hz, 2H), 6.81 (s, 1H, overlapped), 6.79 (d, J=9.7 Hz, 2H), 6.67 (d, J=2.5 Hz, 2H), 6.64 (t, J=2.5 Hz, 1H), and 3.73 (s, 6H); MS (EI) m/z 299[M]$^−$.

Z-3-(3,5-Dimethoxyphenyl)-2-(4-hydroxyphenyl)acrylic acid methyl ester (20). Concentrated sulfuric acid. (10 drops) was added to a stirred methanol suspension of thoroughly dried 19 (0.60 g, 2.0 mmol) under argon and heated at reflux for 18 h. Methanol was evaporated under reduced pressure, residue was taken up in ethyl acetate (20 mL) and washed with water (20 mL), saturated aqueous Na $HCO_3$ (10 mL) and brine (10 mL). The organic layer was dried on anhydrous magnesium sulfate, filtered and the solvent was evaporated. The crude product obtained was purified by chromatography over silica gel and eluted with hexane-ethyl acetate (7:3) to yield 20 as white solid (0.24 g, 35%): $^1$HNMR (400 MHz, $CDCl_3$) δ 7.26 (d, J=8.4 Hz, 2H), 6.82 (s, 1H), 6.76 (d, J=8.4 Hz, 2H), 6.45 (d, J=2.0 Hz, 2H), 6.34 (t, J=2.0 Hz, 1H), 4.97 (s, 1H), 3.73 (s, 3H), 3.72 (s, 6H).

Z-3-(3,5Dimethoxyphenyl)-2-[4-(4-formylphenoxy)-phenyl]-acrylic acid methyl ester (21). Under argon, 20 (0.60 g, 0.9-mmol) was dissolved in dry DMF (4 mL) and to this sodium hydride (60% in oil, 0.09 g, 2.28 mmol) was added. To the resulting orange solution, 4-fluorobenzaldehyde (0.25 mL, 2.28 mmol) was added and heated at 80° C. for 18 h. The reaction mixture was cooled to room temperature, water (10 mL) was added and the mixture was extracted with ethyl acetate (3×20 mL). The crude product obtained after evaporation was purified by chromatography over silica gel and elution with a mixture of hexane-ethyl acetate (4:1) to yield 21 as white solid (0.59 g, 74%): $^1$HNMR (400 MHz, $CDCl_3$) δ 9.93 (s, 1H), 7.86 (d, J=8.8 Hz, 2H), 7.49 (d, J=8.8 Hz, 2H), 7.10 (overlapped d, J=8.8 Hz, 2H), 7.08 (overlapped d, J=8.8 Hz, 2H), 6.96 (s, 1H), 6.53 (dd, J=2.8 Hz, 2H), 6.43 (t, J=2.0 Hz, 1H), 3.80 (s, 3H), 3.79 (s, 6H).

Z-3-(3,5-Dimethoxyphenyl)-2-{4-[4(2,4-dioxothiazolidin-5-ylidenemethyl)-phenoxy]-phenyl}-acrylic acid methyl ester (22). To a stirred suspension of 21 (0.53 g, 1.3 mmol) in anhydrous toluene (10 mL), 2,4-thiazolidinedione (0.15 g, 1.30 mmol), benzoic acid (0.21 g, 1.69 mmol) and piperidine (0.19 g, 1.95 mmol) were added sequentially and the mixture was heated at reflux temperature with continuous removal of water using a Dean-Stark apparatus for 5 h. Toluene was evaporated and the residue was chromatographed over silica gel and eluted with hexane-ethyl acetate (1:1) to yield a mixture of 22 and 10 (0.60 g, 91%) in a ratio of 7:1 on the basis of proton NMR analysis: $^1$H NMR (400 MHz, DMSO-$d_6$): δ 12.53 (br s, 1H), 7.79 (s, 1H), 7.65 (d, J=8.8 Hz, 2H), 7.54 (d, J=8.8 Hz, 2H), 7.18 (overlapped d, J=8.8 Hz, 2H), 7.16 (overlapped d, J=8.8 Hz, 2H), 7.17 (overlapped s, 1H), 6.57 (d, J=2.0 Hz, 2H), 6.50 (t, J=2.0 Hz, 1H), 3.79 (s, 3H), and 3.75 (s, 6H).

Z-3-(3,5-Dimethoxyphenyl)-2-{4-[4-(2,4-dioxothiazolidin-5-ylmethyl)-phenoxy]-phenyl}-acrylic acid methyl ester (23). To a solution of 22 (0.60 g, 1.6 mmol) in acetic acid (15 mL) was added Pd on carbon (10%, 300 mg) and ammonium formate (4.3 g, 55.8 mmol) (caution: in a large scale reaction exothermicity may be a problem; rigorous exclusion of oxygen is desirable) and heated at 120° C. for 20 h. Catalyst was filtered through a bed of Celite® and acetic acid was evaporated under reduced pressure. Water (50 mL) was added to the residue and solid separated was filtered. Pure Z-isomer was isolated by preparative HPLC using Intersil ODS-3 preparative column (250×4.6 mm, 5 µm) running at a rate of 15 mL per minute using methanol:acetonitrile:water (3:3:2) containing formic acid (0.05%): mp 65-66° C.; $^1$H NMR (400 MHz, DMSO-$d_6$) δ 12.05 (br s, 1H), 7.48 (d, J=9.2 Hz, 2H), 7.29 (d, J=8.4 Hz, 2H), 7.13 (s, 1H), 7.03 (overlapped d, J=8.8 Hz, 2H), 7.01 (overlapped d, J=8.4 Hz, 2H), 6.56 (d, J=2.0 Hz, 2H), 6.49 (t, J=2.0 Hz, 1H), 4.90 (dd, J=9.2 and 4.4 Hz, 1H), 3.77 (s, 3H), 3.75 (s, 6H), 3.38 (dd, J=14.8 and 4.8 Hz, 1H) and 3.13 (dd, J=14.4 and 9.2 Hz, 1H); MS (EI) m/z 300[M]$^+$.

Figure 1A:
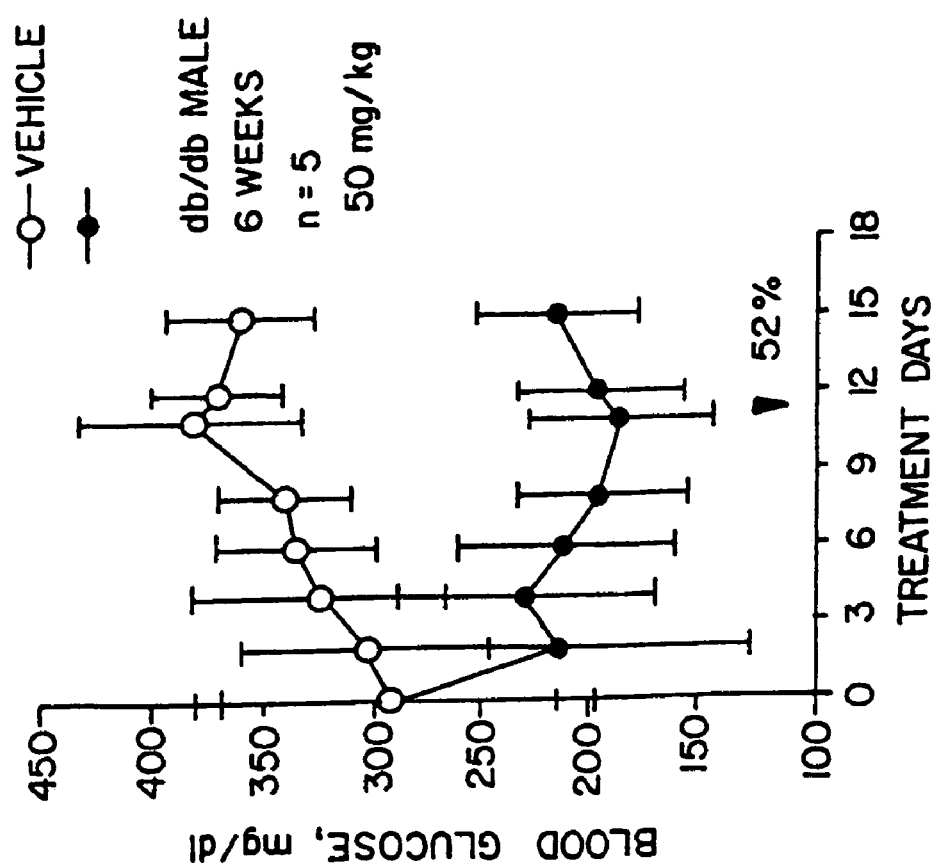

Referring to the drawings, compound 11 was administered in a single oral dose (50 mg/kg body weight) for 15 days to db/db male mice as shown in FIG. 1A. A substantial reduction in blood glucose level was observed. There was no increase in body weight in the treatment group as compared to the control treated with the vehicle without the active ingredient, FIG. 1B.

Figures 2A, 2B:
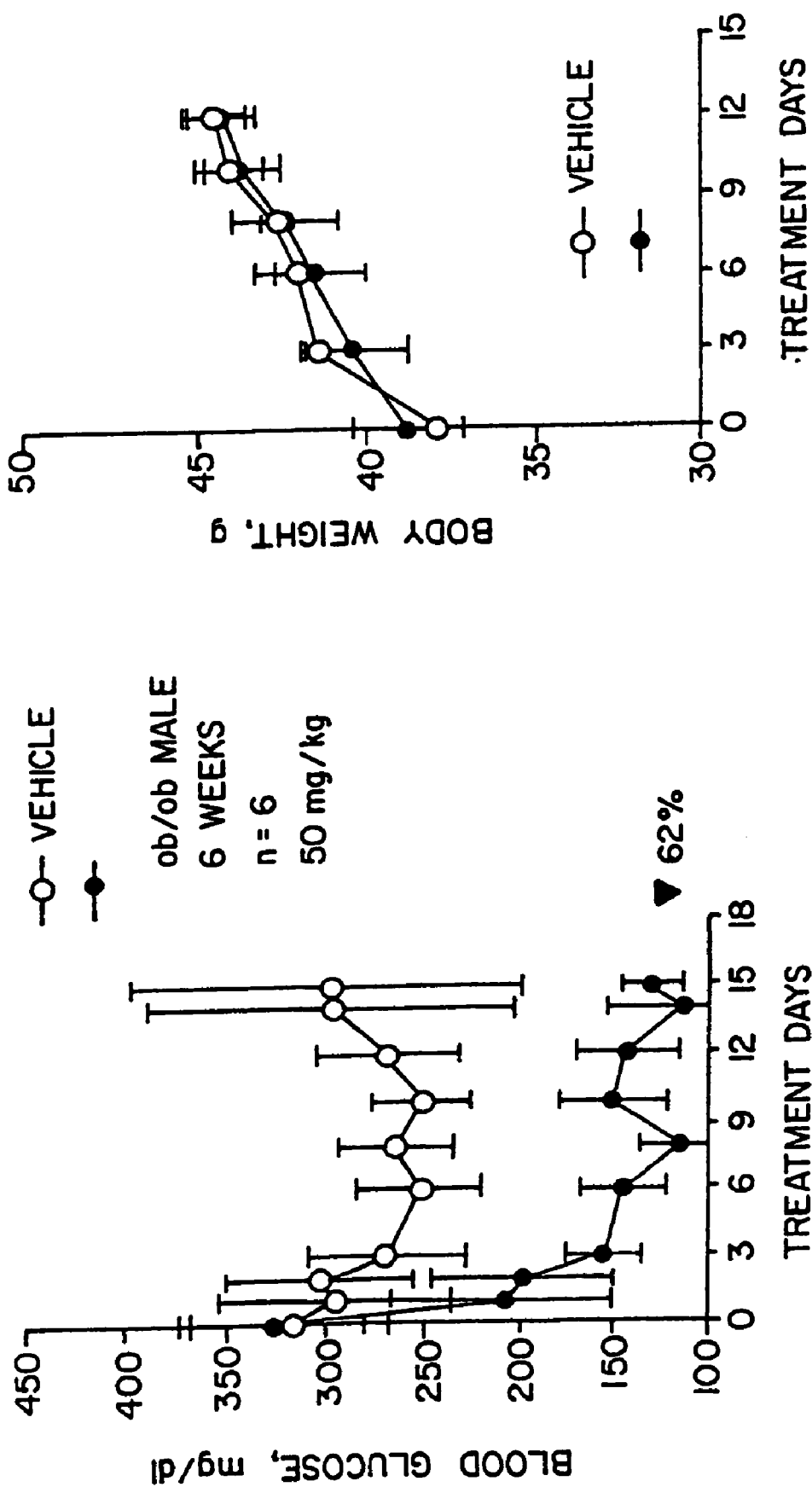
FIGS. 2A and 2B show graphs of the blood glucose levels and body weights of ob/ob (genetically obese and spontaneously diabetic) male mice given a compound according to the invention over a period of 15 days.
Figure 3B:
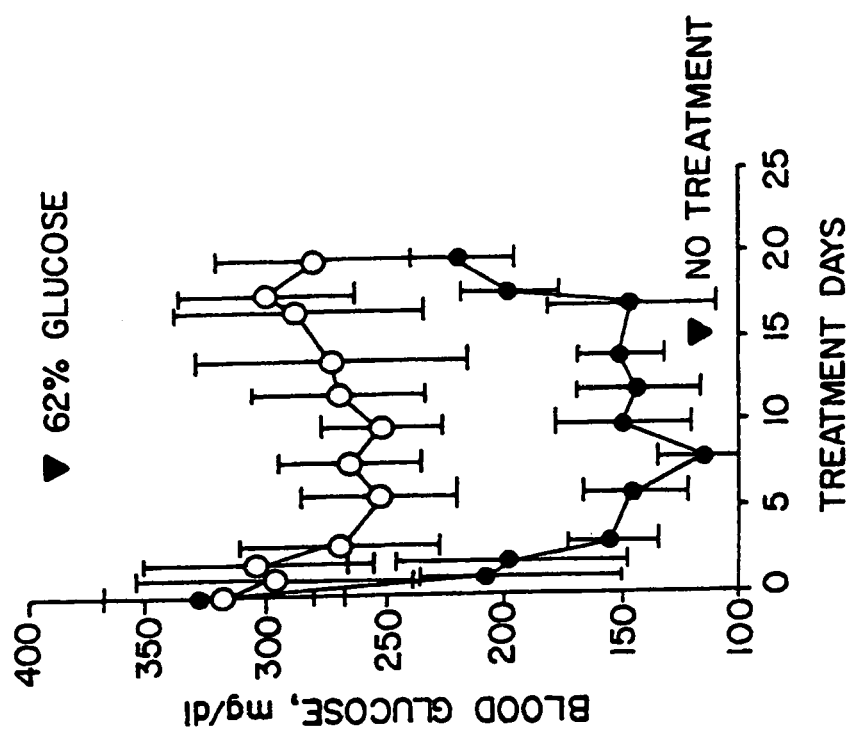
FIGS. 3A and 3B with graphs of blood glucose levels of db/db mice and ob/ob mice, respectively, given a compound according to the invention over a period of 20-25 days.
Figure 3A:
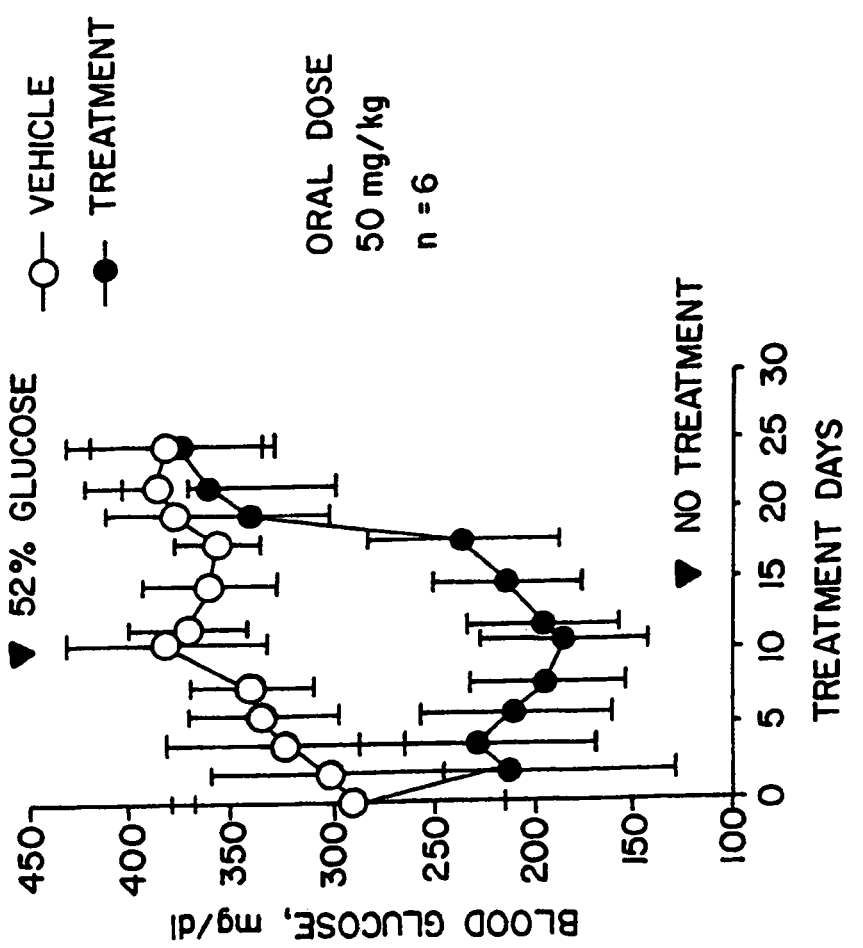
Figure 4:
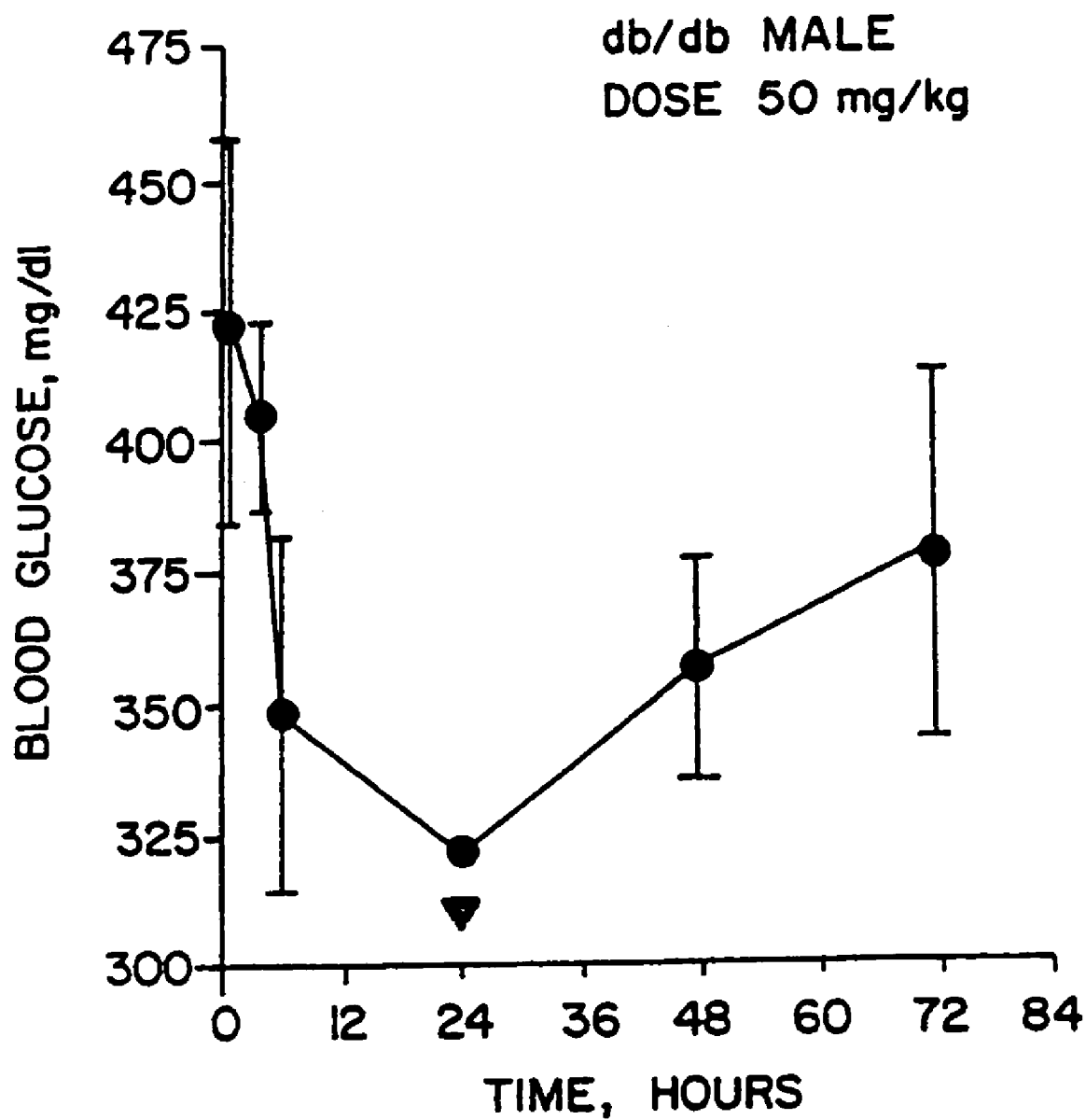
FIG. 4 shows a graph of blood glucose level in db/db male mice over 72 hours following a dosage of the compound.

The compound was orally administered to ob/ob mice with a single oral dose (50 mg/kg body weight). As shown in FIG. 2A, there was a 62% drop in blood glucose level and, similar to db/db mice, there was no significant increase in body weight between the control and the treatment groups as shown in FIG. 2B. This is in contrast to treatment of diabetic animals by thiazolidinedione type compounds which are known to be associated with increase in body weight. See Okuno et al., *J. Clin. Invest.*, 101, 1354-1361 (1998) and Yoshioka et al., *Metabolism*, 42, 75-80 (1993). By stopping treatment after day 15 in both models, there was shown an increase in glucose level as depicted in FIGS. 3A and 3B. The time course of the drug effect is shown in FIG. 4. Oral administration of a single dose of the compound in db/db mice was effective for 24 hours and beyond.

Figure 6D:
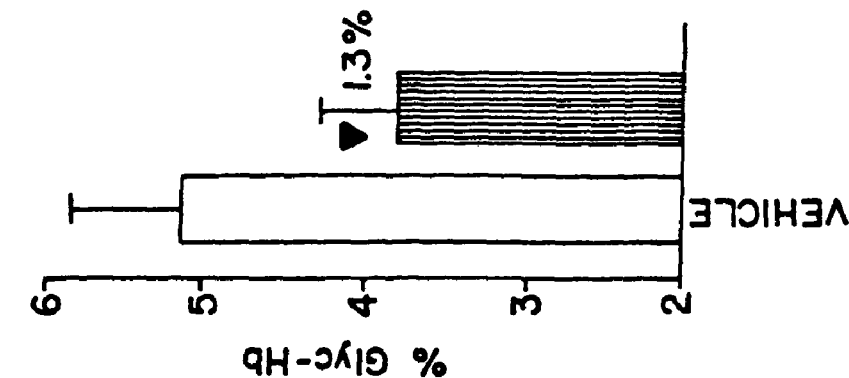
FIGS. 6A, 6B, 6C and 6D are graphs showing the serum insulin levels, triglyceride levels, free fatty acid levels and Glyc-Hb levels of serum of ob/ob mice treated with a compound according to the present invention.

The triglyceride levels were also measured. Triglycerides, which are esters of fatty acids and glycerol, do not freely circulate in plasma but are bound to proteins and transported as macromolecular complexes called lipoproteins. The triglycerides were measured by the enzymatic method described by McGowan et al., Clin Chem 29:538-42, 1983, with a modification to determine the triglyceride levels in db/db and ob/ob mice. There was shown a 24% drop in triglyceride levels in db/db mice (FIG. 5A) after 15 days of treatment with the compound and in ob/ob mice, a 65% decrease in triglyceride as compared to the control (FIG. 6B) after treatment for 10 days.

Figure 6C:
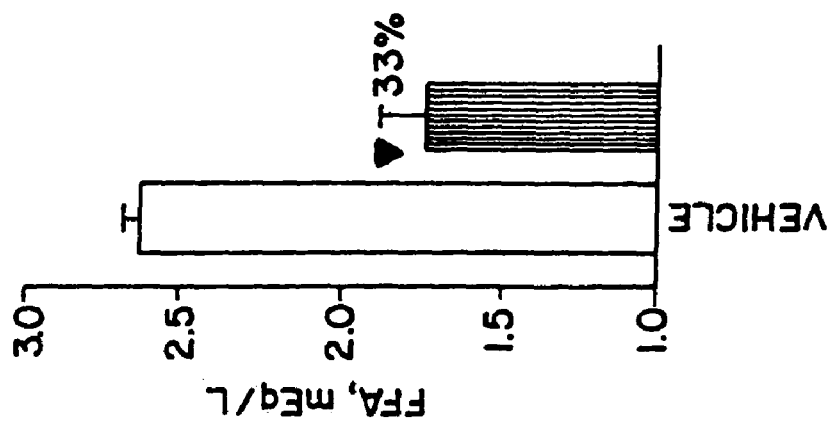
Figure 6B:

The free fatty acids (FFA) were enzymatically measured using coenzyme A in the presence of acyl CoA synthase (Wako Chemicals USA). The free fatty acid levels in db/db and ob/ob mice treated with the compound were significantly lower compared to the control animals. A 34% drop in FFA levels in db/db mice (FIG. 5B) was shown after 15 days of treatment with the compound. In ob/ob mice, after 10 days of treatment, a lowering of 33% of FFA was shown compared to the control (FIG. 6C).

Figure 6A:
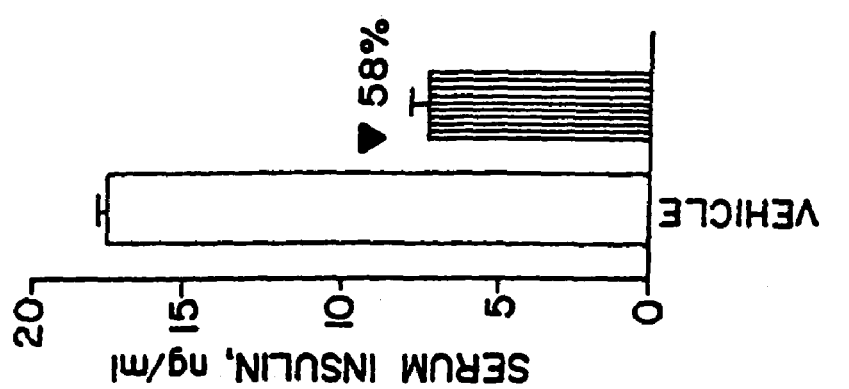

The percentage of glycohemoglobin (GHb) in blood reflects the average blood glucose concentration. It is a measure of overall diabetic control and can be use to monitor the average blood glucose levels. The glycosylation of hemoglobin occurs continuously in the red blood cells. But since the reaction is non-enzymatic and irreversible, the concentration of glycohemoglobin in a cell reflects the average blood glucose levels seen by the cell during its life. An assay was conducted using affinity chromatography with boronate as described by Abraham et al., *J. Lab. Clin. Med.*, 102, 187 (1983). There is a 0.7% drop in the GHb level in db/db mice (FIG. 5C) after 15 days of treatment with the compound and in ob/ob mice after 14 days of treatment, there is 1.3% decrease (FIG. 6D) in the GHb level compared to the control. The blood insulin level was measured by ELISA following a standard protocol. A 58% drop of serum insulin in ob/ob mice (FIG. 6A) was shown after 10 days of treatment with the compound, thus, demonstrating its ability to act as an insulin sensitizer.

Obesity is considered a significant risk factor for various adult diseases such as diabetes and cardiac disease. Leptin, an obese gene product, has been identified from the investigation of ob/ob mice, where the leptin is lacking because of a mutation in that gene (Zhiang et al., Nature, 372, 425 (1994). Leptin is a protein of about 16 kDa, which is expressed in adipose tissue, and which promotes weight loss by suppressing appetite and stimulating metabolism. It is currently believed that leptin plays a key role in the obesity syndrome. In the db/db mice according to the experiment, the leptin level was measured by an ELISA, following a standard protocol. After 15 days of treatment with the compound, there is a 23°/a increase (FIG. 5D) in the serum leptin level compared to the control group.

Figures 7A, 7B:
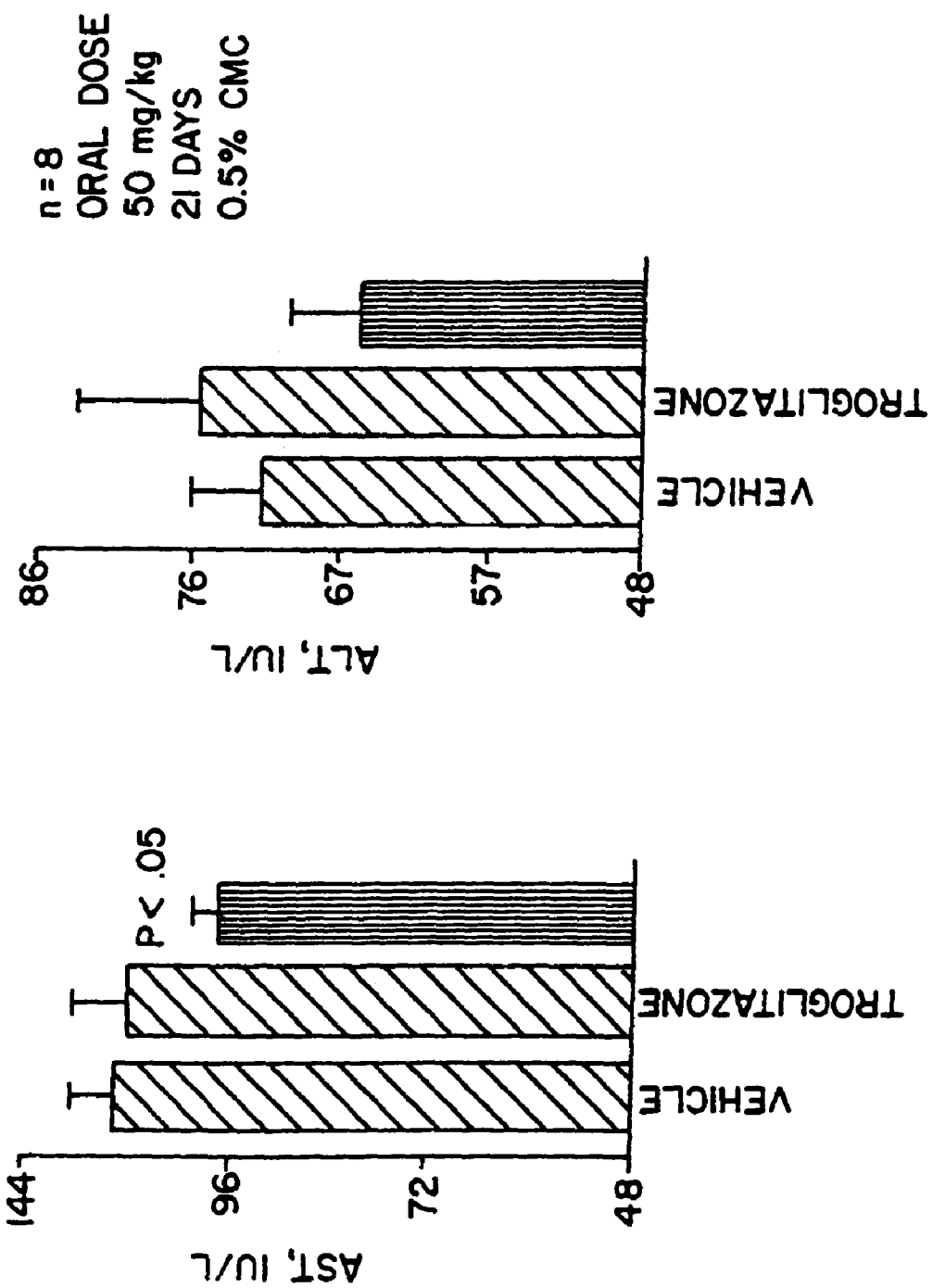
FIGS. 7A and 7B show the assays of liver enzymes in mice 21 days after treatment with a compound according to the invention.

The liver enzymes glutamic oxalacetic transaminase/aspartate aminotransferase (AST/GOT) and glutamic pyruvic transaminase/alanine aminotransferase (ALT/GPT) were assayed in the sera of ob/ob mice after 21 days of treatment (orally, 50 mg/kg) of the test compound. The test was also conducted using troglitazone. These enzyme levels are found to elevate in several kinds of hepatic disorders or liver necrosis. In FIG. 7A, the AST level in the mice was not elevated compared to untreated mice or to mice treated with troglitazone. Similarly, FIG. 7B shows that the ALT level did not elevate compared to untreated mice or mice treated with troglitazone.

Figure 8:
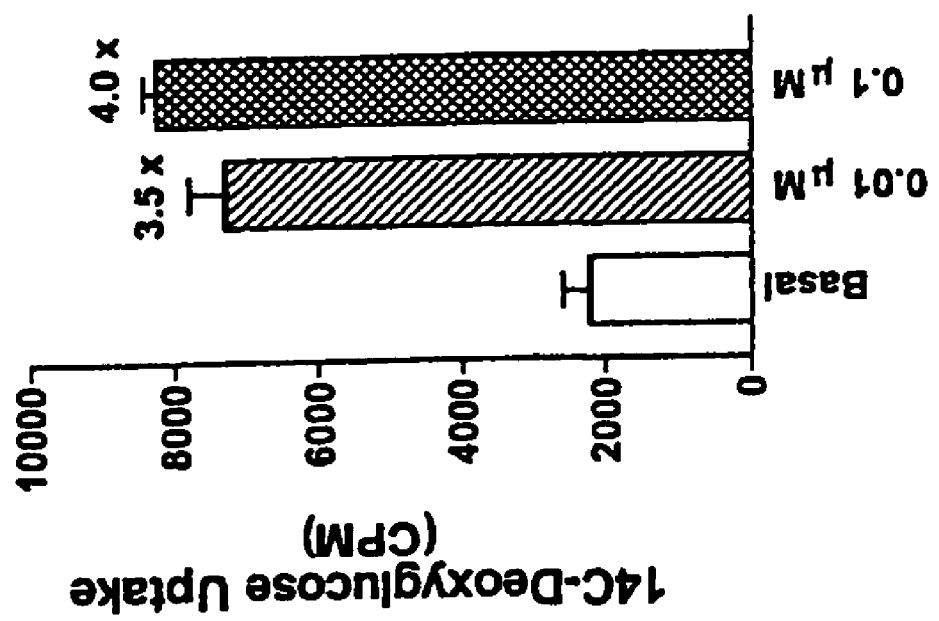
FIG. 8 shows glucose uptake in 3T3-L1 cells for a compound of the invention.

Referring to FIG. 8 glucose uptake in 3T3-L1 differentiated adipocytes was measured after treatment with the test compound. The assay was conducted according to the method of Tafuri, *Endocrinology*, 137, 4706-4712 (1996). The serum-starved cells were treated with the test compound for 48 hours at different concentrations, then washed and incubated in glucose-free media for 30 minutes at 37° C. Then $^{14}$C-deoxyglucose was added and uptake was monitored for 30 minutes under incubation. After washing, the cells were lysed (0.1% SIDS) and counted. As shown in FIG. 8, there is a 3.5 to 4-fold increase in glucose uptake at the indicated concentrations of the test compound with respect to basal levels.

Figure 9:
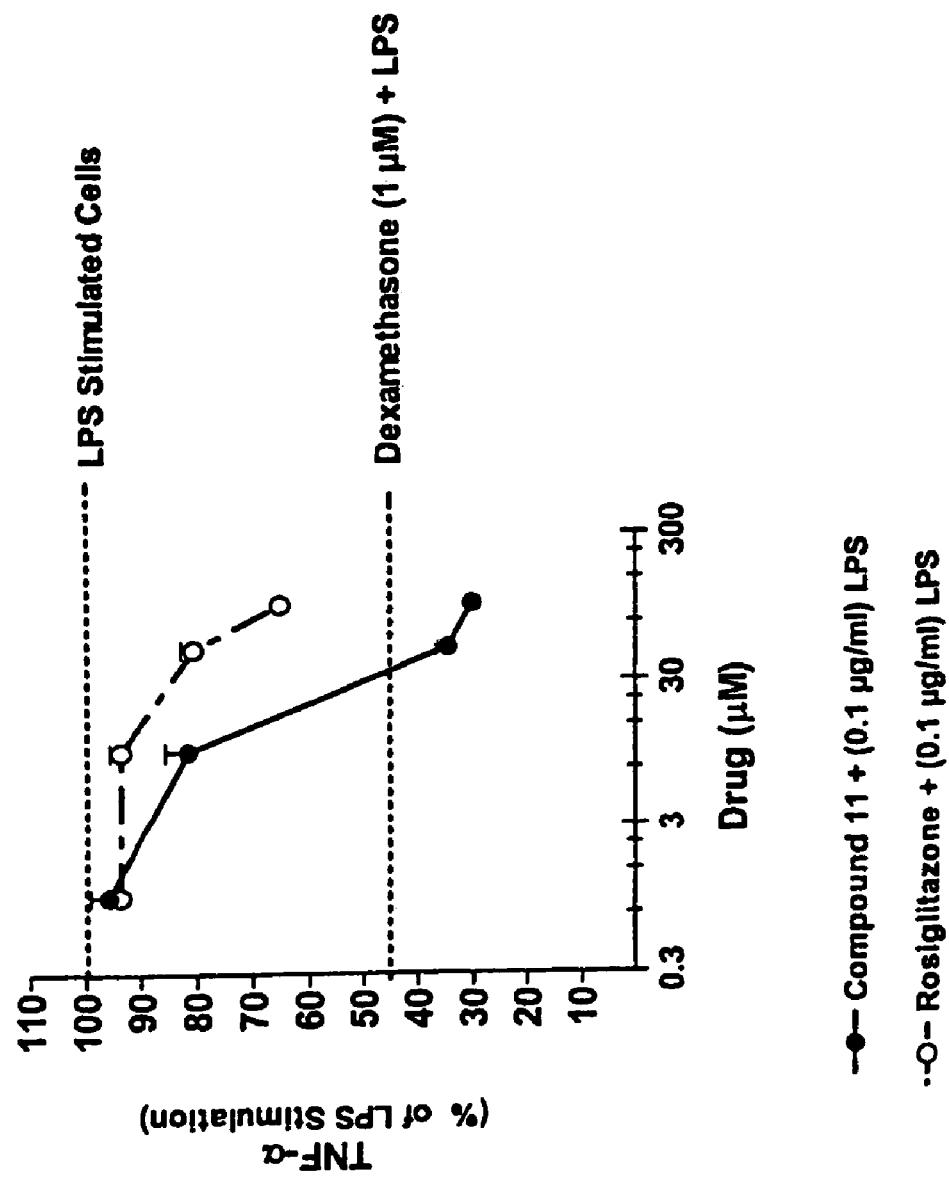
FIG. 9 shows a graph of the comparison of a compound of the invention with rosiglitazone for inhibition of LPS-induced TNF production.

Referring to FIG. 9, RAW cells were preincubated with either compound 11 or rosiglitazone (0.1, 1, 10, 50 or 100 pM) for 1 hour at 37° C. in RPMI-1640 containing 10% FBS. After 1 hour, LIPS (0.1 pg/ml) was added and cells were incubated an additional 6 hours. Cell supernatant was then collected, aliquoted and frozen at −70° C., and an aliquot used to determine TNF-alpha concentration by ELISA. Compound 11 was a better inhibitor of TNF-alpha than rosiglitazone.

Figure 10:
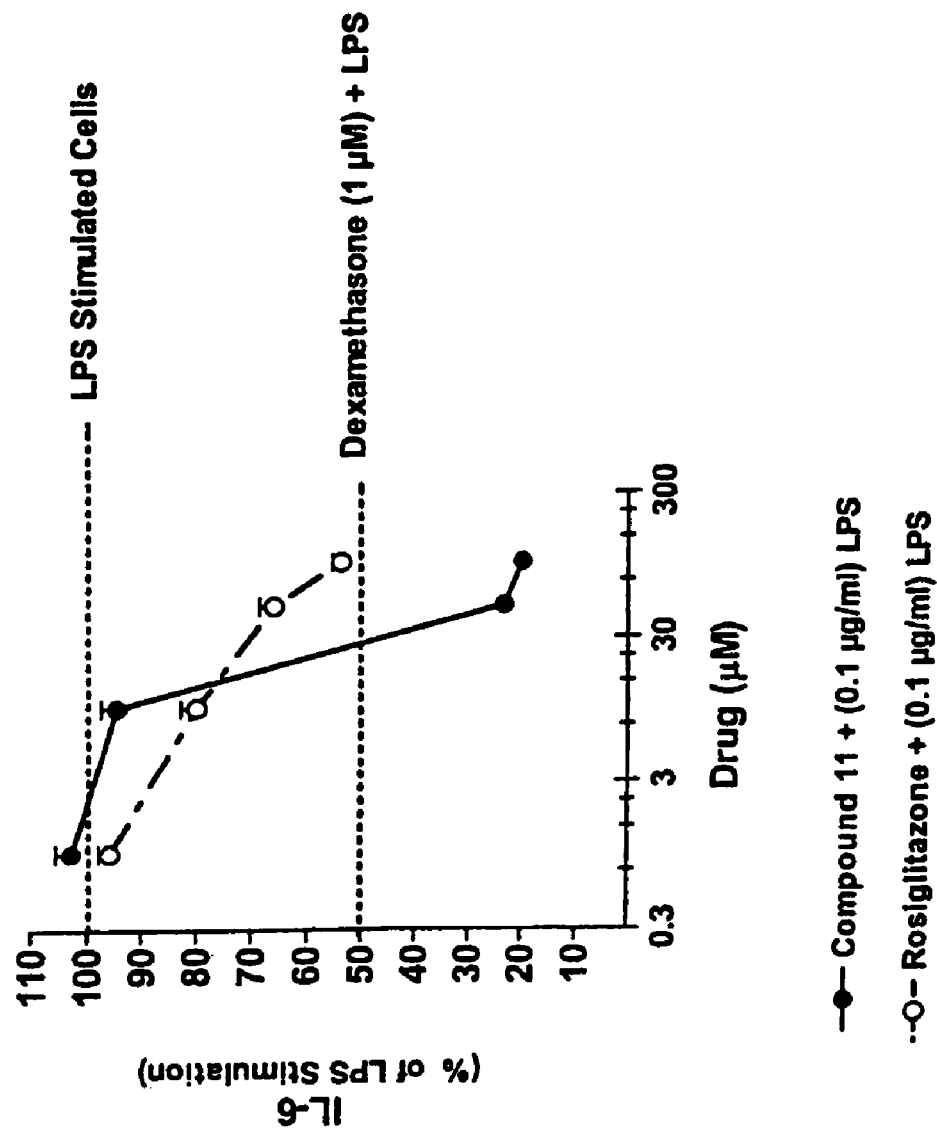
FIG. 10 is a graph of the comparison of a compound of the invention with rosiglitazone for inhibition of LPS-induced IL-6 production.

Referring to FIG. 10, RAW cells were preincubated with either compound 11 or rosiglitazone (0.1, 1, 10, 50 or 100 pM) for 1 hour at 37° C. in RPMI-1640 containing 10% FBS. After 1 hour LIPS (0.1 pg/ml) was added and cells were incubated an additional 6 hours. Cell supernatant was then collected, aliquoted and frozen at −70° C., and an aliquot used to determine the concentration of IL-6 by ELISA. Compound 11 was a better inhibitor of IL-6 than rosiglitazone.

Figure 11:
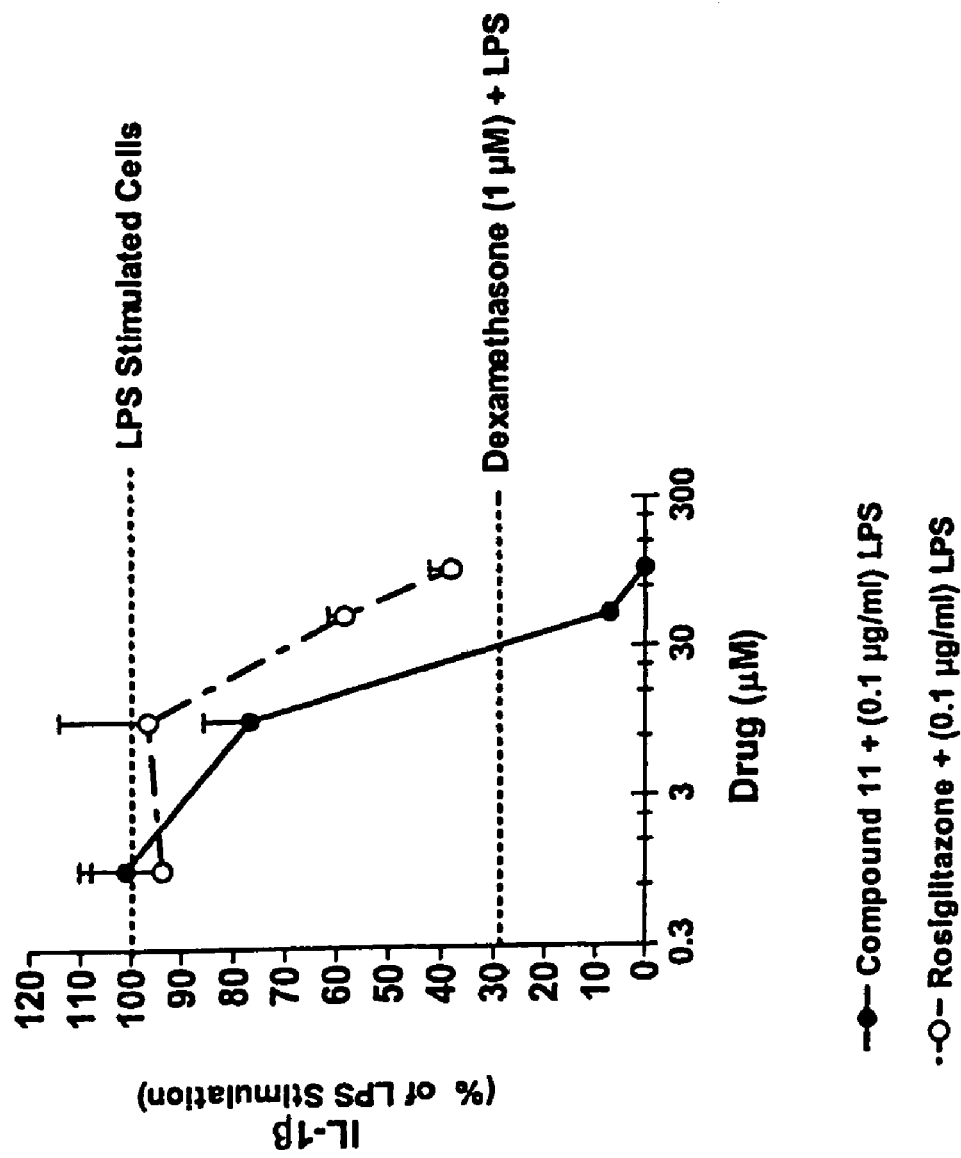
FIG. 11 is a graph of the comparison of a compound of the invention with rosiglitazone for inhibition of LPS-induced IL-1-beta production.

Referring to FIG. 11, RAW cells were preincubated with either compound 11 or rosiglitazone (0.1, 1, 10, 50 or 100 pM) for 1 hour at 37° C. in RPM 1-1640 containing 10% FIBS. After 1 hour LPS (0.1 pg/mL) was added and cells were incubated an additional 6 hours. Cell supernatant was then collected, aliquoted and frozen at −70° C., and an aliquot used to determine the concentration of IL-1-beta by ELISA. Compound 11 inhibited IL-1-beta better than rosiglitazone.

Figures 12A, 12B:
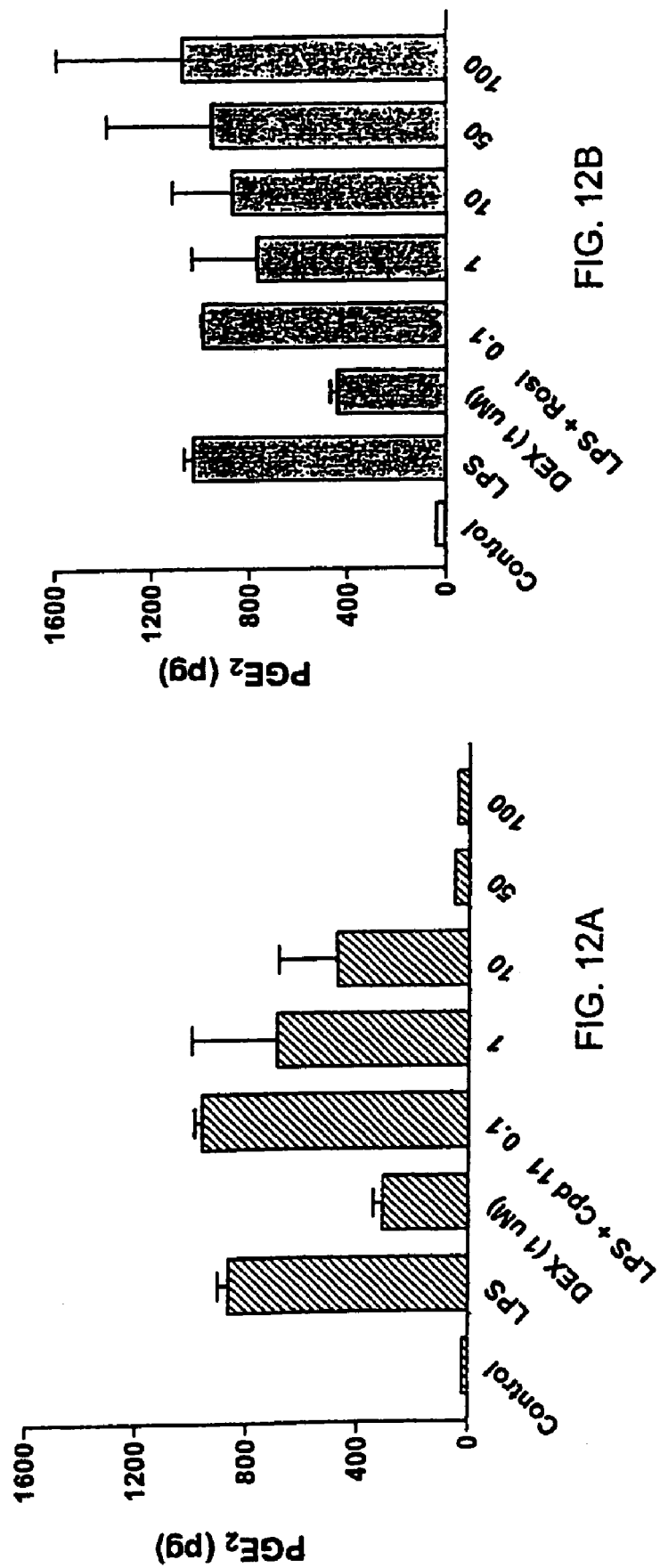
FIGS. 12A and 12B show a comparison of a compound of the invention (FIG. 12A) with rosiglitazone (FIG. 12B) for inhibition of LPS-induced COX-2 activity.
Figure 13:
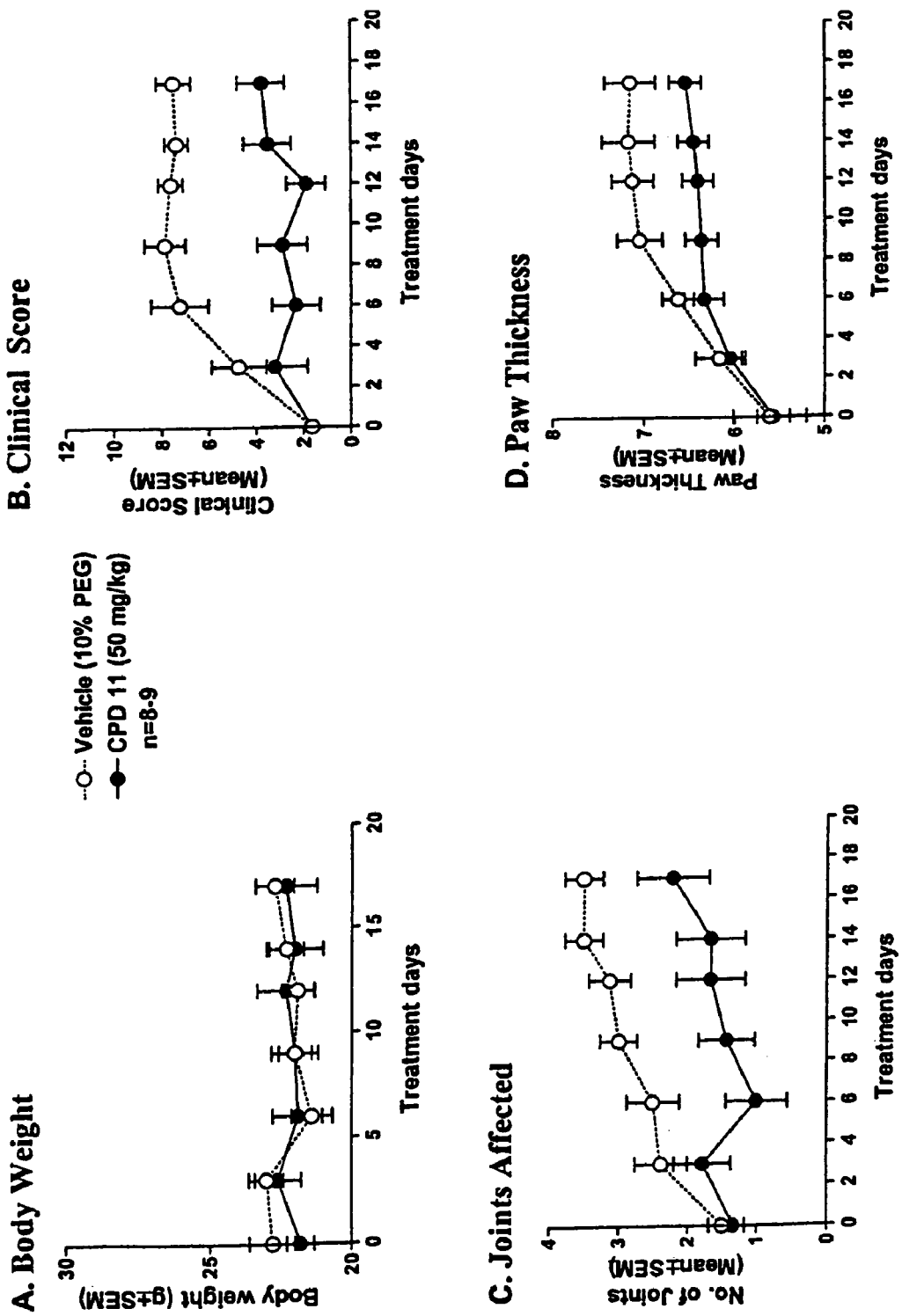
FIGS. 13A, 13B, 13C and 13D illustrate the suppression of collagen-induced arthritis by using a compound according to the invention.

Referring to FIGS. 12A AND 12B, RAW cells were preincubated with either compound 11 (12A) or rosiglitazone (12B) (0.1, 1.0, 10, 50 or 100 µM) for 1 hour at 37° C. in RPMI-1640 containing 10% FIBS. After 1 hour LPS (0.1 pg/mL) was added and cells were incubated an additional 6 hours. Cell supernatant was then collected, aliquoted and frozen at −70° C., and aliquots used to determine COX-2 and COX-1 activity. Compound 11, but not rosiglitazone, inhibited the activity of COX-2 (as measured by PGE2 production in a 50 µl sample). Neither compound inhibited COX-1 activity.

The transcription factor NF-kappaB coordinates the activation of many genes involved in the response to pro-inflammatory cytokines, and, therefore, plays a key role in the development of inflammatory diseases. NF-kappaB is activated by phosphorylation of the inhibitory protein IkappaB. To examine the effect of compound 11 on the LPS-stimulated phosphorylation of IkappaB, RAW 264.7 cells were preincubated with vehicle only, 15-deoxy-$\Delta^{12,14}$-prostaglandin J2 ($15dPGJ_2$) (3 pM) as a positive control, compound 11 (3, 10 or 30 pM), or rosiglitazone (3, 10 or 30 µM) for 1 hr. at 37° C. Then, cells were treated with or without LPS (10 µg/mL) plus IFN-gamma (10 U/mL) for 5 min. or 15 min. at 37° C. Cells were then lysed, and the cell lysates (27 µg/lane) were separated by electrophoresis on a 4-20% polyacrylamide gel, blotted onto a nitrocellulose membrane and probed with anti-phospho-IkappaB antibody. The results revealed that compound 11, but not rosiglitazone, exhibited dose-dependent inhibition of the phosphorylation of IkappaB.

To further confirm the ability of Compound 11 to inhibit the activation of NF-kB, the production of free p65 (activated) NF-kB in LPS-stimulated cells was measured. RAW cells were seeded at $5 \times 10^5$/well in 6-well plates at 37° C. overnight in 10% FBS complete medium. Cells were washed 2× with 0.5% FBS medium and then pretreated with 10 µM of Compound 11, rosiglitazone, or $15dPGJ_2$ at 37° C. for 1 hr. After pretreatment, cells were incubated with 0.5% FBS medium or stimulated with 1 µg/ml LPS at 37° C. for 15 min. After being washed 3× with cold PBS, cells were lysed to generate whole cell lysates. The protein concentrations were determined and 5 µg protein of whole cell lysate was used to determine the NF-kB p65 activity for each sample using a commercial ELISA kit (Active Motif, Carlsbad, Calif.). In this ELISA, micro-well plates are coated with an oligonucleotide containing the consensus binding site for NF-kB. After addition of the cell lysate, DNA-bound transcription factor is detected using anti-p65 antibodies. Two wells of each sample were assayed and the mean of two ELISA readings for each sample was determined. The specificity of the binding was checked by subsequent addition of 20 µmol of wild-type consensus oligonucleotide to each well.

Figure 15:
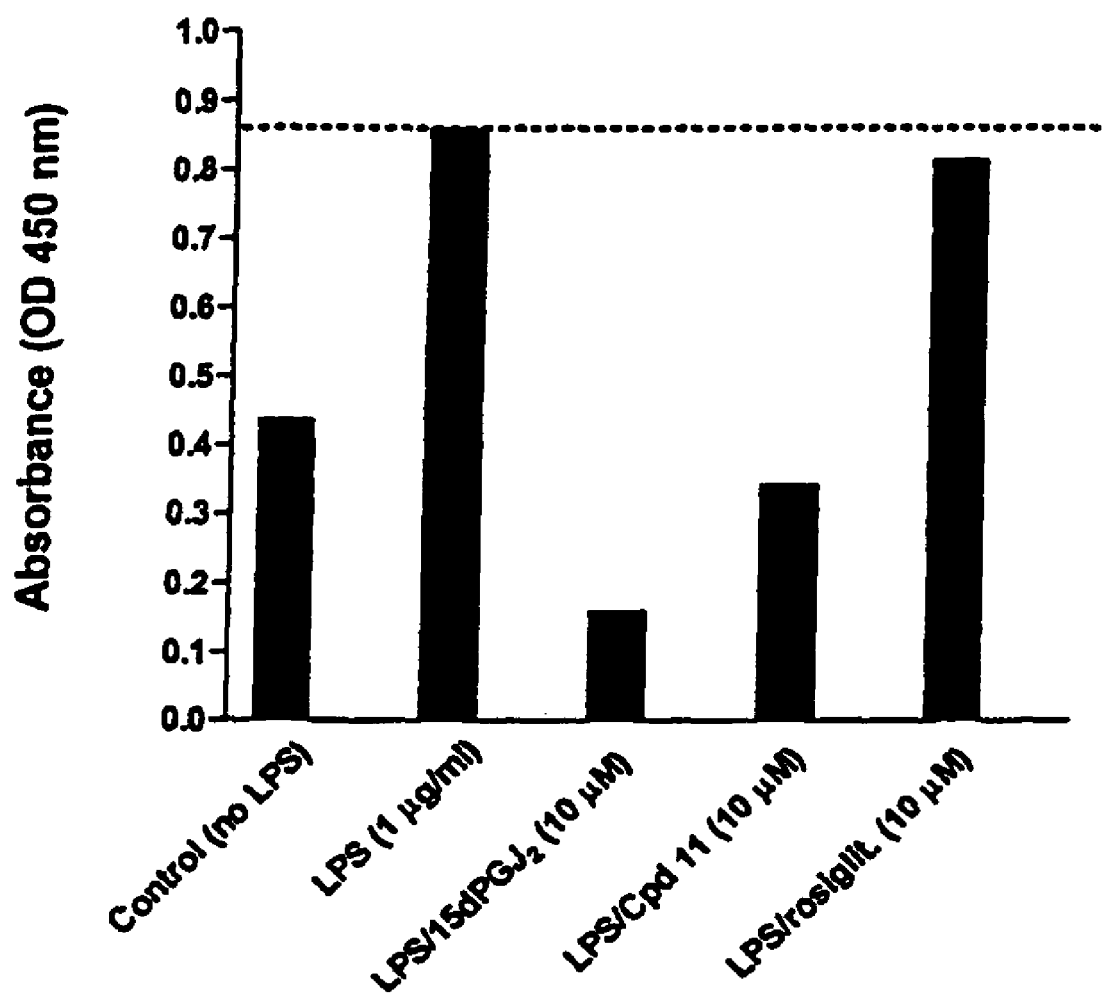
FIG. 15. NF-kB activation in stimulated RAW 264.7 cells.

As shown in FIG. 15, both Compound 11 and $15dPGJ_2$ inhibited the activation of NF-kB. By contrast, rosiglitazone, a strong agonist of PPAR-gamma, did not inhibit the production of p65 transcription factor.

FIGS. 13A-D illustrate the suppression of collagen-induced arthritis by treatment with Compound 11. Arthritis was induced by intradermal administration of collagen (100 µg/mouse) in complete adjuvant in make DBA/1 Lac mice of 7 weeks. The booster (100 µg/mouse) immunization in incomplete adjuvant was given subcutaneously on Day-21. Two days later when arthritic scores were around 1, the animals were divided into two groups. One group received 50 mg/kg dose of Compound 11 orally for 17 days daily. The second group received 10% PEG in water and was used as a vehicle treated group. Body weight (FIG. 13A), Clinical score (FIG. 13B), Joints affected (FIG. 13C) and Paw thickness (FIG. 13D) were monitored 24 hours after the drug administration at different time intervals. As shown in the Figures, the mice treated with Compound 11 showed significantly lower clinical scores, joints affected and paw thickness when compared to the vehicle treated group. There was no change in body weight between the vehicle and the treatment groups.

Figure 14:
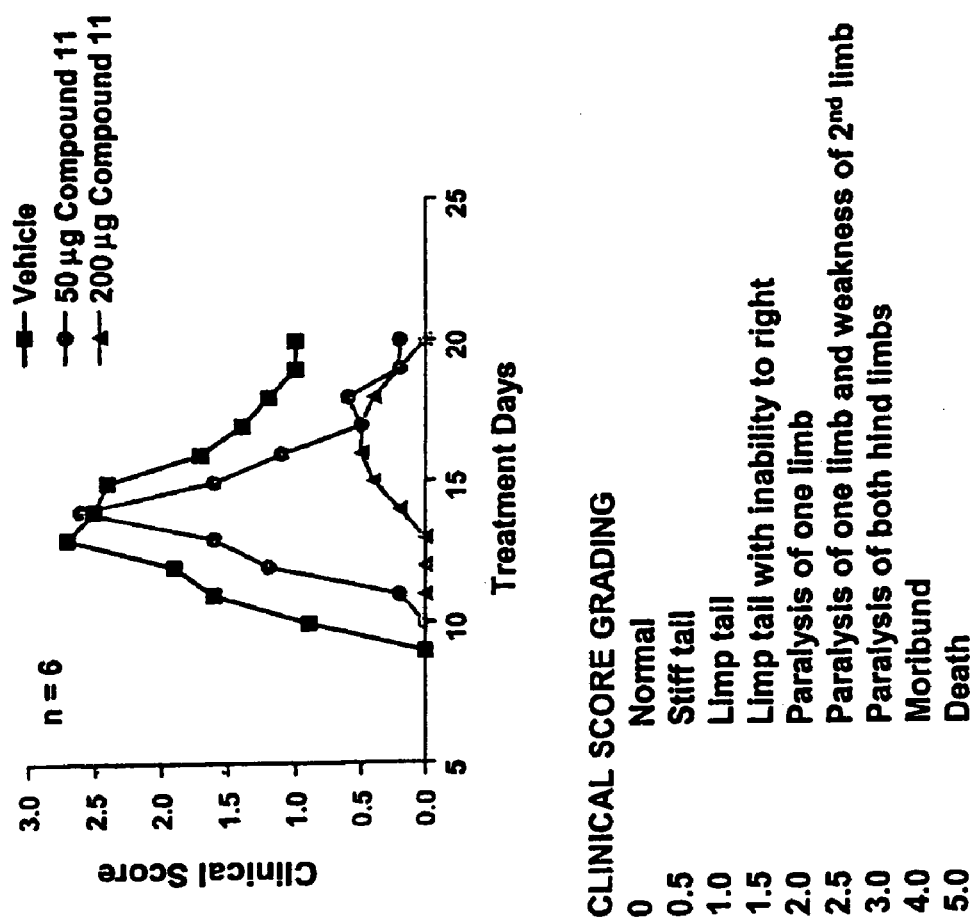
FIG. 14 illustrates the suppression of experimental allergic encephalomyelitis (EAE) by using a compound according to the invention.

Experimental allergic encephalomyelitis (EAE) is an autoimmune demyelinating inflammatory disease of the central nervous system. EAE exhibits many of the clinical and pathological manifestations of human multiple sclerosis (MS), and it serves as an animal model to test potential therapeutic agents for MS (Scolding et al, *Prog Neurobiol*, 43:143-73, 2000). FIG. 14 illustrates the suppression of EAE by Compound 11. Active EAE was induced in SJL-/J mice essentially according to the method of Owens and Sriram (*Neurol Clin*, 13:51-73, 1995). Naive mice were immunized subcutaneously with 400 pg each of mouse spinal cord homogenate in complete Freund's adjuvant on day 0 and day 7. Mice were then treated once daily by subcutaneous injection with 50 µg or 200 µg of compound 11 or with vehicle only. Paralysis was graded according to the numeric scale indicated. As evidenced by the dramatic reduction in clinical score shown in FIG. 14, treatment with the 200 µg dose of compound 11 was highly effective in ameliorating EAE.

It will be evident from the above that the compounds according to the present invention, as represented by compound 11, not only lower blood glucose level, triglyceride level, free fatty acid level, glycohemoglobin and serum insulin, but also raise the leptin level while showing no significant increase in body weight or liver toxicity. The compounds also inhibit INF-alpha, IL-6, IL-1-beta production and COX-2 activity in vitro and, as shown by FIGS. 13A-13D and 14, the compounds can be used to suppress arthritis and potentially to treat multiple sclerosis, respectively. The properties demonstrated above indicate that the compounds of the invention should be useful in the treatment of disorders associated with insulin resistance, hyperlipidemia, coronary artery disease and peripheral vascular disease and for the treatment of inflammation, inflammatory diseases, immunological diseases and cancer, especially those mediated by cytokines and cyclooxygenase.

While the invention has been exemplified above by reference to the preparation and use of compound 11, it will be understood that the invention is of broader application consistent with the scope of compounds represented by formula 1. This includes, for example, compound 10, which is not only useful as an intermediate for preparing compound 11 as shown but also demonstrates useful biological activity of its own consistent with the activities of compound 11.

The synthesis of other compounds representative of the scope of the invention is illustrated by the examples which follow:

EXAMPLE 2

3-(3,5-Dimethoxyphenyl)-2-{4-[4-(2,4-dioxothiazolidin-5-ylmethyl)-phenoxy]-phenyl}-acrylamide (24)

Compound 24, which may be represented by the formula:

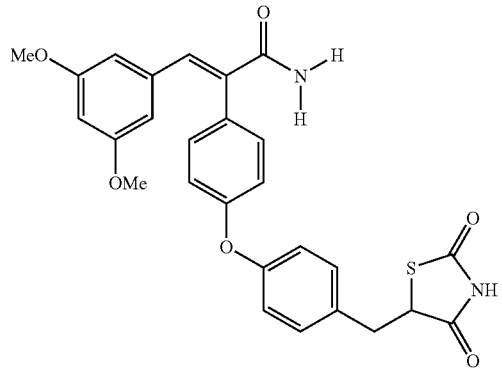

was prepared as follows from compound 14. A clean dry flask with stirbar was charged with compound 14 (0.423 g, 0.837 mmol) and dry DMF (10 mL). Then with stirring carbonyldiimidazole (0.271 g, 1.67 mmol) was added and the reaction was heated to 60° C. for 1 h. while vented through an oil-bubbler. The reaction mixture was then cooled to 0° C. and 2M ammonia in methanol (2.1 mL, 4.2 mmol) was added. The reaction was worked up by partitioning the mixture with 10% citric acid (10 mL), ethyl acetate (50 mL), and water (40 mL). The organic phase was then rinsed sequentially with water (2×30 mL), brine (1×20 mL) and dried with anhydrous MgSO$_4$. Concentration of the organics afforded crude product. The crude product was purified by silica gel chromatography using ethyl acetate-hexanes (1:1) containing 1% acetic acid to ethyl acetate-hexanes (3:2) containing 1% acetic acid gradient elution. Concentration of the appropriate fractions yielded 200 mg (47%) of the white-light yellow primary amide as a solid. Analysis: $^1$H NMR, 400 MHz (DMSO-d$_6$): δ12.06 (br, 1H), 7.40 (s, 1H), 7.34 (br, 1H), 7.27 (d, J=8.4 Hz, 2H), 7.18 (d, J=8.8 Hz, 2H), 7.05 (d, J=9.2 Hz, 2H), 6.98 (d, J=8.4 Hz, 2H), 6.93 (br, 1H), 6.36 (m, 1H), 6.20 (s, 1H), 6.19 (s, 1H), 4.91 (dd, J=4.0 Hz, 1H), 3.57 (s, 6H), 3.12 (dd, J=9.2 Hz, 1H).

EXAMPLE 3

3-(3,5-Dimethoxyphenyl)-2-{4-[4-(2,4-dioxothiazolidin-5ylmethyl)phenoxy]-phenyl}-N,N-dimethylacrylamide (25)

Compound 25, represented by the formula:

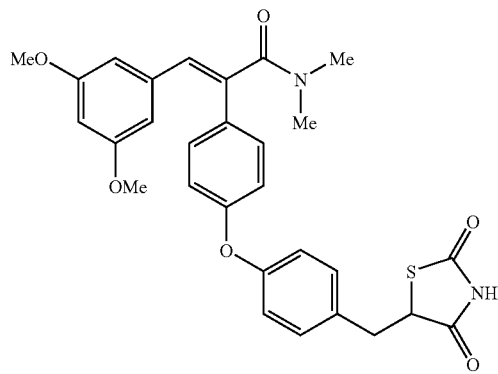

was prepared as follows: A clean dry flask with stirbar was charged with compound 14 (0.422 g, 0.835 mmol) and dry DMF (1 mL). Then with stirring carbonyldiimidazole (0.271 g, 1.67 mmol) was added and the reaction was heated to 60° C. for 1 h. while vented through an oil-bubbler. The reaction mixture was then cooled to 0° C. and a 2M dimethylamine in THF (2.1 mL, 4.2 mmol) solution was added. The reaction was worked up by partitioning the mixture with 10% citric acid (10 mL), ethyl acetate (50 mL), water (40 mL). The organic phase was then rinsed sequentially with water (2×30 mL), brine (1×20 mL) and dried with anhydrous MgSO$_4$. Concentration of the organics afforded crude product. The crude product was purified by silica gel chromatography using ethyl acetate-hexanes (3:2) containing 1% acetic acid elution. Concentration of the fractions yielded 381 mg (86%) of the off-white tertiary dimethylamide as a solid. Analysis: $^1$H NMR, 400 MHz (DMSO-d$_6$): δ11.97 (br, 1H), 7.29 (d, J=8.8 Hz, 2H), 7.27 (d, J=8 Hz, 2H), 6.99 (d, J=8.8 Hz), 6.95 (d, J=8.8 Hz, 2H), 6.57 (s, 1H), 6.35 (m, 1H), 6.29 (s, 1H), 6.28 (s, 1H), 4.91 (dd, J=4.4 Hz, 1H), 3.58 (s, 6H), 3.12 (dd, J=9.2 Hz, 1H), 3.05 (br, 3H), 2.91 (s, 3H).

EXAMPLE 4

3-(3,5-Dimethoxyphenyl)-2-{4-[4-(2,4-dioxothiazolidin-5-ylmethyl)-phenoxy]-phenyl}-N-methoxy,—N-methylacrylamide (compound 26)

Compound 26 may be structurally shown as follows:

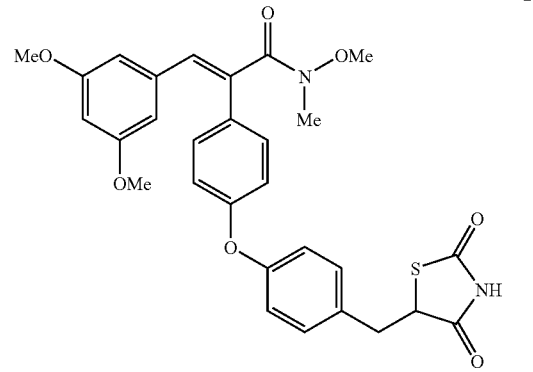

was prepared as follows. A clean dry flask with stirbar was charged with compound 14 (0.450 g, 0.890 mmol) and dry DMF (1 mL). Then, with stirring, carbonyldiimidazole (0.29 g, 1.78 mmol) was added and the reaction was heated to 60° C. for 1 h. while vented through an oil-bubbler. The reaction mixture was then cooled to 0° C. and N-methyl-N-methoxy-hydroxylamine hydrochloride (0.434 g, 4.45 mmol) in water (1 mL) and triethylamine (0.62 mL) was added and stirred overnight. The reaction was worked up by partitioning the mixture with 10% citric acid (10 mL), ethyl acetate (50 mL), and water (40 mL). The organic phase was then rinsed sequentially with water (2×30 mL), brine (1×20 mL) and dried with anhydrous magnesium sulfate. Concentration of the organics afforded crude product. The crude product was purified by silica gel chromatography using ethyl acetate-chloroform (1:5) elution. Concentration of the appropriate fractions yielded 400 mg (82%) of the off-white tertiary N-methyl-N-methoxyamide as a solid. Analysis: $^1$H NMR, 400 MHz (DMSO-d6): δ12.06 (br, 1H), 7.27 (d, J=9.2 Hz, 2H), 7.26 (d, J=8.8 Hz, 2H), 7.00 (d, J=8.8 Hz), 6.95 (d, J=8.4

Hz, 2H), 6.57 (s, 1H), 6.35 (m, 1H), 6.29 (s, 1H), 6.28 (s, 1H), 4.91 (dd, J=4.4 Hz, 1H), 3.58 (s, 6H), 3.12 (dd, J=9.2 Hz, 1H), 3.05 (br, 3H), 2.91 (s, 3H).

EXAMPLE 5

The Syntheses Shown in this Example are Illustrated in Scheme 6.

2-(4-Acetoxyphenyl)-3-p-tolylacrylic acid (37). To a mixture of (4-hydroxyphenyl)-acetic acid (18.3 g, 120.3 mmol) and 4-methylbenzaldehyde (12.0 g, 100 mmol) in 250 mL acetic anhydride was added potassium carbonate (11.9 g, 121.2 mmol). The reaction mixture was stirred at 80° C. for 16 h before it was cooled to room temperature. To the mixture was added 100 mL $H_2O$, 5% HCl in water to pH 1 and 200 mL ethyl acetate. The mixture was then heated to 80° C. until all ethyl acetate was evaporated. The precipitate was filtered and washed with water and hexane. The filter cake was recrystallized out of toluene, filtered, washed with hexane and dried under vacuum to yield a pale yellow powder (20.16 g, 68.1%). $^1$H NMR (400 MHz, DMSO-$d_6$) δ 12.62 (br s, 1H), 7.74 (s, 1H), 7.19 (d, J=8.8 Hz, 2H), 7.13 (d, J=8.8 Hz, 2H), 7.01 (d, J=8.0 Hz, 2H), 6.94 (d, J=8.4 Hz, 2H), 2.29 (s, 3H), 2.23 (s, 3H).

2-(4-Hydroxyphenyl)-3-p-tolylacrylic acid (38). To a solution of compound 37 (20.16 g, 68.1 mmol) in 100 mL THF was added a solution of lithium hydroxide (5.7 g, 237.5 mmol) in 100 mL water. The reaction was allowed to stir at room temperature for 16 h after which 5% HCl in water was added to pH=1. The yellow solid was filtered and recrystallized out of toluene, washed with hexane and dried under vacuum to yield a white solid (14.27 g, 82.5%). $^1$H NMR (400 MHz, DMSO-$d_6$) δ 12.46 (br s, 1H), 9.47 (br s, 1H), 7.63 (s, 1H), 7.02 (d, J=8.0 Hz, 2H), 6.97 (d, J=8.4 Hz, 2H), 6.93 (d, J=8.4 Hz, 2H), 6.74 (d, J=8.8 Hz, 2H), 2.22 (s, 3H).

2-[4-(4-Formylphenoxy)-phenyl]-3-p-tolylacrylic acid (39). To a solution of 38 (7.27 g, 28.6 mmol) and potassium carbonate (8.68 g, 62.9 mmol) in 200 mL N,N-dimethylacetamide was added 4-fluorobenzaldehyde (3.9 mL, 36.4 mmol). The reaction mixture was heated to 190° C. for 1.5 h under argon then cooled to room temperature. The addition of 5% HCl in water to pH 1 resulted in the product separating out as oil. Approximately 50 mL ethyl acetate was added to the mixture which is allowed to stir 16 h. The solid was collected and recrystallized out of toluene, rinsed with hexane and dried under vacuum to yield a white powder (8.1 g, 79.0%). $^1$H NMR (400 MHz, DMSO-$d_6$) δ 12.71 (s, 1H), 9.94 (s, 1H), 7.97 (d, J=8.8 Hz, 2H), 7.76 (s, 1H), 7.25 (d, J=8.4 Hz, 2H), 7.18 (d, J=6.8 Hz, 2H), 7.16 (d, J=6.4 Hz, 2H), 7.07 (d, J=8.0 Hz, 2H), 6.98 (d, J=8.4 Hz, 2H), 2.25 (s, 3H).

2-{4-[4-(2,4-Dioxothiazolidin-5-ylidenemethyl)-phenoxy]-phenyl}-3-p-tolylacrylic acid (40). To a solution of 39 (4.0 g, 11.2 mmol), thiazolidine-2,4-dione (1.31 g, 11.2 mmol), and benzoic acid (1.64 g, 13.4 mmol) in 100 mL toluene was added piperidine (1.66 mL, 16.8 mmol). The mixture was vigorously refluxed with Dean Stark apparatus for 1.5 h under argon then cooled to room temperature. 5% HCl was added to pH 1. The solid was filtered, recrystallized out of toluene, filtered, and washed with hexane before drying under vacuum to a yellow solid (quantitative). $^1$H NMR (400 MHz, DMSO-$d_6$) δ 12.70 (br s, 1H), 12.59 (br s, 1H), 7.80 (s, 1H), 7.75 (s, 1H), 7.67 (d, J=8.8 Hz, 2H), 7.22 (d, J=9.2 Hz, 2H), 7.18 (d, J=7.6 Hz, 2H), 7.12 (d, J=9.2 Hz, 2H), 7.07 (d, J=8.0 Hz, 2H), 6.99 (d, J=8.0 Hz, 2H), 2.25 (s, 3H).

2-{4-[4-(2,4-Dioxothiazolidin-5-ylmethyl)-phenoxy]-phenyl}-3-p-tolylacrylic acid (41). To a solution of 40 (1.0 g, 2.2 mmol) and ammonium formate (8.32 g, 132 mmol) in 25 mL glacial acetic acid was added 5% Pd/C (1.0 g). The mixture was refluxed for 7.5 h, cooled to room temperature and filtered over Celite. The mixture was concentrated in vacuum then added to 200 mL water. The product was filtered and washed with hexanes. The solid was recrystallized out of toluene, cooled to room temperature and sonicated until the solid was observed. The mixture was then stirred at room temperature for 16 h. The precipitate was collected and washed with hexanes to yield a white solid (0.609 g, 59.1%). $^1$H NMR (400 MHz, DMSO-$d_6$) δ 12.65 (s, 1H), 12.05 (br s, 1H), 7.72 (s, 1H), 7.30 (d, J=8.8 Hz, 2H), 7.16 (d, J=8.4 Hz, 2H), 7.05 (d, J=8.4 Hz, 2H), 7.01 (d, J=8.4 Hz, 2H), 6.99 (d, J=9.2 Hz, 2H), 6.98 (d, J=8.0 Hz, 2H), 4.92 (dd, J=4.4 and 9.6 Hz, 1H), 3.38 (dd, J=4.4 and 14.0 Hz, 1H), 3.21 (dd, J=9.2 and 14.0 Hz, 1H), 2.24 (s, H).

2-{4-[4-(2,4-Dioxothiazolidin-5-ylmethyl)-phenoxy]-phenyl}-3-p-tolylacrylic acid methyl ester (42). To a mixture of 41 (0.1 g, 0.218 mmol) and BOP [Castro's Reagent, Benzotriazole-1-yl-oxy-tris-(dimethylamino)-phosphonium hexafluorophosphate] (0.144 g, 0.326 mmol) in 5 mL dichloromethane was added triethylamine (0.067 mL, 0.477 mmol). The mixture was stirred for 1 h, and then sodium methoxide (0.5 M solution in methanol, 0.07 mL, 0.035 mmol) was added with 5 mL MeOH. The reaction was allowed to stir at room temperature for 16 h. 5% HCl was added to pH 0 and the mixture was extracted with 25 mL dichloromethane three times. The combined organic layers were washed with brine, dried over $MgSO_4$, filtered and concentrated. The residue was loaded onto silica gel column as a solution in dichloromethane. The product was eluted with hexanes-ethyl acetate (3:2). Fractions were concentrated in vacuum to a white solid (0.037 g, 36.4%). $^1$H NMR (400 MHz, DMSO-$d_6$) δ 12.05 (br s, 1H), 7.75 (s, 1H), 7.30 (d, J=8.8 Hz, 2H), 7.18 (d, J=8.8 Hz, 2H), 7.06 (d, J=8.0 Hz, 2H), 7.02 (d, J=8.8 Hz, 2H), 6.99 (d, J=8.8 Hz, 2H), 6.98 (d, J=8.0 Hz, 2H), 4.91 (dd, J=4.8 and 9.6 Hz, 1H), 3.72 (s, 3H), 3.39 (dd, J=4.0 and 13.6 Hz, 1H), 3.13 (dd, J=9.2 and 14.0 Hz, 1H), 2.25 (s, 3H).

EXAMPLE 6

The syntheses shown in this example are illustrated in Scheme 7.

3,5-dimethylbenzaldehyde (43). To a mixture of 3,5-dimethylbenzoic acid (7.51 g, 50 mmol) and triethylamine (21 mL, 150 mmol) in dichloromethane (200 mL) was added BOP reagent (22.11 g, 50 mmol). The solution was stirred at room temperature for 20 min and then N,O-dimethylhydroxylamine hydrochloride (5.0 g, 50 mmol) was added. After an additional 10 min, triethylamine (7 mL, 50 mmol) was added and the mixture was stirred for another 0.5 h. The solvent was removed in vacuo and the mixture was redissolved in ethyl acetate (300 mL), washed with 1N HCl (200 mL), 1N NaOH (200 mL), water, brine then dried ($MgSO_4$), filtered and concentrated in vacuo to yield a colorless syrup (6.25 g). This material was dissolved in THF (250 mL) and cooled to 0° C. under argon atmosphere. A solution of DIBAL [diisobutylaluminum hydride] (1M in THF, 50 mL) was added to the stirring solution over 5 min. After 20 min of stirring, additional DIBAL (20 mL) was added. After an additional 15 min, the reaction was quenched with careful addition of 1N HCl (300 mL) and the product was extracted into ethyl acetate (300 mL), washed with water (2×200 mL), brine (200 mL), dried ($MgSO_4$), filtered and concentrated in vacuo to yield 43 (4.97 g, 74% overall).

3-(3,5-Dimethylphenyl)-2-(4-hydroxyphenyl)-acrylic acid (44). To a mixture of 43 (3.23 g, 24 mmol), 4-hydroxyphenylacetic acid (3.66 g, 24 mmol) and potassium acetate (2.83 g, 28 mmol) was added acetic anhydride (100 mL). The mixture was heated to reflux for 4 h, cooled to room temperature, and then poured over water (400 mL). After stirring for 1.5 h, a solid gum settled to the bottom and the supernatant was decanted. To the residue was added THF (100 mL) and 1N NaOH (150 mL) and the mixture was stirred for 30 min. The mixture was acidified with 1N HCl (200 mL) and the product was extracted into ethyl acetate (300 mL), washed with water (300 mL), brine (300 mL), dried (MgSO$_4$), filtered and concentrated in vacuo. The crude solid was crystallized in toluene to yield 2.65 g (42%) of a pale yellow solid 44.

3-(3,5-Dimethylphenyl)-2-[4-(4-formylphenoxy)-phenyl]-acrylic acid (45). To a solution of 44 (2.65 g, 10 mmol) in DMF (20 mL) was added sodium hydride (60% dispersion in mineral oil, 0.88 g, 22 mmol). After gas evolution ceased 4-fluorobenzaldehyde (1.60 g, 15 mmol) was added and the reaction was stirred for 16 h. The mixture was poured over 10% citric acid (100 mL), after which a bright yellow solid formed. The solid was washed with water and then the wet solid was azeotroped and recrystallized from toluene to yield 2.97 g (80%) of a yellow solid 45.

3-(3,5-Dimethylphenyl)-2-{4-[4-(2,4-dioxothiazolidin-5-ylidenemethyl)-phenoxy]-phenyl}-acrylic acid (46). In a 100 mL round-bottomed flask equipped with a Dean-Stark apparatus, a mixture of 45 (1.55 g, 4.2 mmol), 2,4-thiazolidinedione (0.5 g, 4.2 mmol), benzoic acid (0.62 g, 5.0 mmol) and piperidine (0.62 mL, 6.3 mmol) was azeotroped in toluene (60 mL) for 45 min under vigorous reflux. The reaction mixture was cooled then poured over 10% citric acid (40 mL) and stirred until a bright yellow solid formed. The solid was filtered and washed with water and the wet solid was azeotroped and recrystallized from toluene to yield 1.83 g (93%) of 46. $^1$H NMR (400 MHz, DMSO-d$_6$): δ 12.72 (br s, 1H), 12.57 (br s, 1H), 7.77 (s, 1H), 7.70 (s, 1H), 7.63 (d, J=8.8 Hz, 2H), 7.22 (d, J=8.4 Hz, 2H), 7.14 (d, J=8.4 Hz, 2H), 7.12 (d, J=8.8 Hz, 2H), 6.92 (s, 1H), 6.69 (s, 2H), 2.16 (s, 6H).

3-(3,5-Dimethylphenyl)-2-{4-[4-(2,4-dioxothiazolidin-5-ylmethyl)-phenoxy]-phenyl}-acrylic acid (47). A mixture of 46 (1.83 g, 3.9 mmol), ammonium formate (4.90 g, 78 mmol) and 10% Pd on alumina (2.0 g) was refluxed for 15 h. The reaction mixture was cooled to room temperature and the catalyst was filtered off. Product was separated out with addition of water and the solid was filtered. The wet solid was azeotroped and recrystallized from toluene to yield 0.81 g (44%) 5. $^1$H NMR (400 MHz, DMSO-d$_6$): δ 12.68 (br s, 1H), 12.05 (br s, 1H), 7.68 (s, 1H), 7.27 (d, J=8.8 Hz, 2H), 7.16 (d, J=8.4 Hz, 2H), 7.02 (d, J=8.4 Hz, 2H), 6.96 (d, J=8.8 Hz, 2H), 6.90 (s, 1H), 6.62 (s, 2H), 4.92 (dd, J=8.8 and 4.4 Hz, 1H), 3.37 (dd, J=14.0 and 4.4 Hz, 1H), 3.12 (dd, J=14.0 and 8.8 Hz, 1H), 2.12 (s, 6H).

3-(3,5-Dimethylphenyl)-2-{4-[4-(2,4-dioxothiazolidin-5-ylmethyl)-phenoxy]-phenyl}-acrylic acid benztriazol-1-yl ester (48). To a mixture of 47 (0.81 g, 1.7 mmol) and N,N-diisopropylethylamine (0.33 mL, 1.9 mmol) in dichloromethane (20 mL) was added BOP reagent (0.76 g, 1.7 mmol). After 45 min of stirring at room temperature, the mixture was diluted with ethyl acetate (150 mL) then washed with 1N HCl (100 mL), water (100 mL), brine (100 mL), dried (MgSO$_4$), filtered and concentrated in vacuo. The crude product was purified by flash chromatography using hexanes: ethyl acetate (3:2). The solid obtained after concentration was further triturated with hexanes:ethyl acetate (4:1) to yield 0.75 g (76%) of 48.

3-(3,5-Dimethylphenyl)-2-{4-[4-(2,4-dioxothiazolidin-5-ylmethyl)-phenoxy]-phenyl}-acrylic acid methyl ester (49). To a solution of 48 (240 mg, 0.4 mmol) in methanol (10 mL) was added sodium methoxide (0.5 N in methanol, 2 mL). After 10 min the mixture was diluted with 1N HCl (2 mL) and the product was extracted into ethyl acetate (50 mL), washed with water (50 mL), brine (50 mL), dried (MgSO$_4$), filtered and concentrated in vacuo. The crude material was purified by flash chromatography using hexanes:ethyl acetate (3:2) to yield 49 (122 mg, 62%) as a white foam. $^1$H NMR (400 MHz, DMSO-d$_6$): δ 12.10 (br s, 1H), 7.71 (s, 1H), 7.28 (d, J=8.8 Hz, 2H), 7.18 (d, J=8.8 Hz, 2H), 7.03 (d, J=8.8 Hz, 2H), 6.97 (d, J=8.8 Hz, 2H), 6.92 (s, 1H), 6.68 (s, 2H), 4.91 (dd, J=8.8 and 4.4 Hz, 1H), 3.73 (s, 3H), 3.37 (dd, J=14.0 and 4.4 Hz, 1H), 3.12 (dd, J=14.0 and 8.8 Hz, 1H), 2.12 (s, 6H).

5-(4-{4-[2-(3,5-Dimethylphenyl)-1-(morpholine-4-carbonyl)-vinyl]-phenoxy}-benzyl)-thiazolidine-2,4-dione (50). To a suspension of 48 (116 mg, 0.2 mmol) in dichloromethane (5 mL) at room temperature was added morpholine (87 µL, 1 mmol). Solution became clear. After 10 min the mixture was treated with 10% citric acid (4 mL). The dichloromethane layer was dried (MgSO$_4$) and directly loaded onto a column which was eluted with hexanes:ethyl acetate (2:3) to yield 50 (104 mg, 86%) as a white foam. $^1$H NMR (400 MHz, DMSO-d$_6$): δ 12.10 (br s, 1H), 7.27 (d, J=8.8 Hz, 2H), 7.26 (d, J=8.8 Hz, 2H), 6.98 (d, J=8.8 Hz, 2H), 6.96 (d, J=8.8 Hz, 2H), 6.85 (s, 1H), 6.72 (s, 2H), 6.61 (s, 1H), 4.91 (dd, J=8.8 and 4.4 Hz, 1H), 3.59 (bs, 8H), 3.37 (dd, J=14.0 and 4.4 Hz, 1H), 3.12 (dd, J=14.0 and 8.8 Hz, 1H), 2.13 (s, 6H).

EXAMPLE 7

Synthesis of 5-(4-{4-[2-(4-methoxyphenyl)-vinyl]-phenoxy}-benzyl)-thiazolidine-2,4-dione (54) (see Scheme 8)

5-(4-Hydroxybenzylidene)-thiazolidine-2,4-dione (51). To a mixture of 4-hydroxybenzaldehyde (3.67 g, 30 mmol), 2,4-thiazolidinedione (3.51 g, 30 mmol) and benzoic acid (4.40 g, 36 mmol) in toluene (100 mL) was added piperidine (4.5 mL, 45 mmol) and the mixture was equipped with a Dean Stark apparatus and brought to a vigorous reflux. After 45 min the mixture was cooled in an ice bath and the supernatant was decanted. The bright yellow solid was made into a suspension by the addition of glacial acetic acid (100 mL) and filtered through a Buchner funnel to yield a pale yellow solid (6.00 g, 90%). $^1$H NMR: (400 MHz, DMSO-d$_6$): δ 12.45 (bs, 1H), 10.30 (s, 1H), 7.70 (s, 1H), 7.45 (d, J=8.8 Hz, 2H), 6.91 (d, J=8.8 Hz, 2H).

5-(4-Hydroxybenzyl)thiazolidine-2,4-dione (52). To a suspension of 51 (6.00 g, 27 mmol) in glacial acetic acid (100 mL) was added ammonium formate (6.27 g, 100 mmol) and 10% Pd on carbon (5.80 g) and the mixture was heated to vigorous reflux for 16 h. The mixture was cooled to room temperature then filtered through Celite. Most of the acetic acid was removed in vacuo then the crude product was dissolved in ethyl acetate (250 mL), washed with water (2×250 mL) then brine (250 mL). The organic layer was dried (MgSO$_4$), filtered and concentrated in vacuo to yield a beige solid (5.35 g, 85%). $^1$H NMR: (400 MHz, DMSO-d$_6$): δ 11.98 (bs, 1H), 9.32 (s, 1H), 7.02 (d, J=8.4 Hz, 2H), 6.68 (d, J=8.4 Hz, 2H), 4.82 (dd, J=8.4 and 4.0 Hz, 1H), 3.25 (dd, J=14.4 and 4.4 Hz, 1H), 2.99 (dd, J=14.0 and 9.2 Hz, 1H).

4-[4-(2,4-Dioxothiazolidin-5-ylmethyl)-phenoxy]-benzaldehyde (53). To a solution of 52 (5.35 g, 24 mmol) in DMF (150 mL) was added 4-fluorobenzaldehyde (3.00 g, 24 mmol) and Cs$_2$CO$_3$ (20 g, 62 mmol) and the mixture was heated to 100° C. for 2 h. The mixture was poured over vigorously stirring 10% citric acid (200 mL) and ethyl acetate (200 mL). The organic layer was washed with water (300 mL), brine (300 mL), dried (MgSO$_4$), filtered and concentrated in vacuo.

The crude product was triturated in hexanes-ethyl acetate (2:1) to yield a white solid (5.15 g, 65%). $^1$H NMR: (400 MHz, DMSO-d$_6$): δ 12.07 (bs, 1H), 9.92 (s, 1H), 7.92 (d, J=8.8 Hz, 2H), 7.35 (d, J=8.4 Hz, 2H), 7.12 (d, J=8.4 Hz, 2H), 7.09 (d, J=8.4 Hz, 2H) 4.94 (dd, J=8.4 and 4.4 Hz, 1H), 3.41 (dd, J=14.4 and 4.4 Hz, 1H), 3.17 (dd, J=14.4 and 9.2 Hz, 1H).

5-(4-{4-[2-(4-Methoxyphenyl)-vinyl]-phenoxy}-benzyl)-thiazolidine-2,4-dione (54). To a suspension of 4-methoxybenzyltriphenylphosphonium chloride (419 mg, 1.0 mmol) in THF (10 mL) at 0° C. was added solid potassium tert-butoxide (224 mg, 2.0 mmol). The resultant orange-red solution was stirred for 15 min at 0° C. then cooled to −45° C. Solid compound 53 (327 mg, 1.0 mmol) was added and the reaction mixture stirred for 30 min at this temperature. To this pale yellow solution glacial acetic acid (60 μL, 1 mmol) was added and the solvent was removed in vacuo. The crude product was suspended in dichloromethane, adsorbed onto silica gel and purified by flash chromatography using hexanes-ethyl acetate (7:3) to yield a white solid (143 mg, 33%) after drying under high vacuum. $^1$H NMR: (400 MHz, DMSO-d$_6$): δ 12.04 (bs, 1H), 7.27 (d, J=8.0 Hz, 2H), 7.24 (d, J=8.4 Hz, 2H), 7.18 (d, J=8.4 Hz, 2H), 6.97 (d, J=8.4 Hz, 2H), 6.88 (d, J=8.8 Hz, 2H), 6.84 (d, J=8.8 Hz, 2H), 6.53 (d, J=12.4 Hz, 2H), 6.48 (d, J=12.0 Hz, 2H), 4.90 (dd, J=9.2 and 4.4 Hz, 1H), 3.36 (dd, J=14.0 and 4.4 Hz, 1H), 3.11 (dd, J=14.0 and 8.8 Hz, 1H).

EXAMPLE 8

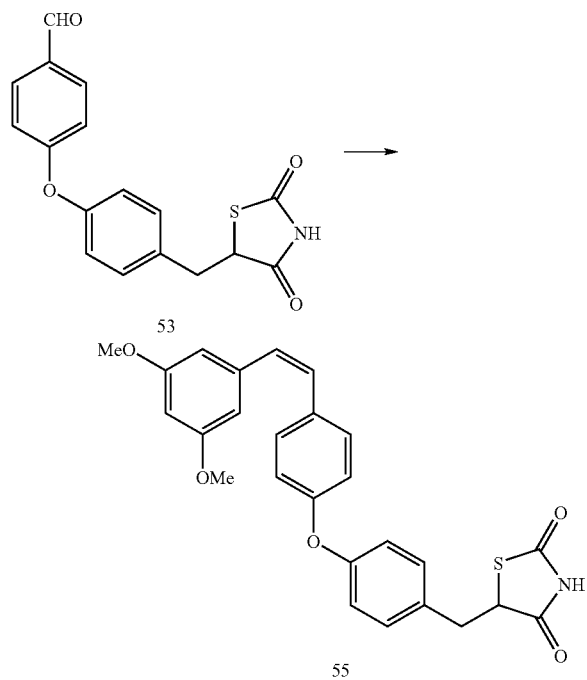

5-(4-{(4-[2-(3,5-Dimethoxyphenyl)vinyl]-phenoxy}-benzyl)-thiazolidine-2,4-dione (55). To a suspension of 3,5-dimethoxybenzyltriphenylphosphonium bromide (0.82 g, 2.0 mmol) in THF (10 mL) at 0° C. was added solid potassium tert-butoxide (224 mg, 2.0 mmol). The resultant red solution was stirred for 15 min at 0° C. then cooled to −78° C. Solid 53 (0.3 mg, 0.90 mmol) was added and the reaction was allowed to warm to room temperature. After 30 min 10% citric acid (50 mL) was added and the mixture was partitioned between water (50 mL) and ethyl acetate (75 mL). The organic layer was washed with water (50 mL) and brine (50 mL) then dried (MgSO$_4$), filtered and concentrated in vacuo. The crude product was purified by flash chromatography using hexanes-ethyl acetate (7:3) to yield 55 as a slightly opaque film (25 mg, 6%) after concentration and drying under high vacuum. $^1$H NMR (400 MHz, DMSO-d$_6$): δ 12.04 (bs, 1H), 7.26 (d, J=8.8 Hz, 2H), 7.25 (d, J=8.8 Hz, 2H), 6.93 (d, J=8.4 Hz, 2H), 6.91 (d, J=8.4 Hz, 2H), 6.61 (d, J=12.4 Hz, 1H), 6.53 (d, J=12.0 Hz, 1H), 6.39 (d, J=2.4 Hz, 1H), 6.36 (t, J=2.4 Hz, 1H), 4.90 (dd, J=9.2 and 4.4 Hz, 1H), 3.62 (s, 6H), 3.36 (dd, J=14.0 and 4.4 Hz, 1H), 3.11 (dd, J=14.4, 8.8 Hz, 1H).

EXAMPLE 9

The syntheses shown in this example are illustrated in Scheme 9.

4'-Methoxybiphenyl-3-ol (56). To a solution of 3-hydroxyphenylboronic acid (1.00 g, 7.3 mmol) in 2M aqueous K$_2$CO$_3$ (4 mL) was added a solution of 4-iodoanisole (1.70 g, 7.3 mmol) in acetone (4 mL). A homogeneous mixture was obtained by sequential addition of water (60 mL) and acetone (30 mL). Catalytic Pd(OAc)$_2$ was added (160 mg, 0.73 mmol) and the mixture was stirred for 10 min at room temperature. The acetone was removed from the dark brown solution in vacuo and the resultant aqueous mixture was acidified with 1N HCl (20 mL) and extracted with ethyl acetate (75 mL). The organic layer was washed with water (50 mL), brine (50 mL), dried (MgSO$_4$), filtered and concentrated in vacuo. The crude product was suspended in dichloromethane and adsorbed onto silica gel and purified by flash chromatography using hexanes-ethyl acetate (3:1) to yield 1.20 g (82%) 56 as a white solid after solvent removal.

4-(4'-Methoxybiphenyl-3-yloxy)-benzaldehyde (57). To a solution of 56 (1.20 g, 6.0 mmol) and 4-fluorobenzaldehyde (745 mg, 6.0 mmol) in DMF (25 mL) was added cesium carbonate (3.90 g, 12.0 mmol). After stirring for 1 h at 100° C., the product was partitioned between ethyl acetate (100 mL) and water (100 mL). The organic layer was washed with water (100 mL), brine (100 mL), dried (MgSO$_4$), filtered and concentrated in vacuo. The crude product was dissolved in dichloromethane and adsorbed onto silica gel and purified by flash chromatography using hexanes-ethyl acetate (6:1) to yield 57 (1.23 g, 67%) as a white solid after solvent removal.

5-[4-(4'-Methoxybiphenyl-3-yloxy)-benzylidene]-thiazolidine-2,4-dione (58). A mixture of 57 (1.23 g, 4.0 mmol), 2,4-thiazolidinedione (0.48 g, 4.0 mmol), benzoic acid (0.60 g, 4.8 mmol) and piperidine (0.61 mL, 6.0 mmol) in toluene (30 mL) was heated to a vigorous reflux until most of the solvent had evaporated. A yellow suspension was achieved by addition of acetic acid (25 mL) followed by sonication. Filtration of the suspension followed by washing with acetic acid (10 mL) yielded 58 (1.25 g, 75%) after filtration and oven drying. $^1$H NMR (400 MHz, DMSO-d$_6$): δ 12.57 (br s, 1H), 7.78 (s, 1H), 7.63 (d, J=8.8 Hz, 2H), 7.62 (d, J=8.8 Hz, 2H), 7.49 (d, J=5.2 Hz, 2H), 7.36 (t, J=1.6 Hz, 1H), 7.16 (d, J=8.8 Hz, 2H), 7.03 (m, 1H), 7.01 (d, J=8.8 Hz, 2H), 3.7 (s, 3H).

5-[4-(4'-Methoxybiphenyl-3-yloxy)-benzyl]-thiazolidine-2,4-dione (59). To a suspension of 58 (1.25 g, 3.0 mmol) in acetic acid (30 mL) was added ammonium formate (1.50 g, 24 mmol) and 10% Pd on carbon (1.30 g). After vigorous refluxing for 16 h, the mixture was filtered through Celite, which was subsequently washed with ethyl acetate (100 mL). The mixture was washed with water (2×75 mL), 1N NaHCO$_3$ (50 mL), brine (75 mL) then dried (MgSO$_4$), filtered and concentrated in vacuo. The crude product was dissolved in dichloromethane, adsorbed onto silica gel and purified by flash chromatography using hexanes:ethyl acetate (3:7) to yield a white solid (0.48 g, 38%) after concentration then trituration and filtration from hexanes-ethyl acetate (4:1). $^1$H NMR (400 MHz, DMSO-$d_6$): δ 12.04 (br s, 1H), 7.58 (d, J=8.8 Hz, 2H), 7.43 (t, J=7.6 Hz, 1H), 7.39 (dt, J=8.0, 1.6 Hz, 1H), 7.27 (d, J=8.8 Hz, 2H), 7.22 (t, J=2.0 Hz, 1H), 7.01 (d, J=8.8 Hz, 2H), 7.00 (d, J=9.2 Hz, 2H), 4.91 (dd, J=8.8 and 4.4 Hz, 1H), 3.79 (s, 3H), 3.37 (dd, J=14.4 and 4.4 Hz, 1H), 3.13 (dd, J=14.4 and 8.8 Hz, 1H).

EXAMPLE 10

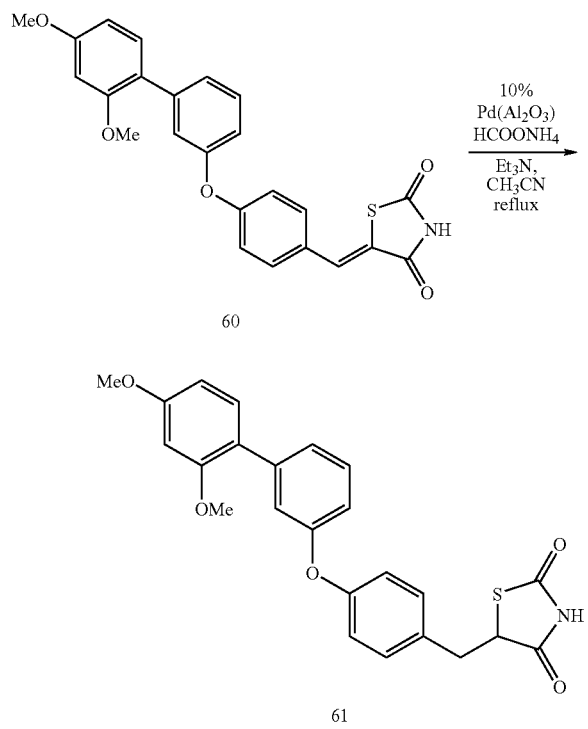

5-[4-(3',5'-Dimethoxybiphenyl-3-yloxy)-benzyl]-thiazolidine-2,4-dione (61). First, 5-[4-(2',4'-dimethoxybiphenyl-3-yloxy)-benzylidene]-thiazolidine-2,4-dione (60), was synthesized using a scheme analogous to the synthesis of 58 depicted in Scheme 9. To a suspension of 60 (0.28 g, 0.65 mmol) in acetonitrile (20 mL) was added triethylamine (180 µL, 1.3 mmol), ammonium formate (0.41 g, 6.5 mmol) and 10% Pd on alumina (0.5 g). After refluxing for 2.5 h, the mixture was filtered through Celite, which was subsequently washed with ethyl acetate (60 mL). The mixture was acidified with 10% citric acid (50 mL) then washed with water (50 mL), brine (50 mL) then dried (MgSO$_4$), filtered and concentrated in vacuo. The crude product was purified by flash chromatography using hexanes:ethyl acetate (3:7) to yield a light film (59 mg, 21%) after concentration and drying under high vacuum. $^1$H NMR (400 MHz, DMSO-$d_6$): δ 12.04 (br s, 1H), 7.38 (t, J=8.4 Hz, 1H), 7.27 (d, J=9.2 Hz, 2H), 7.22 (d, J=8.4, 1H), 7.20 (dt, J=8.4 and 0.8 Hz, 1H), 7.06 (t, J=2.0 Hz, 1H), 7.00 (d, J=8.8 Hz, 2H), 6.90 (ddd, J=8.0 2.4 and 0.8 Hz, 1H), 6.64 (d, J=2.0 Hz, 1H), 6.60 (dd, J=8.4 and 2.4 Hz, 1H), 4.91 (dd, J=8.8 and 4.4 Hz, 1H), 3.79 (s, 6H), 3.37 (dd, J=14.4 and 4.4 Hz, 1H), 3.13 (dd, J=14.4 and 8.8 Hz, 1H).

EXAMPLE 11

Prevention of Cancellous Bone Loss in Adjuvant Induced Arthritic (AIA) Rats

Inflammatory arthritis results in significant peri-articular bone loss due to activation of cytokines that activate osteoclast activity. Thiazolidinediones (TZD) are insulin sensitizing agents that may inhibit TNF-alpha production, an important factor leading to bone loss in inflammatory arthritis The purpose of this investigation was to demonstrate that the TZD compound 11 and etanercept (p55 TNF soluble receptor) could prevent bone loss in AIA rats. Arthritis was induced in male Lewis rats (Harlan, weight 150 g) by immunizing them with Freund's Complete Adjuvant containing *Mycobacterium butyricum* (100 µg) on the tail base. When the arthritic symptoms began to appear (by day 12-14), the animals were randomized to one of three treatment groups: Group I: vehicle (20% PEG-400 in water, per oral gavage). Group II: compound 11 (50 mg/kg, per oral gavage once daily) Group III: etanercept (1.67 mg/kg, intra-peritoneal once daily). Each limb was individually scored from 0 (no change or normal) to 4 (marked arthritis with swelling, erythema, nodules, deformation, rigidity) by an observer blinded to the treatment groups. The body weights, number of limbs affected and hind paw volume were also noted. On day 11 AIA rats were sacrificed and the right femur and tibia harvested, dissected and fixed in 70% EtOH. Cancellous bone volume and microstructure of the right proximal tibia and distal femur were accessed by MicroCT (µCT-20, Scanco Medical, Bassersdorf, Switzerland). Results of right proximal tibia are shown in the following table.

TABLE 2

| Groups | BV/TV (%) | Tb.N (1/mm) | Conn.Dens (1/mm3) | C.Th (µm) | SMI (0-3) |
|---|---|---|---|---|---|
| Sham (n = 7) | 21.4 ± 2.6 | 4.5 ± 0.4 | 70.5 ± 14.9 | 250 ± 24 | 2.3 ± 0.9 |
| Vehicle (n = 12) | 6.2 ± 4.0 | 2.0 ± 0.4 | 10.3 ± 15.3 | 167 ± 27 | 3.5 ± 0.3 |
| Comp. 11 (n = 9) | 13.7 ± 4.7 | 2.6 ± 0.5 | 38.3 ± 19.7 | 186 ± 25 | 2.8 ± 0.3 |
| Etanercept (n = 9) | 12.9 ± 5.2 | 2.8 ± 0.5 | 31.9 ± 19.7 | 198 ± 25 | 2.8 ± 0.4 |

In summary, significant cancellous bone loss and microarchitecture changes occurred in AIA rats. However, in this AIA model, nearly 50% less cancellous bone was lost in animals treated with either compound 11 or etanercept. Therefore, compound 11 may be effective in reducing bone loss in inflammatory arthritis and similar rapid bone loss states.

EXAMPLE 12

Glucose Uptake

Basal glucose uptake was measured in differentiated 3T3-L1 adipocytes following the protocol of Tafuri (6) with modifications. Briefly, 3T3-L1 fibroblasts, obtained from ATCC (Manassas, Va.), were differentiated to adipocytes by treating cells with porcine insulin (1 µg/ml for 4 days), dexamethasone (0.25 µM for first 2 days) and isobutyl methyl xanthine (IBMX, 0.5 mM for first 2 days) (all from Sigma Chemicals, St Louis, Mo.) following the protocol of Frost and Lane (7). Differentiated adipocytes were incubated in Dulbecco's Modified Eagle Medium (DMEM) containing 10% fetal bovine serum (GibcoBRL, Gaithersburg, Md.) with various concentrations of Compound 11 or vehicle (0.1% DMSO) for 48 h in 24-well plates, in triplicate. Cells were washed with phosphate buffered saline (PBS, 150 mM NaCl, 11 mM $KH_2PO_4$, 3 mM $Na_2HPO_4$; pH 7.4) and incubated in glucose-free DMEM for 2 h at 37° C. The cells were washed 3 times with Krebs Ringer Phosphate Buffer (KRP). Glucose uptake was initiated by addition of 0.25 µCi 2-$^{14}$C(U)-deoxy-D-glucose (300 µCi/mmol, American Radiolabeled Chemicals Inc., St Louis, Mo.) per well and the cells incubated for 10 min at room temperature in the presence of 0.1 mmol cold 2-deoxy-D-glucose. Finally, the cells were washed three times with ice-cold PBS containing 10 mM cold glucose, lysed with 0.5% SDS, and counted in a scintillation counter (Beckman LS6500).

Transfection and Luciferase Activity Assay

Human PPAR-γ2 expression vector was constructed by inserting PPAR-γ2 encoding region into pcDNA3.1+ vector (Invitrogen, Carlsbad, Calif.). Luciferase reporter vector was constructed by ligating PPRE response element adjacent to the upstream of Firefly luciferase coding region. Control vector, pRL-SV40 expressing Renilla luciferase was purchased from Promega (Madison, Wis.).

About 2.7×10$^4$ 293 cells (ATCC, Manassas, Va.) were plated into a 35 mm culture well and maintained in Eagle's Minimal Essential Medium (ATCC, Manassas, Va.) supplemented with 10% heat inactivated horse serum (ATCC, Manassas, Va.) for 24 hours. Expression, reporter and control vectors (2.5 ng control and 100 ng others per culture well) were transfected by LIPOFECTAMIN PLUS™ Reagent (Invitrogen, Carlsbad, Calif.). Transfection reagent and DNA were prepared according to manufacture's recommendations and incubated with cells for 3 hours followed by adding equal volume EMEM supplemented with 20% horse serum. Twenty-four hours after transfection, cells were treated with vehicle or compounds at indicated final concentration for 24 hours. Final concentration of vehicle was 0.001% DMSO (Sigma, ST Louis, Mo.) in medium. Vehicle and compound treatment were all conducted in triplicate. Each culture well was then assayed for a response characterized by increased Firefly luciferase activity normalized with Renilla luciferase activity.

Assays for Firefly luciferase activity and Renilla luciferase activity followed the standard protocol of Dual-luciferase Reporter® Assay System (Promega, Madison, Wis.). Briefly, 400 µl Passive Lysis Buffer was added into each culture well and all wells were placed on a shaker for 15 minutes. Five µl cell lysate of each well was added to a reaction tube. Luciferase reagent II and Stop & Glo® were injected into the reaction tube sequentially by Sirius Luminometer (Berthold Detection Systems, Pforzheim, Germany). Final reporter activity was calculated as the ratio of Firefly luciferase activity over by Renilla luciferase activity.

Results

The three possible methyl ester analogs with double bond(s) at different positions (10, 11, 17), the methyl ester without any double bond 18, the free acid analog 14 of compound II, and the Z-isomer 23 of 11 were made and tested on in vitro glucose uptake in 3T3-L1 cells (Tafuri et al, Endocrinology, 137:4706-12, 1996; Frost and Lane, J Biol Chem 260:2646-52, 1985) at 0.1 and 1 1M concentrations (Table 3). At a concentration of 1 µM compounds 10, 11, and 14 increased glucose uptake to a level comparable to rosiglitazone. Compounds 17 and 18 showed modest activity at 1 µM concentration and compound 23 was essentially inactive. At a concentration of 0.1 µM, compounds 10 and 11 retained activity, but less than that of rosiglitazone. Compound 10, containing two double bonds, showed lower increased glucose uptake compared to 11. Compound 17 with only one double bond joined to the TZD ring and the doubly reduced product 18 were devoid of activity at 0.1 µM. We infer from this that the absence of the double bond joined to the TZD ring and the presence of the cinnamic acid double bond is important for increased glucose uptake in this system. The lack of activity of 23, the corresponding Z-isomer of 11, indicates that the geometry of the double bond is critical to activity. The lower activity of the free acid 14 compared to the methyl ester 11 may be due to difference in lipophilicity of the compounds.

Antidiabetic compounds of the TZD class increase peripheral tissue sensitivity to insulin via PPAR-gamma activation. It was our goal to introduce into diphenylethylene compounds, by chemical modification, this additional mechanism of action. Agonist activity on PPAR-gamma was explored in an in vitro system using cells transfected with human PPAR-gamma2 ligated to firefly luciferase as the reporter element. The results from this in vitro transactivation assay for the tested compounds are summarized in Table 4. The most potent compound in this series was found to be 11 ($EC_{50}$ of 0.28 µM) which had approximately one-thirtieth the activity of rosiglitazone ($EC_{50}$ of 0.009 µM) in the same assay. Compound 10 (two double bonds) and compound 14 (the free acid of 11) also showed reasonable potency although less than that of compound 11. Compounds 17 and 18, in which the cinnamic acid double bond was reduced, were essentially inactive.

The Z-isomer 23 showed less than one-tenth the potency of compound 11 in this assay. Based on these in vitro results, compound 11 was evaluated in two widely-used mouse models of NIDDM.

Figure 16A:
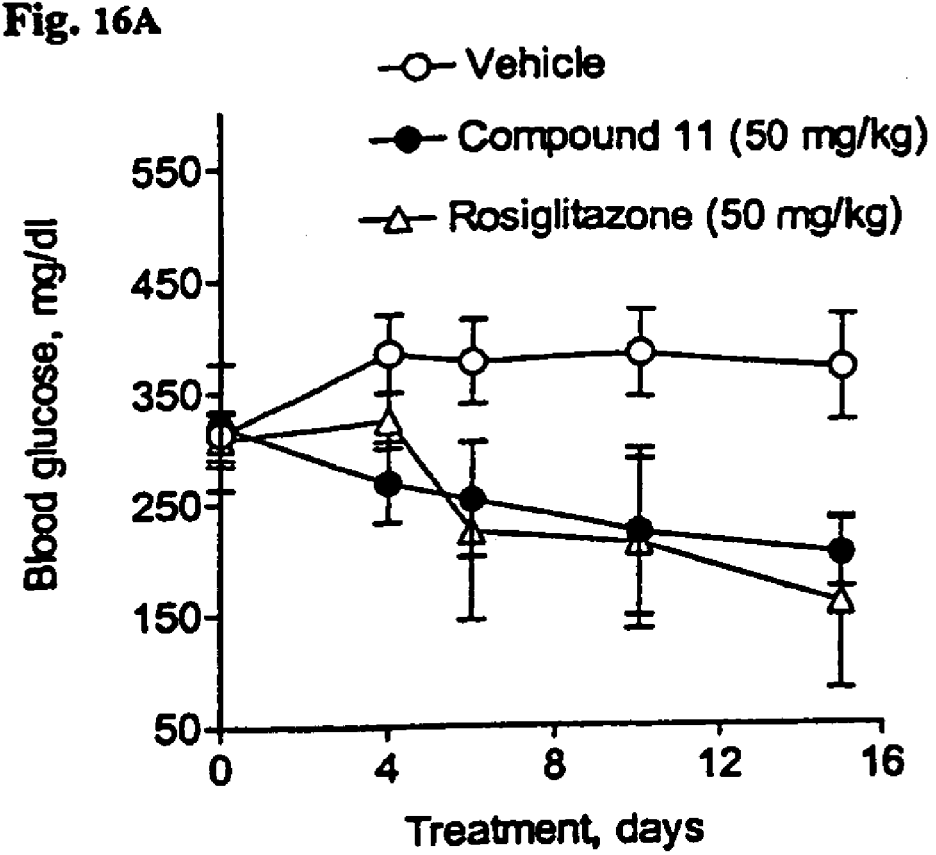
FIG. 16A. Comparison of percent reduction in blood glucose in db/db mice using compound 11 and rosiglitazone. 16B. Body weights of the animals.
Figure 16B:
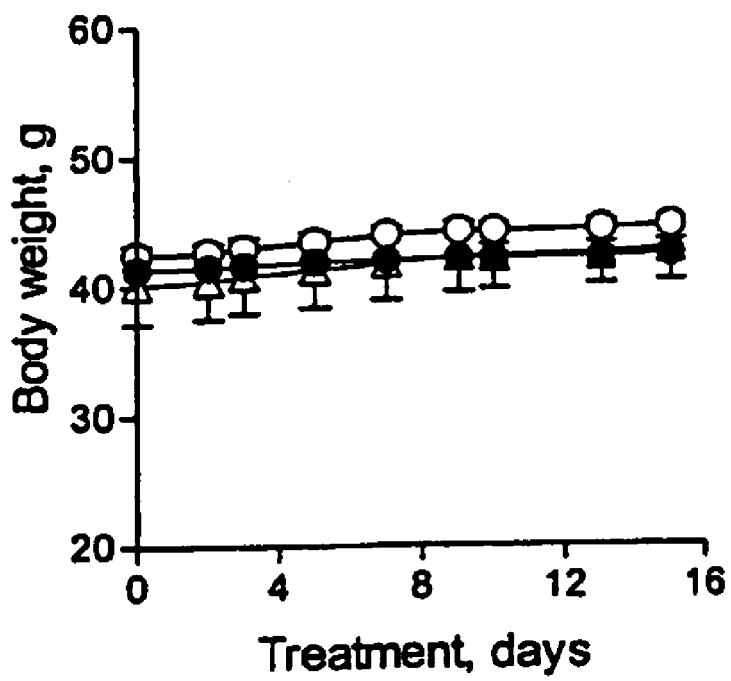

Initially, in vivo glucose-lowering efficacy of 11 was explored in the genetically hyperinsulinemic, diabetic mouse (db/db) model (8 weeks old male mice, 5 animals per group) following a single oral dose of 50 mg/kg (in 0.5% CMC and 10% PEG). Blood glucose levels were monitored at time intervals of 0 min, 1, 4, 6, 24, 48 and 72 h. Compound 11 showed a time dependent glucose lowering effect which was maximal at 24 hrs (23% of 0 min, data not shown). Side by side comparison of rosiglitazone and compound 11 (each at 50 mg/kg/day, orally, for 14 days) showed dramatic, comparable blood glucose lowering effects which increased with duration of dosing (FIG. 16A). Body weights (FIG. 16B) were not affected by either compound in this short term experiment.

Figure 17A:
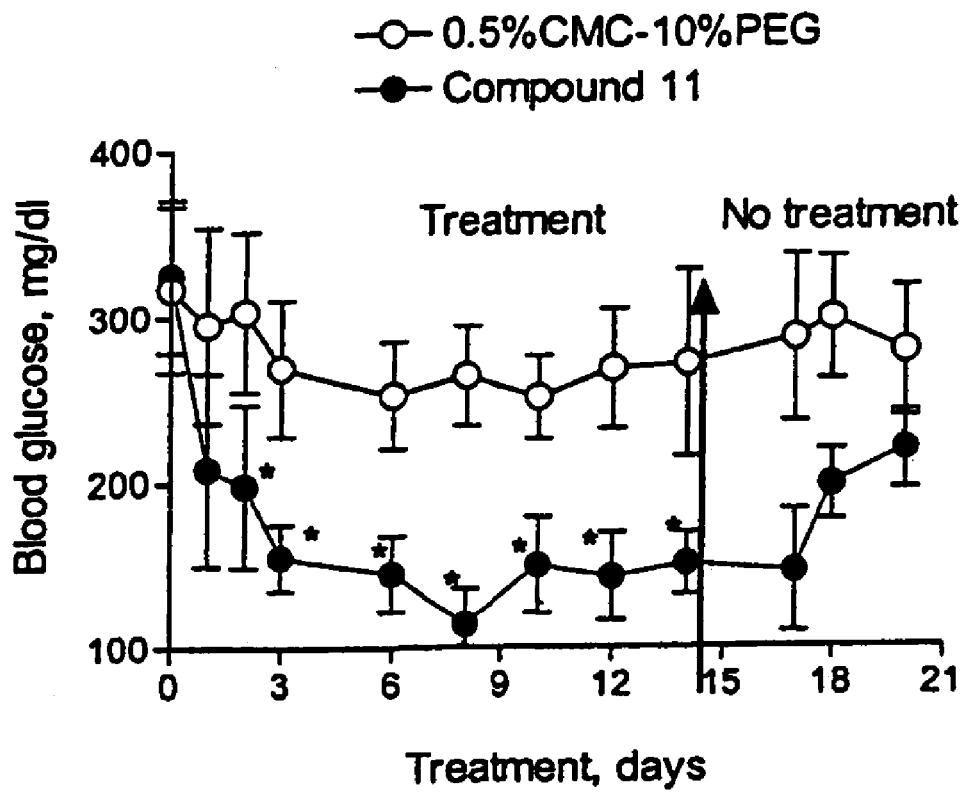
FIG. 17A. Percent reduction in blood glucose in ob/ob mice using compound 11. 17B. Body weights of the animals.
Figure 17B:
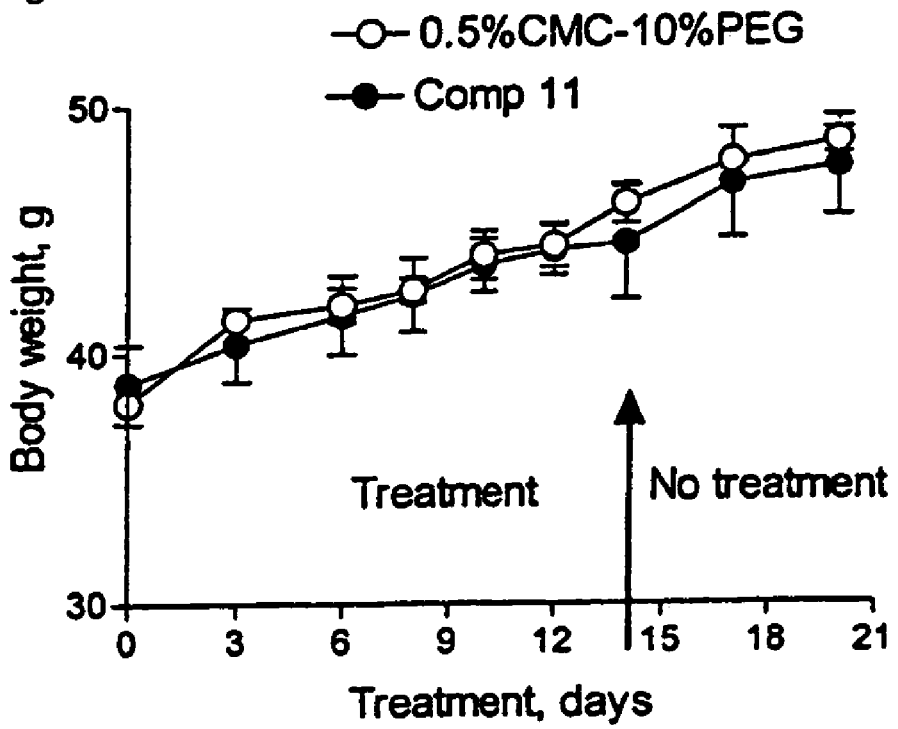

Compound 11 was also evaluated in the genetically obese (ob/ob) male diabetic mouse (7 weeks old male mice, 5 animals per group) with treatment continued for 14 days at a dose of 50 mg/kg body weight. In 11 treated mice blood glucose levels were significantly decreased within 48 hours and normalized by three days (*p value <0.05; paired T test) (FIG. 17A). Blood glucose levels in these mice rebounded slowly after stopping treatment (FIG. 17A). Interestingly, we did not see any increase in body weight of drug treated animals compared to vehicle treated group (FIG. 17B). This may be an advantageous situation compared to strong PPAR-gamma agonists which showed a large body weight gain in different animal models.

Figure 18:
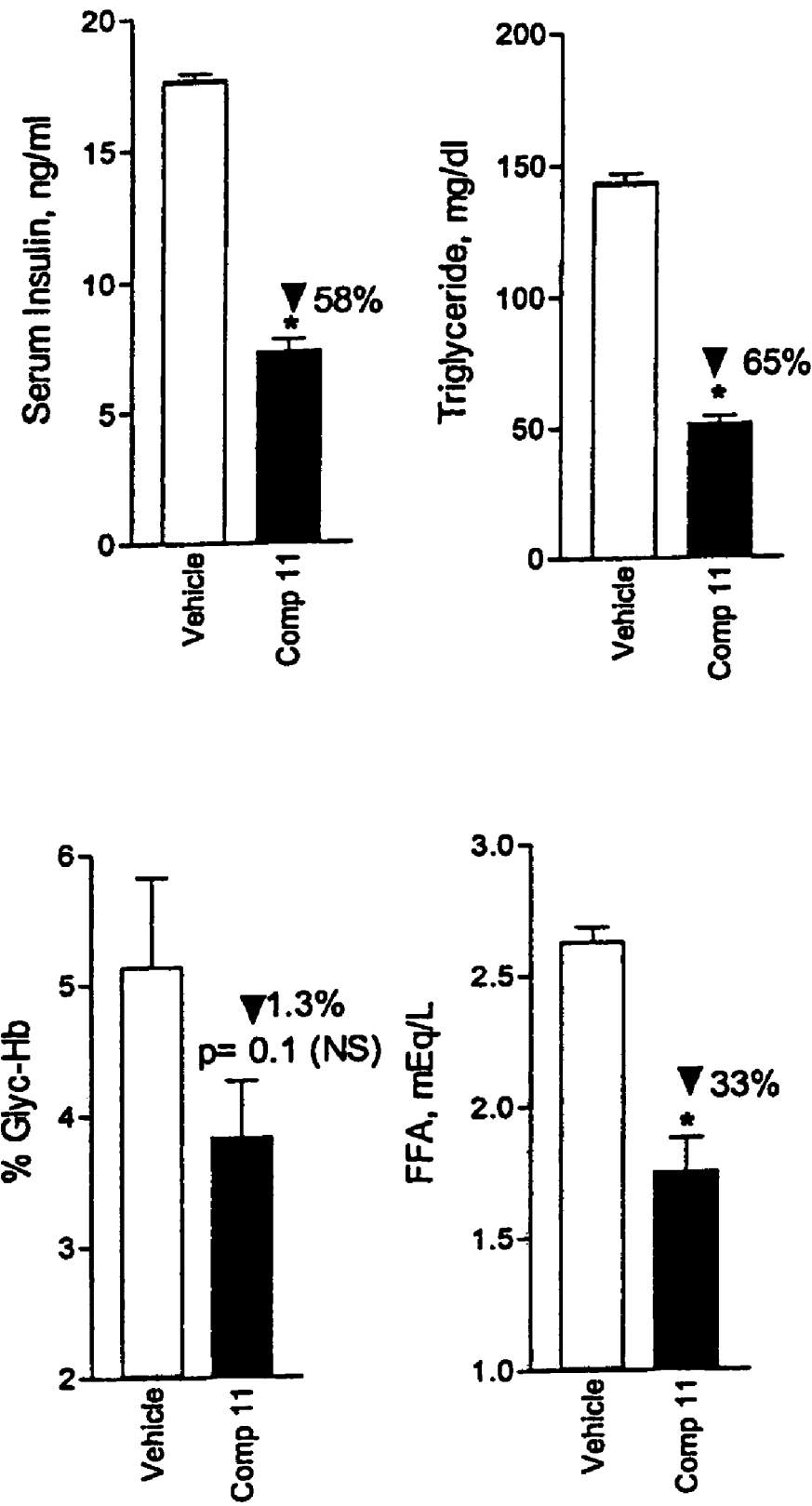
FIG. 18. Serum profile in db/db mice after treatment of 14 days of treatment.

After a treatment of fourteen days blood samples were collected from both the groups for the determination of glycosylated hemoglobin, serum insulin, triglycerides, FFA levels (FIG. 18). Glycosylated hemoglobin, which is being used as marker of diabetes management, was reduced from 5.2% to 3.8% (p=0.15). 11 reduced serum insulin by 58%, triglycerides by 65% and free fatty acid (FFA) levels by 33%, all p<0.05 compared to vehicle treated animals.

Figure 19:
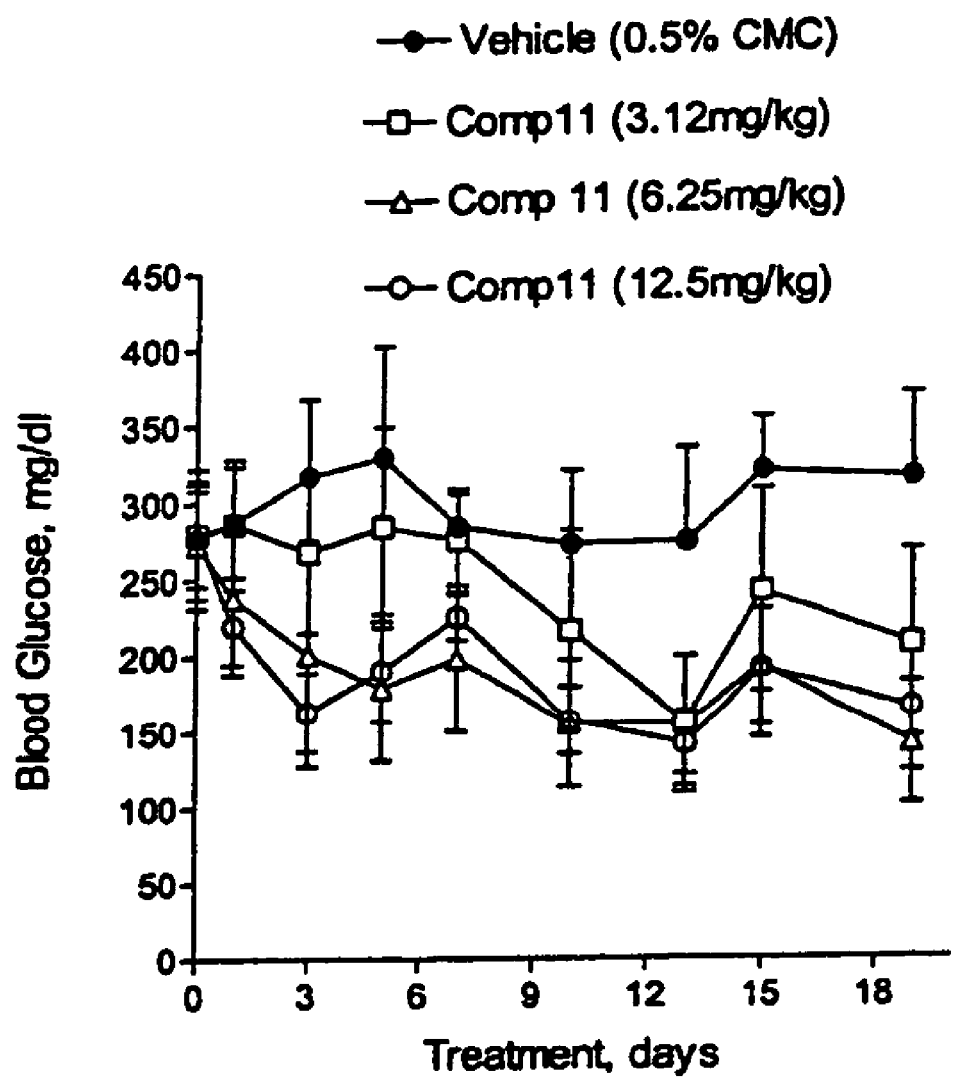
FIG. 19. Dose response of compound 11 on glucose levels in ob/ob mice.

To establish the effective dose of 11, a further experiment was carried out in ob/ob mice (n=8) with three different doses. As shown in FIG. 19 there was a dose dependent glucose lowering effect. Animals treated with a dose of 3.12 mg/kg showed a similar extent of glucose reduction compared to 12.5 mg/kg after twelve days of treatment. Thus, the effect of 11 is comparable with rosiglitazone in both db/db and ob/ob mice.

It has been proposed earlier that the compounds which show high degree of activation of PPAR-gamma generally have superior glucose lowering activities in animal experiments (Wilson et al, J Med Chem 39:665-8, 1996; Foreman et al, Cell 83:803-12, 1995). However, findings reported here differ from this interpretation. We have found a less potent PPAR-gamma agonist 11 which showed a glucose lowering activity in animals comparable to that of rosiglitazone. Attempts are being made to elucidate further the mechanism behind this potent glucose lowering activity of 11. Glycogen synthesis in the liver, but particularly in the muscle is major site for the disposal of postprandial glucose. One possible explanation for strong glucose lowering activity in spite of modest PPAR-gamma agonist activity is our recent observation of higher glycogen synthesis induced by 11 compared to rosiglitazone (see below).

TABLE 3

In vitro Glucose Uptake in 3T3-L1 Adipocytes[a]

| Compound no. | % Glucose uptake | |
|---|---|---|
| | 0.1 μm | 1.0 μm |
| 1 (rosiglitazone) | 204.2 ± 8.5 | 214.7 ± 36.5 |
| 10 | 142.6 ± 7.4 | 209.3 ± 22.6 |
| 11 | 161.6 ± 11.4 | 218.1 ± 10.0 |
| 14 | 108.6 ± 19.9 | 199.5 ± 11.6 |
| 17 | 101.9 ± 6.8 | 130.0 ± 27.0 |
| 18 | 104.4 ± 5.7 | 137.0 ± 10.1 |
| 23 | 89.5 ± 5.6 | 118.0 ± 3.6 |
| Insulin | 335.2 ± 21.7 | 345.6 ± 8.3 |

[a]Basal glucose uptake is expressed as % basal of the non treated cells (each point is the average of quadruplicate determinations ± SD values).

TABLE 4

Induction of PPAR-γ Mediated Luciferase Activity by Thiazolidinediones[a]

| Compound no. | $EC_{50}$ (μM) |
|---|---|
| 1 (rosiglitazone) | 0.009 ± 0.007 |
| 10 | 1.136 |
| 11 | 0.284 ± 0.036 (n = 5)[b] |
| 14 | 0.690 ± 0.038 (n = 2) |
| 17 | 23.9 |
| 18 | 57.7 |
| 23 | 3.686 ± 1.454 (n = 2) |

[a]Results are based on several independent experiments. Each experiment contains at least 8 different concentration of drug treatment (between 0.1 to 30 μM), with each concentration in triplicate. $EC_{50}$ values were calculated by non-linear regression analysis using GraphPad Prism software.
[b]n = independent experiments.

Conclusion

TZD's based on the alpha-phenyl cinnamic acid motif have glucose lowering activity in genetic models of diabetic mice. Compound 11 showed strong glucose lowering activity even though it is a weak PPAR-gamma agonist. Strong glucose lowering activity of 11 in spite of being a weaker PPAR-gamma agonist may be due to its higher glycogen synthesis compared to rosiglitazone. Further investigation is required to fully elucidate the mechanism(s) of action of this new family of TZDs.

EXAMPLE 13

Glycogen Synthesis

Glycogen synthesis was measured as net conversion of $^{14}C$-D-glucose to cellular glycogen in HepG2 cells as described by Ciaraldi et al, Diabetes 41:975-81, 1992. Briefly, HepG2 cells (ATCC, Manassas, Va.) in 6-well plates were treated with Compound 11 or other compounds for 48 h. They were washed with 10 mM HEPES buffer (150 mM NaCl, 5 mM KCl, 1.2 mM $MgSO_4$, 1.2 mM $CaCl_2$, 2.5 mM $CaCl_2$, 10 mM HEPES; pH 7.4) containing 1% BSA. Cells were incubated in the same buffer for 30 min prior to addition of 0.2 μCi/well of $^{14}C$-D-glucose (5 mM final concentration, 10 μCi/mmol, American Radiolabeled Chemicals Inc., St Louis, Mo.). After incubation for 2 h at 37° C. the cells were washed with ice-cold PBS and solubilized with 1 M KOH at 55° C. Converted glycogen was precipitated by ethanol after addition of 10 mM carrier glycogen. The pellet was washed and resuspended in water, and an aliquot was counted in a scintillation counter (Beckman LS6500). Total protein was assayed and results were reported as cpm/mg of protein.

Adipogenesis

Adipogenesis in 3T3-L1 fibroblasts was carried out as described by Wu et al, J Clin Invest 101:22-32, 1998. After two days of growth in 6-well plates, cells were treated either with vehicle (0.1% DMSO) or with compounds for ten days. Fresh medium with compounds or vehicle was replenished every 48 h. Cells were washed with PBS twice and fixed in 10% formalin (Sigma) in PBS. After washing in PBS, cells were stained with freshly diluted Oil Red O in isopropanol for 1 h at room temperature. The cells were washed five times with PBS and visualized under an Olympus BH2 microscope. Quantitative accumulation of triglyceride was also measured under similar experimental conditions, except in this case cells were plated in 100-mm tissue culture dishes. Triglyceride was extracted with methanol:chloroform (2:1) mixture. To monitor the efficiency of recovery, $^{3}H$-cholesterol oleate (50,000 cpm/well, American Radiolabeled Chemicals Inc., St Louis, Mo.) was added in each tube as tracer before extraction following the protocol of Brown et al, J Clin Invest 55:783-93, 1975. Extracted triglyceride was measured by a colorimetric assay (GPO-Trinder, Sigma) according to manufacturer instructions.

Transfection and Transactivation Assays

Human PPARγ2 expression vector was constructed by inserting the PPARγ2 cDNA coding region into pcDNA3.1+ vector (Invitrogen, Carlsbad, Calif.). The PPRE-luciferase reporter gene was the kind gift of Dr. Kenneth Feingold. The control vector, pRL-SV40 containing the Renilla luciferase cDNA was purchased from Promega (Madison, Wis.). About $2.7\times10^4$ HEK293 human embryonal kidney cells (ATCC) were plated into a 35-mm tissue culture dish and maintained in Eagle Modified Essential Medium (EMEM, ATCC) containing 10% heat-inactivated horse serum for 24 h. Expression, reporter (100 ng/dish) and control (2.5 ng/dish) vectors were transfected using LIPOFECTAMIN PLUS™ Reagent (GibcoBRL) according to manufacturer's recommendation. At 24 h after transfection, cells were treated with vehicle (0.001% DMSO in medium) or compounds at the indicated concentration and incubated for 24 h. Each treatment was conducted in triplicate. Each culture dish was assayed for firefly luciferase activity normalized by Renilla luciferase activity to account for differences in transfection efficiency. Luciferase activity was measured using the Dual-luciferase Reporter® Assay System (Promega) and a Sirius luminometer (Berthold Detection System, Pforzheim, Germany).

In Vivo Studies

All procedures performed were in compliance with the Animal Welfare Act and U.S. Department of Agriculture regulations and were approved by the Calyx Therapeutics Institutional Animal Care and Use Committee. Animals were housed at 22° C. and 50% relative humidity, with a 12-h light and dark cycle, and received a regular rodent diet (Harlan Teklad, Madison, Wis.) ad libitum with free access to water. Male C57BL/KsJ-db/db and C57BL/6J-ob/ob mice were obtained from Jackson Laboratories (Bar Harbor, Me.) when their age was 5 weeks. Seven-week-old animals were dosed with Compound 11, rosiglitazone maleate (recrystallized from commercially available tablets) or vehicle (0.5% carboxymethyl cellulose (Sigma, St. Louis, Mo.) in water) orally once daily by gavage. Blood glucose measurements were made with a One Touch Glucose Meter (Life Scan, Inc., Milpitas, Calif.) and/or a glucose oxidase assay (Glucose Trinder, Sigma, St. Louis, Mo.) prior to administering the next dose and in the fed state. Body weights were monitored throughout the study. Eight-week-old male Zucker diabetic fatty (ZDF-fa/fa) rats (Genetic Models, Indianapolis, Ind.) were kept on 6.5% fat Formulab Diet 5008 (PMI Feeds, Richmond, Ind.) for two weeks prior to dosing as described above.

Statistical Analysis

Data are presented as the mean ±standard error (SE) and statistical comparisons were made by t test or ANOVA with Tukey/Kramer post hoc testing where appropriate using StatView 5 software (SAS Institute).

Results

Compound 11 Stimulates Glucose Uptake In Vitro

Figure 20A:
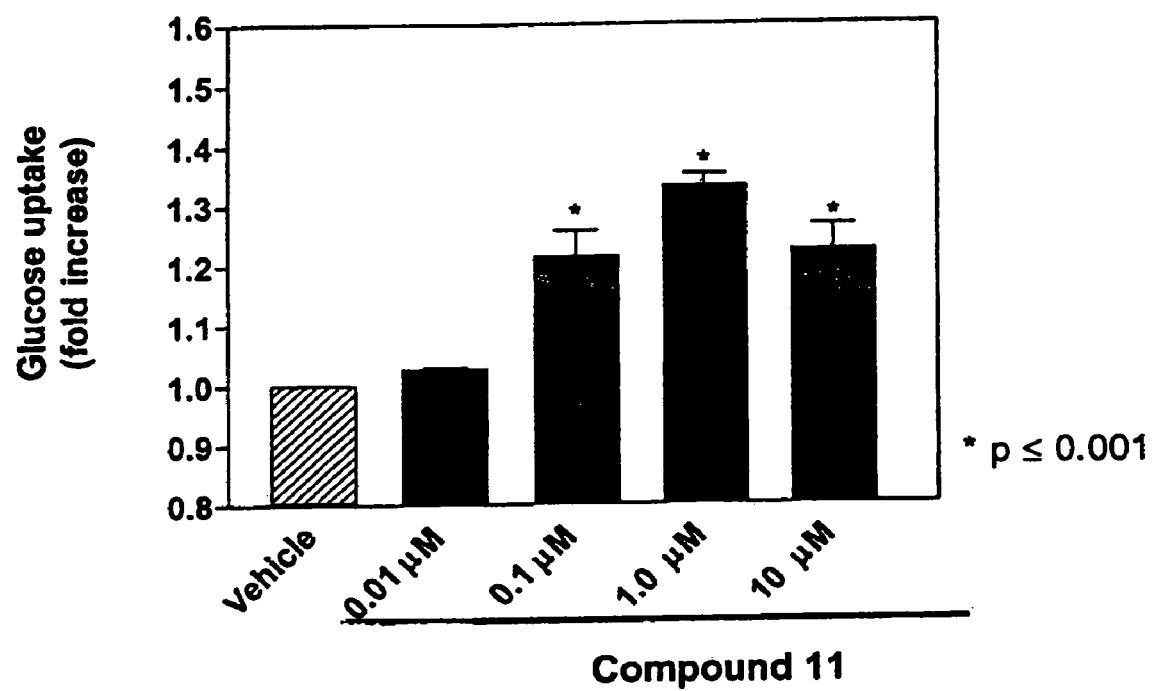
FIG. 20. A. In vitro glucose uptake measured in differentiated 3T3-L1 adipocytes after treatment with increasing concentrations of Compound 11 or vehicle. B. Glucose uptake in differentiated 3T3-L1 adipocytes measured in the presence of increasing concentrations of insulin in the presence of vehicle, rosiglitazone or Compound 11.
Figure 20B:
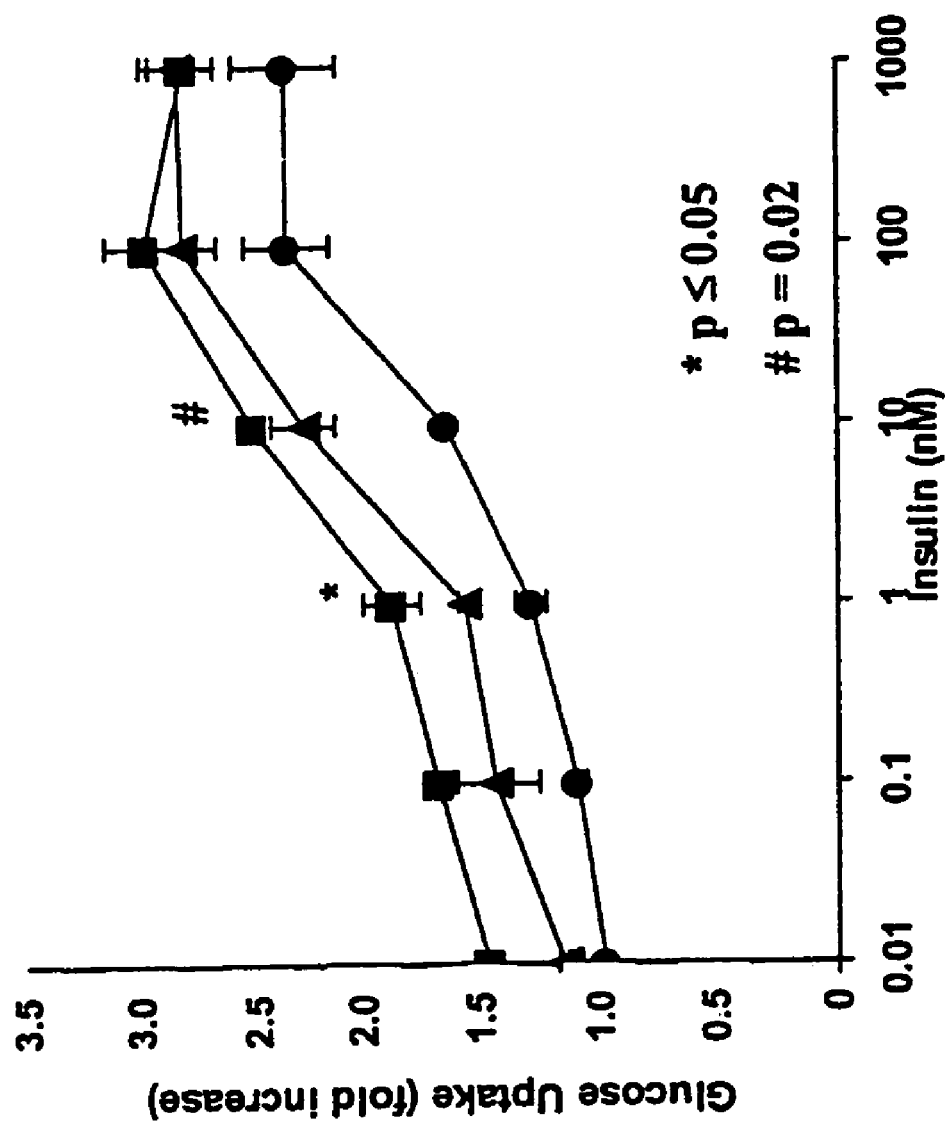

Differentiating 3T3-L1 adipocytes represent an insulin-sensitive cell-culture model for studying glucose uptake and is often used to characterize potential antidiabetic compounds. Although TZDs increase glucose uptake in these cells, both in the absence and presence of insulin, the majority of this effect appears to be the result of non-insulin-mediated glucose disposal. As shown in FIG. 20A, glucose uptake was increased to a maximum of 1.33±0.02 (mean ±SE) fold over basal levels in response to increasing concentrations of Compound 11 (0.01, 0.1, 1.0 and 10 µM). We also examined the effect of Compound 11 and rosiglitazone on insulin-stimulated glucose uptake in 3T3-L1 adipocytes (FIG. 20B).

There was no difference in dose response curves of glucose uptake in response to insulin in the presence (5 µM) or absence of the TZDs. Differences in the maximal responses can be accounted for by the increased amount of basal glucose uptake in the absence of insulin and either Compound 11 or rosiglitazone, indicating an additive, not synergistic, effect on glucose uptake. These results suggest this enhancement of glucose uptake is mediated through a non-insulin-dependent mechanism, such as an increase in GLUT-1 transporters.

In Vivo Antihyperglycemic Effect of Compound 11

Figure 21:
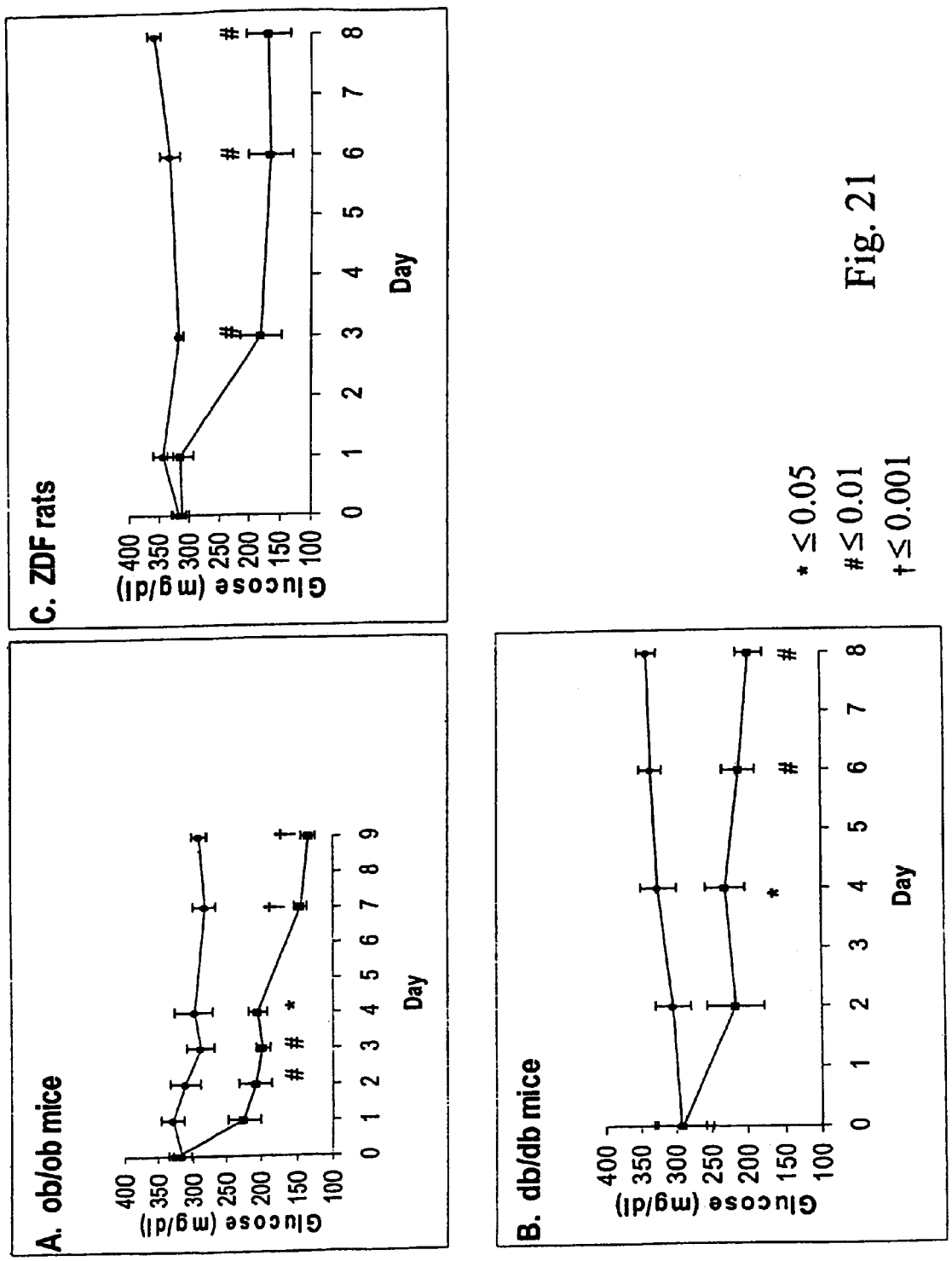
FIG. 21. In Vivo Antihyperglycemic Activity of Compound 11 in Diabetic Animals.

The antihyperglycemic activity of Compound 11 was examined in several models of type 2 diabetes mellitus. FIG. 21 summarizes the effect of Compound 11 given as single daily oral doses of 50 mg/kg (96.2 µmol/kg) over 8 to 9 days. At the end of each study the drug led to marked decreases in blood glucose levels in ob/ob mice (59% vs. baseline), db/db mice (32. % vs. baseline) and ZDF rats (50% vs baseline).

Figure 22:
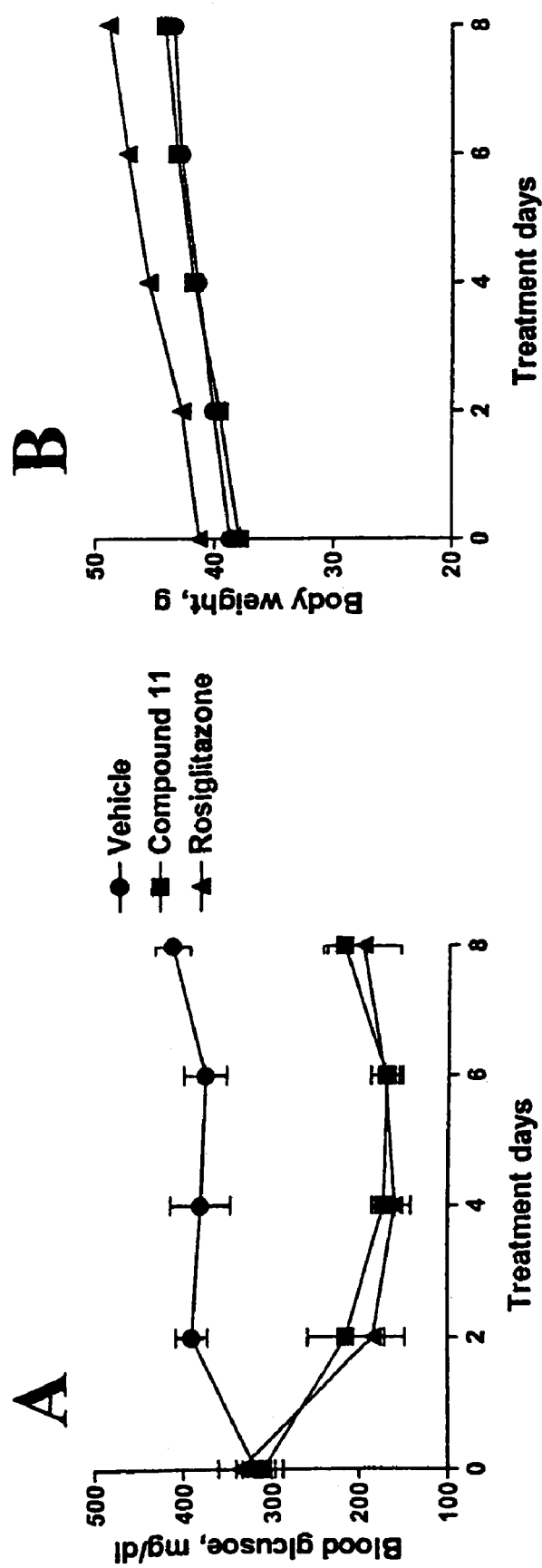
FIG. 22. In Vivo Antihyperglycemic Activity of Compound 11 vs. Rosiglitazone in ob/ob mice.

Weight gain in treated and control animals was similar except for ZDF rats, where Compound 11 treated animals gained 13% more weight than control animals. In a subsequent study, the in vivo potency of Compound 11 was compared to rosiglitazone in ob/ob mice (FIG. 22). Compound 11 and rosiglitazone treatment (both at 10 mg/kg/day; 19.2 and 28.0 µmol/kg/day for Compound 11 and rosiglitazone, respectively) demonstrated similar antidiabetic potency over the 8-day treatment period.

Weight gain was similar in vehicle and drug-treated groups. Both compounds significantly lower serum insulin, free fatty acids and triglycerides in this model (data not shown).

Compound 11 is less Adipogenic than Rosiglitazone.

Because TZDs are ligands for PPAR-gamma and induce adipocyte differentiation (13-15), we sought to determine the adipogenic potential of Compound 11 using the 3T3-L1 preadipocyte model. In these studies, 3T3-L1 fibroblasts were incubated with various concentrations (0.1, 1, 10 µM) of Compound 11, rosiglitazone or vehicle in the absence of dexamethasone, insulin and IBMX. After 14 days cells were stained with Oil Red O, counterstained with methylene blue for visual assessment (FIG. 23B) and assayed for triglyceride accumulation. As shown in FIG. 23A there was a dose-dependent increase in triglyceride accumulation in response to Compound 11 and rosiglitazone. The dose response of triglyceride accumulation in response to Compound 11 is right-shifted in comparison to rosiglitazone. Moreover, the maximal amount of triglyceride accumulated in response to Compound 11 was significantly less than that seen in response to rosiglitazone (3.96 vs. 9.22 fold increase over control, respectively; P<0.0001, ANOVA). Compound 11 at concentrations of 100 µM and higher were cytotoxic in this system (data not shown).

Compound 11 is a Partial Agonist of PPAR☐

Figure 24:
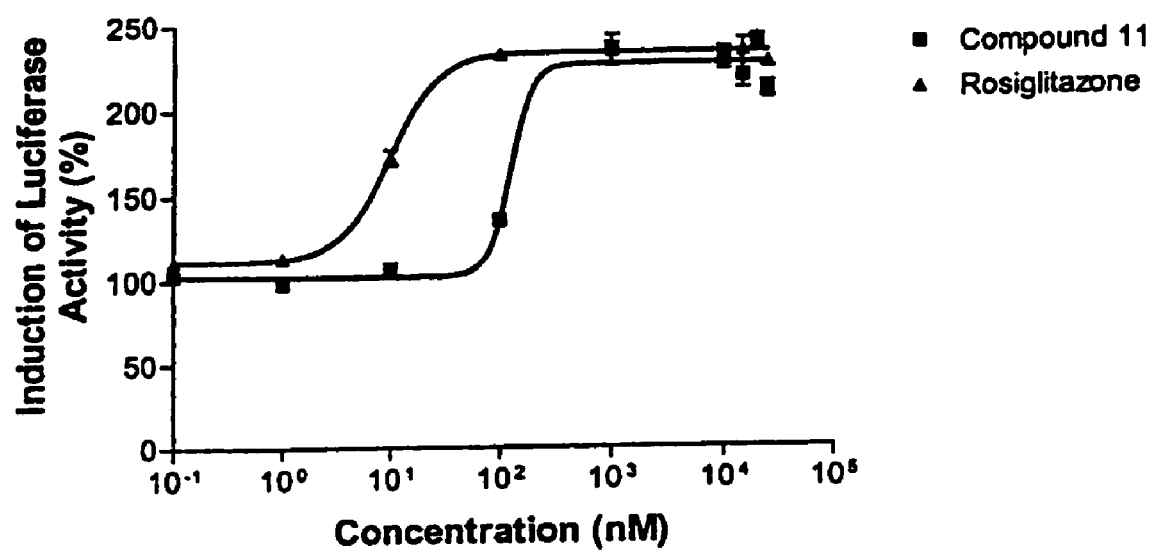
FIG. 24. Induction of PPARgamma-Mediated Transactivation of PPRE-Luc Reporter by Compound 11 and Rosiglitazone.

We examined the ability of rosiglitazone and Compound 11 to transactivate a PPRE-Luc reporter gene in HEK293 cells cotransfected with a human PPAR-gamma2 expression vector. Compound 11 was a substantially less potent activator of PPAR-gamma than rosiglitazone (FIG. 24). The $EC_{50}$ for transactivation in this system was 0.009±0.0007 µM (SE) for rosiglitazone, and 0.284±0.036 µM for Compound 11 (n=5). Similar dose-response curves were obtained using a reporter-gene assay in cells transfected with heterologous cDNA constructs of GAL4-DNA binding domain/PPAR-gamma ligand binding domain and 5× upstream activator sequence (UAS)-luciferase constructs (data not shown).

Compound 11 Increases Glycogen Synthesis in HepG2 Hepatocytes

The ability of Compound 11 to increase glycogen synthesis was examined in HepG2 hepatocytes. FIG. 25A shows that there is a dose-dependent increase in $^{14}C$-glucose incorporated into glycogen in response to Compound 11 in the absence of insulin; this response was maximal (3.1-fold increase over baseline) at 48 to 72 h (FIG. 25B). In contrast, rosiglitazone did not increase glycogen synthesis (0.9-fold decrease at 10 µM, FIG. 25A).

In separate experiments, concentrations of rosiglitazone higher than 30 µM produced only minimal increases in glycogen synthesis (1.4±0.06, SD fold increase over baseline, data not shown). The increase in glycogen synthesis induced by Compound 11 was dependent upon new protein synthesis as it was blocked by cotreatment with cycloheximide (FIG. 25C).

Discussion

Our results indicate that Compound 11 is effective in lowering blood glucose in several animal models of type 2 diabetes. It has a robust antihyperglycemic effect in ZDF rats, where it normalizes glucose levels. This drug also has potent glucose-lowering activity in ob/ob mice, where it appears to be equipotent to rosiglitazone on a mass basis. In actuality Compound 11 appears to be 46% more potent than rosiglitazone in vivo, on a mole-per-mole basis; the molecular weight of rosiglitazone is substantially less than Compound 11 (357 vs. 520 g/mol), yet the two drugs produced the same degree of glucose-lowering in ob/ob mice. Our results also indicate that Compound 11 is substantially less adipogenic than rosiglitazone. This effect likely reflects the lower affinity of Compound 11 for PPAR-gamma in comparison to rosiglitazone. We did detect a small increase in weight gain in ZDF rats treated with Compound 11, and we were unable to detect differences in weight gain between rosiglitazone and Compound 11 treated animals in this short-term study. These data are difficult to interpret because the studies were conducted in genetically obese animals, which may have obscured a differential effect of these drugs on weight gain. Several studies in normal animals, up to one month in duration, have failed to demonstrate clinically meaningful weight gain (data not shown).

It is widely held that the weight gain associated with TZDs is partly due to their adipogenic potential, and there has been much effort directed at finding compounds which are potent PPAR-gamma activators but do not cause weight gain. Because Compound 11 has less adipogenic activity, but maintains antihyperglycemic activity, it appears that it may be possible to develop pharmacologic PPAR-gamma activators that produce less weight gain than current commercially available PPAR-gamma activators. In addition to the contribution of adipogenesis, edema is an important factor in the weight gain associated with PPAR-gamma agonists. This toxicity is believed to be directly related to the PPAR-gamma activation potency of the molecule. Because Compound 11 is a weak agonist of PPAR-gamma it may be associated with less edema. Clinical studies underway will help define the effect of Compound 11 on body weight in humans.

The affinity (Ki) of PPAR-gamma for Compound 11 was 6.5-fold less than its affinity for rosiglitazone in preliminary competition binding assays (data not shown), and the transactivation potency was as much as 30-fold less than that of rosiglitazone. In general, there is a relatively strong correlation between PPAR-gamma affinity and glucose-lowering activity; however, recent data indicate that this relationship may not be true for all ligands of this receptor. Recently a non-TZD PPAR-gamma activator, FMOC-L-Leucine, has been shown to have a similar profile to Compound 11. FMOC-L-Leucine has approximately 400-fold less affinity for PPAR-gamma, is only weakly adipogenic, but has potent in vivo antihyperglycemic activity (Rocchi et al, Mol Cell 8:73747, 2001). Differences in in vivo metabolism may explain part of the apparent discrepancy between PPAR-gamma affinity and in vivo antidiabetic potency for Compound 11 and other ligands. Studies by Reginato et al (J Biol Chem 273:32679-84, 1998), Mukherjee et al (Mol Endocrinol 14:1425-33, 2000) and Rocchi et al (Mol Cell 8:737-47, 2001) indicate that ligand-mediated recruitment of the coactivator SRC-1 to PPAR-gamma is an important determinant for differential activities of ligands. At present, we can only speculate on the way in which Compound 11 influences coactivator recruitment to the PPARgamma-RXR complex. It may be that Compound 11 is less conducive for SRC-1 or PGC-1 recruitment and, as a result, transcriptional activation.

A recent study (Nugent et al, Mol Endocrinol 15:1729-38, 2001) reported that in vitro glucose uptake into adipocytes is partially independent of PPAR☐. Whether non-PPAR-gamma-mediated activities or coactivator recruitment explains the unique properties of Compound 11 will require further investigation.

Presently, the mechanism by which PPAR-gamma ligands, including TZDs, produce their antihyperglycemic effects is not known. The prevailing wisdom suggests that the glucose-lowering effect of these drugs is mediated through the PPAR-gamma receptor, which enhances insulin sensitivity. Recent data suggest that the relationship between PPAR-gamma, its ligands and insulin sensitivity is more complex. For example, heterozygous PPAR-gamma null mice actually demonstrate increased insulin sensitivity, and the insulin sensitizing effect of synthetic ligands may result from a balance between transcriptional activation and repression (Miles et al, J Clin Invest 105:287-92, 2000). Additionally, a non-receptor mediated mechanism of action for Compound 11 and other PPAR-gamma agonists cannot be excluded. Indeed, abrogating endogenous PPAR-gamma does not result in the elimination of TZD activity (Nugent et al, Mol Endocrinol 15:1729-38, 2001; Chawla et al, Nat Med 7:48-52, 2001). Our data indicate that Compound 11, in contrast to rosiglitazone, increases glycogen synthesis in liver cells, possibly providing an added mechanism for lowering glucose levels in diabetic animals. Recent data suggest that some non-TZD PPAR-gamma agonists may upregulate genes involved in glycogen synthesis (Way et al, Endocrinology 142:1269-77, 2001). It is becoming apparent that ligands for this receptor will have a spectrum of affinities, transcriptional activities, and in vivo pharmacodynamic profiles. Therefore, there is substantial clinical value in generating compounds with selective PPAR-gamma modulating activities. The acronym SPRM, for "selective PPAR modulator" (Mukherjee et al, Mol Endocrinol 14:1425-33, 2000), may best describe these molecules. SPRMs may ultimately prove to have both specific and tailored activities, including the potential avoidance of weight gain associated with currently marketed TZDs. Such agents would have the potential to be of great benefit in treating patients with type 2 diabetes.

FIG. 20 shows glucose uptake in 3T3-L1 Cells. A. In vitro glucose uptake was measured in differentiated 3T3-L1 adipocytes after 48-h treatment with increasing concentrations of Compound 11 (black bars) or 0.1% DMSO as vehicle (hatched bars). * $P \leq 0.001$. B. Glucose uptake in differentiated 3T3-L1 adipocytes was measured in the presence of increasing concentrations of insulin in the presence of vehicle (circles), rosiglitazone (5 µM) (triangles) or Compound 11 (5 µM) (squares). * $P \leq 0.05$, # $P=0.02$ vs. vehicle.

FIG. 21 shows in vivo Antihyperglycemic Activity of Compound 11 in Diabetic Animals. Diabetic ob/ob mice (A) and db/db mice (B) and diabetic ZDF rats (C) were treated with single daily doses of Compound 11 (50 mg/kg=96.2 µmol/kg) (squares) or vehicle (0.5% carboxymethyl cellulose) (circles) by oral gavage for 8 or 9 days. Blood glucose measurements were made in the fed state. * $P \leq 0.05$, # * $P \leq 0.01$, † $P \leq 0.001$.

FIG. 22 shows in vivo Antihyperglycemic Activity of Compound 11 vs. Rosiglitazone in ob/ob mice. Diabetic ob/ob mice were treated with single daily doses of Compound 11 (squares) and rosiglitazone (triangles) at 10 mg/kg (19.2 and 28.0 µmol/kg, respectively) or vehicle (0.5% carboxymethyl cellulose) (circles) by oral gavage. Blood glucose (A) and body weight (B) were measured during the 8-day treatment period.

Figure 23:
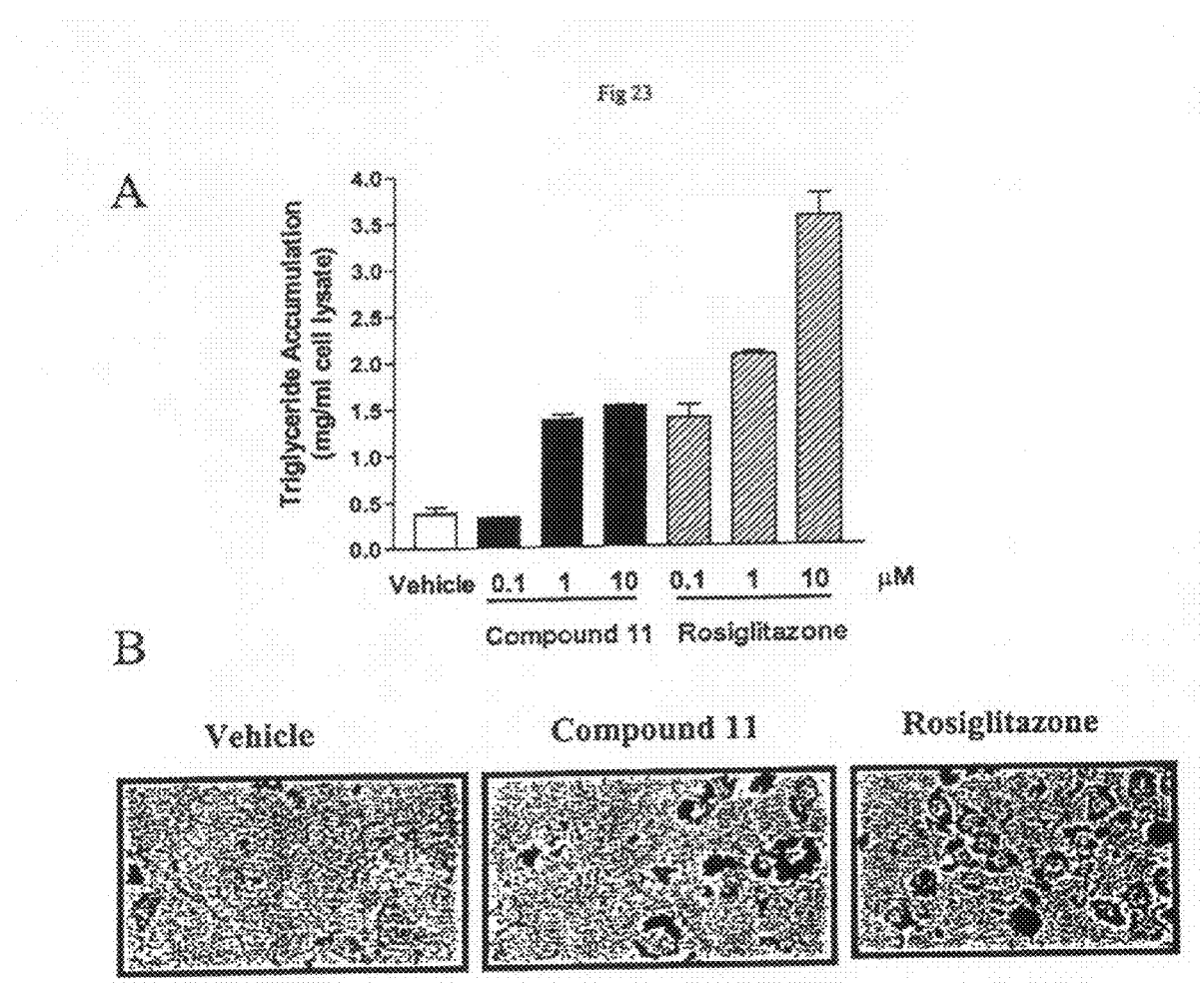
FIG. 23. In Vitro Adipogenic Activity of Compound 11 vs. Rosiglitazone in 3T3-L1 cells. (A) Quantitative measurement of accumulated triglyceride. (B) Qualitative assessment of triglyceride accumulation by Oil Red O.

FIG. 23 shows in vitro Adipogenic Activity of Compound 11. 3T3-L1 cells were cultured with vehicle, Compound 11 or rosiglitazone for 10 days. Total accumulated triglyceride was measured. (A) Quantitative measurement of accumulated triglyceride after 10 days of treatment with increasing concentrations of Compound 11 (black bars) or rosiglitazone (hatched bars) or vehicle (white bar). (B) Qualitative assessment of triglyceride accumulation by Oil Red O after 10-day treatment with 1 µM Compound 11, rosiglitazone or vehicle.

FIG. 24 shows induction of PPARgamma-Mediated Transactivation of PPRE-Luc Reporter by Compound 11 and Rosiglitazone. HEK293 cells were transiently cotransfected with a PPAR-gamma expression vector and a PPRE-Luc reporter construct. Cells were also transfected with a cDNA construct containing Renilla luciferase, which was used to control for transfection efficiency. Transfected cells were treated with increasing concentrations of Compound 11 and rosiglitazone. Luciferase activity is expressed as enhancement over basal levels (no drug) and is corrected for transfection efficiency. The figure shows a representative result of five experiments.

FIG. 25 shows the effect of Compound 11 on In Vitro Glycogen Synthesis in HepG2 Cells. A. Dose-dependent stimulation of glycogen synthesis from glucose by Compound 11 in the absence of insulin at 48 h. Stimulation of glycogen synthesis is expressed as a percentage of basal (vehicle), which is defined as 100%. B. Time-dependent increase in Compound 11-stimulated glycogen synthesis. The maximal effect occurs at 48 to 72 h of treatment with Compound 11. C. Cycloheximide blocks glycogen synthesis induced by Compound 11 (30 µM, 48 h). Vehicle=white bars, Compound 11=black bars, rosiglitazone=hatched bars, CHX=cycloheximide, checked bars, rosi=rosiglitazone.

Co-Administration

The compounds according to the present invention may be combined with a physiologically acceptable carrier or vehicle to provide a pharmaceutical composition, such as, lyophilized powder in the form of tablet or capsule with various fillers and binders. Similarly, the compounds may be co-administered with other agents. Co-administration shall mean the administration of at least two agents to a subject so as to provide the beneficial effects of the combination of both agents. For example, the agents may be administered simultaneously or sequentially over a period of time. The effective dosage of a compound in the composition can be widely varied as selected by those of ordinary skill in the art and may be empirically determined. Moreover, the compounds of the present invention can be used alone or in combination with one or more additional agents depending on the indication and the desired therapeutic effect. For example, in the case of diabetes, insulin resistance and associated conditions or complications, including obesity and hyperlipidemia, such additional agent(s) may be selected from the group consisting of: insulin or an insulin mimetic, a sulfonylurea (such as acetohexamide, chlorpropamide, glimepiride, glipizide, glyburide, tolbutamide and the like) or other insulin secretagogue (such as nateglinide, repaglinide and the like), a thiazolidinedione (such as pioglitazone, rosiglitazone and the like) or other peroxisome proliferator-activated receptor (PPAR)-gamma agonist, a fibrate (such as bezafibrate, clofibrate, fenofibrate, gemfibrozol and the like) or other PPAR-alpha agonist, a PPAR-delta agonist, a biguanide (such as metformin), a statin (such as fluvastatin, lovastatin, pravastatin, simvastatin and the like) or other hydroxymethylglutaryl (HMG) CoA reductase inhibitor, an alpha-glucosidase inhibitor (such as acarbose, miglitol, voglibose and the like), a bile acid-binding resin (such as cholestyramine, celestipol and the like), a high density lipoprotein (HDL)-lowering agent such as apolipoprotein A-I (apoA1), niacin and the like, probucol and nicotinic acid. In the case of inflammation, inflammatory diseases, autoimmune disease and other such cytokine mediated disorders, the additional agent(s) may be selected from the group consisting of: a nonsteroidal anti-inflammatory drug (NSAID) (such as diclofenac, diflunisal, ibuprofen, naproxen and the like), a cyclooxygenase-2 inhibitor (such as celecoxib, rofecoxib and the like), a corticosteroid (such as prednisone, methylprednisone and the like) or other immunosuppressive agent (such as methotrexate, leflunomide, cyclophosphamide, azathioprine and the like), a disease-modifying antirheumatic drug (DMARD) (such as injectable gold, penicillamine, hydroxychloroquine, sulfasalazine and the like), a TNF-alpha inhibitor (such as etanercept, infliximab and the like), other cytokine inhibitor (such as soluble cytokine receptor, anti-cytokine antibody and the like), other immune modulating agent (such as cyclosporin, tacrolimus, rapamycin and the like) and a narcotic agent (such as hydrocodone, morphine, codeine, tramadol and the like). The combination therapy contemplated by the invention includes, for example, administration of the inventive compound and additional agent(s) in a single pharmaceutical formulation as well as administration of the inventive compound and additional agent(s) in separate pharmaceutical formulations.

It will be appreciated that various modifications may be made in the invention as described above and as defined in the following claims wherein:

The invention claimed is:

1. A method of inhibiting the activity of TNF-alpha, IL-1, IL-6, or COX-2, comprising:
administering to a subject a therapeutically effective amount of a compound represented by formula 1:

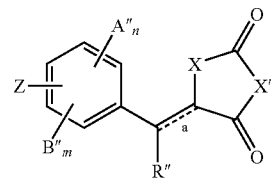

[1]

in a physiologically acceptable carrier;
wherein Z is:

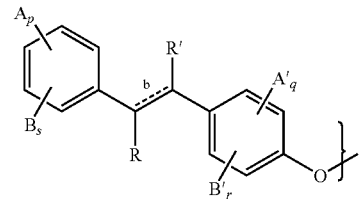

n, m, q and r independently represent integers from zero to 4 provided that n+m≦4 and q+r≦4; p and s are independently integers from zero to 5 provided that p+s≦5; a and b are double bonds which may be present or absent; when present, the double bonds may be in the E or Z configuration and, when absent, the resulting stereocenters may have the R- or S-configuration;

R and R' independently represent hydrogen; $C_1$-$C_{20}$ linear or branched alkyl, linear or branched alkenyl, —$CO_2Z'$, wherein Z' is hydrogen, sodium, potassium, or other pharmaceutically acceptable counter-ion such as calcium, magnesium, ammonium, tromethamine, tetramethylammonium; —CO$_2$R'''; —NH$_2$; —NHR'''; —NR$_2$'''; —OH; —OR'''; halogen; substituted C$_1$-C$_{20}$ linear or branched alkyl or substituted C$_2$-C$_{20}$ linear or branched alkenyl; wherein R''' independently represents C$_1$-C$_{20}$ linear or branched alkyl, linear or branched alkenyl or aralkyl —(CH$_2$)$_x$—Ar, where x is 1-6; —CONR$_2$"", where R"" independently represents hydrogen, optionally substituted C$_1$-C$_{20}$ alkyl, optionally substituted C$_2$-C$_{20}$ alkenyl or optionally substituted C$_6$-C$_{10}$ aryl or where NR$_2$"" represents a cyclic moiety;

R" independently represents hydrogen; C$_1$-C$_{20}$ linear or branched alkyl, C$_2$-C$_{20}$ linear or branched alkenyl, —CO$_2$Z', wherein Z' is hydrogen, sodium, potassium, or other pharmaceutically acceptable counter-ion such as calcium, magnesium, ammonium, tromethamine, tetramethylammonium; —CO$_2$R'''; —NH$_2$; —NHR'''; —NR$_2$'''; —OH; —OR'''; halogen; substituted C$_1$-C$_{20}$ linear or branched alkyl or substituted C$_2$-C$_{20}$ linear or branched alkenyl; wherein R''' independently represents C$_1$-C$_{20}$ linear or branched alkyl, linear or branched alkenyl or aralkyl —(CH$_2$)$_x$—Ar, where x is 1-6;

A, A' and A" independently represent hydrogen; C$_1$-C$_{20}$ acylamino; C$_1$-C$_{20}$ acyloxy; C$_1$-C$_{20}$ alkanoyl; C$_1$-C$_{20}$ alkoxycarbonyl; C$_1$-C$_{20}$ alkoxy; C$_1$-C$_{20}$ alkylamino; C$_1$-C$_{20}$ alkylcarboxylamino; carboxyl; cyano; halogen; hydroxy;

B, B' and B" independently represent hydrogen; C$_1$-C$_{20}$ acylamino; C$_1$-C$_{20}$ acyloxy; C$_1$-C$_{20}$ alkanoyl; C$_1$-C$_{20}$ alkenoyl; C$_1$-C$_{20}$ alkoxycarbonyl; C$_1$-C$_{20}$ alkoxy; C$_1$-C$_{20}$ alkylamino; C$_1$-C$_{20}$ alkylcarboxylamino; aroyl; aralkanoyl; carboxyl; cyano; halogen; hydroxy; nitro; optionally substituted, linear or branched C$_1$-C$_{20}$ alkyl or C$_2$-C$_{20}$ alkenyl; or A and B together, or A' and B' together, or A" and B" together, may be joined to form a methylenedioxy or ethylenedioxy group; and X, X' independently represent

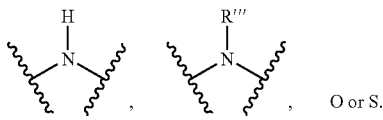
, O or S.

2. The method according to claim 1, wherein said administration treats inflammation.

3. The method according to claim 1, wherein said administration treats hyperlipidemia.

4. The method according to claim 1, wherein said administration treats coronary heart disease.

5. The method according to claim 1, wherein said administration treats vascular restenosis.

6. The method according to claim 1, wherein said administration treats peripheral vascular disease.

7. The method according to claim 1, wherein said administration treats multiple sclerosis.

8. The method according to claim 1, wherein said administration treats rheumatoid arthritis disease.

9. The method according to claim 1, wherein said administration treats inflammatory bowel disease.

10. The method according to claim 1, wherein said administration treats psoriasis.

11. The method according to claim 1, wherein said administration treats at least one of the following: contact dermatitis disease and atopic dermatitis disease.

12. The method according to claim 1, further comprising the co-administration of at least one agent selected from the group consisting of:
a non-steroidal anti-inflammatory drug (NSAID),
a cyclooxygenase-2 inhibitor,
a corticosteroid or other antirheumatic drug (DMARD),
a TNF-alpha inhibitor,
other cytokine inhibitor,
other immune modulating agent,
and a narcotic agent.

13. The method according to claim 1, wherein R, R", A, A', A", B', and B" are all hydrogen, X is sulfur and X' is

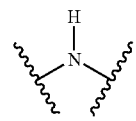
.

14. The method according to claim 13, wherein R' is carbomethoxy and B is methoxy and s is 2.

15. The method according to claim 1, wherein said compound is 5-(4-(4-(1-carbomethoxy-2-(3,5-dimethoxyphenyl)-ethenyl)-phenoxy)-benzyl)-2,4-thiazolidinedione.

16. A method of treating at least one of the following: inflammation, vascular restenosis, peripheral vascular disease, hyperlipidemia, coronary artery disease, multiple sclerosis, rheumatoid arthritis disease, inflammatory bowel disease, psoriasis, contact dermatitis disease, and atopic dermatitis disease, comprising:
administering to a subject a therapeutically effective amount of a compound represented by formula 1:

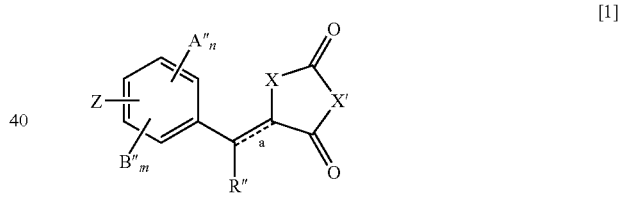

[1]

in a physiologically acceptable carrier;
wherein Z is:

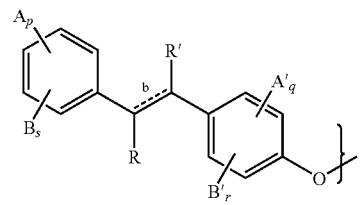

n, m, q and r independently represent integers from zero to 4 provided that n+m≦4 and q+r≦4; p and s are independently integers from zero to 5 provided that p+s≦5; a and b are double bonds which may be present or absent; when present, the double bonds may be in the E or Z configuration and, when absent, the resulting stereocenters may have the R- or S-configuration;

R and R' independently represent hydrogen; C$_1$-C$_{20}$ linear or branched alkyl, linear or branched alkenyl, —CO$_2$Z', wherein Z' is hydrogen, sodium, potassium, or other pharmaceutically acceptable counter-ion such as calcium, magnesium, ammonium, tromethamine, tetramethylammonium; —CO$_2$R'''; —NH$_2$; —NHR'''; —NR$_2$'''; —OH; —OR'''; halogen; substituted C$_1$-C$_{20}$ linear or branched alkyl or substituted C$_2$-C$_{20}$ linear or branched alkenyl; wherein R''' independently represents C$_1$-C$_{20}$ linear or branched alkyl, linear or branched alkenyl or aralkyl —(CH$_2$)$_x$—Ar, where x is 1-6; —CONR$_2$'''', where R'''' independently represents hydrogen, optionally substituted C$_1$-C$_{20}$ alkyl, optionally substituted C$_2$-C$_{20}$ alkenyl or optionally substituted C$_6$-C$_{10}$ aryl or where NR$_2$'''' represents a cyclic moiety;

R'' independently represents hydrogen; C$_1$-C$_{20}$ linear or branched alkyl, C$_2$-C$_{20}$ linear or branched alkenyl, —CO$_2$Z', wherein Z' is hydrogen, sodium, potassium, or other pharmaceutically acceptable counter-ion such as calcium, magnesium, ammonium, tromethamine, tetramethylammonium; —CO$_2$R'''; —NH$_2$; —NHR'''; —NR$_2$'''; —OH; —OR'''; halogen; substituted C$_1$-C$_{20}$ linear or branched alkyl or substituted C$_2$-C$_{20}$ linear or branched alkenyl; wherein R''' independently represents C$_1$-C$_{20}$ linear or branched alkyl, linear or branched alkenyl or aralkyl —(CH$_2$)$_x$—Ar, where x is 1-6;

A, A' and A'' independently represent hydrogen; C$_1$-C$_{20}$ acylamino; C$_1$-C$_{20}$ acyloxy; C$_1$-C$_{20}$ alkanoyl; C$_1$-C$_{20}$ alkoxycarbonyl; C$_1$-C$_{20}$ alkoxy; C$_1$-C$_{20}$ alkylamino; C$_1$-C$_{20}$ alkylcarboxylamino; carboxyl; cyano; halogen; hydroxy;

B, B' and B'' independently represent hydrogen; C$_1$-C$_{20}$ acylamino; C$_1$-C$_{20}$ acyloxy; C$_1$-C$_{20}$ alkanoyl; C$_1$-C$_{20}$ alkenoyl; C$_1$-C$_{20}$ alkoxycarbonyl; C$_1$-C$_{20}$ alkoxy; C$_1$-C$_{20}$ alkylamino; C$_1$-C$_{20}$ alkylcarboxylamino; aroyl; aralkanoyl; carboxyl; cyano; halogen; hydroxy; nitro; optionally substituted, linear or branched C$_1$-C$_{20}$ alkyl or C$_2$-C$_{20}$ alkenyl; or A and B together, or A' and B' together, or A'' and B'' together, may be joined to form a methylenedioxy or ethylenedioxy group; and X, X' independently represent

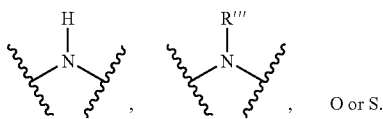
O or S.

17. The method according to claim 16, wherein R, R'', A, A', A'', B', and B'' are all hydrogen, X is sulfur and X' is

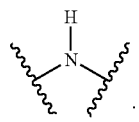

18. The method according to claim 17, wherein R' is carbomethoxy and B is methoxy and s is 2.

19. The method according to claim 16, wherein said compound is 5-(4-(4-(1-carbomethoxy-2-(3,5-dimethoxyphenyl)-ethenyl)-phenoxy)-benzyl)-2,4-thiazolidinedione.

20. The method according to claim 16, wherein said method of treating further inhibits the activity of TNF-alpha, IL-1, IL-6 or COX-2.

21. The method of claim 16, wherein the method treats inflammation.

22. The method of claim 16, wherein the method treats vascular restenosis.

23. The method of claim 16, wherein the method treats peripheral vascular disease.

24. The method of claim 16, wherein the method treats hyperlipidemia.

25. The method of claim 16, wherein the method treats coronary artery disease.

26. The method of claim 16, wherein the method treats multiple sclerosis.

27. The method of claim 16, wherein the method treats rheumatoid arthritis disease.

28. The method of claim 16, wherein the method treats inflammatory bowel disease.

29. The method of claim 16, wherein the method treats psoriasis.

30. The method of claim 16, wherein the method treats at least one of the following: contact dermatitis disease and atopic dermatitis disease.

31. The method of claim 1, wherein said compound is selected from the group comprising:
   i) 3-(3,5-Dimethoxyphenyl)-2-{4-[4-(2,4-dioxothiazolidin-5-ylmethyl)-phenoxy]-phenyl}-acrylamide;
   ii) 3-(3,5-Dimethoxyphenyl)-2-{4-[4-(2,4-dioxothiazolidin-5ylmethyl)-phenoxy]-phenyl}-N,N-dimethylacrylamide; and
   iii) 3-(3,5-Dimethoxyphenyl)-2-{4-[4-(2,4-dioxothiazolidin-5-ylmethyl)-phenoxy]-phenyl}-N-methoxy, N-methyl-acrylamide.

32. The method of claim 16, wherein said compound is selected from the group comprising:
   i) 3-(3,5-Dimethoxyphenyl)-2-{4-[4-(2,4-dioxothiazolidin-5-ylmethyl)-phenoxy]-phenyl}-acrylamide;
   ii) 3-(3,5-Dimethoxyphenyl)-2-{4-[4-(2,4-dioxothiazolidin-5ylmethyl)-phenoxy]-phenyl}-N,N-dimethylacrylamide; and
   iii) 3-(3,5-Dimethoxyphenyl)-2-{4-[4-(2,4-dioxothiazolidin-5-ylmethyl)-phenoxy]-phenyl}-N-methoxy, N-methyl-acrylamide.

* * * * *